(12) United States Patent
Bailly et al.

(10) Patent No.: US 8,883,786 B2
(45) Date of Patent: *Nov. 11, 2014

(54) GLUCOCORTICOID RECEPTOR ANTAGONISTS

(75) Inventors: Jacques Bailly, Zimmersheim (FR);
Cornelia Hertel, Brislach (CH); Daniel Hunziker, Moehlin (CH); Christian Lerner, Binningen (CH); Ulrike Obst Sander, Reinach BL (CH); Jens-Uwe Peters, Grenzach-Wyhlen (DE); Philippe Pflieger, Schwoben (FR); Tanja Schulz-Gasch, Liestal (CH)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/371,834

(22) Filed: Feb. 13, 2012

(65) Prior Publication Data

US 2013/0045972 A1    Feb. 21, 2013

Related U.S. Application Data

(62) Division of application No. 12/210,247, filed on Sep. 15, 2008, now Pat. No. 8,143,280.

(30) Foreign Application Priority Data

Sep. 27, 2007  (EP) .................................... 07117360

(51) Int. Cl.
| | | |
|---|---|---|
| A61K 31/498 | (2006.01) |
| A61K 31/502 | (2006.01) |
| A61K 31/4965 | (2006.01) |
| C07D 277/24 | (2006.01) |
| C07D 277/62 | (2006.01) |
| C07D 498/04 | (2006.01) |
| C07D 231/12 | (2006.01) |
| C07D 233/64 | (2006.01) |
| C07D 239/26 | (2006.01) |
| C07D 241/12 | (2006.01) |
| C07D 401/04 | (2006.01) |
| C07D 215/14 | (2006.01) |
| C07D 471/04 | (2006.01) |
| C07D 213/64 | (2006.01) |
| C07D 213/61 | (2006.01) |
| C07D 217/16 | (2006.01) |
| C07D 401/06 | (2006.01) |
| C07D 249/18 | (2006.01) |
| C07D 213/30 | (2006.01) |
| C07D 237/08 | (2006.01) |

(52) U.S. Cl.
CPC ............ *C07D 241/12* (2013.01); *C07D 277/24* (2013.01); *C07D 277/62* (2013.01); *C07D 498/04* (2013.01); *C07D 231/12* (2013.01); *C07D 233/64* (2013.01); *C07D 239/26* (2013.01); *C07D 401/04* (2013.01); *C07D 215/14* (2013.01); *C07D 471/04* (2013.01); *C07D 213/64* (2013.01); *C07D 213/61* (2013.01); *C07D 217/16* (2013.01); *C07D 401/06* (2013.01); *C07D 249/18* (2013.01); *C07D 213/30* (2013.01); *C07D 237/08* (2013.01)

USPC ........ 514/248; 514/252.1; 514/277; 544/235; 544/336; 544/353; 546/344

(58) Field of Classification Search
USPC .......................... 544/235, 336, 353; 546/344
See application file for complete search history.

(56) References Cited

U.S. PATENT DOCUMENTS

| 5,624,935 | A | 4/1997 | Fujita et al. |
| 2005/0090559 | A1 | 4/2005 | Millen et al. |
| 2007/0060633 | A1* | 3/2007 | Mugge et al. .................. 514/406 |
| 2009/0227538 | A1* | 9/2009 | Fruchtel et al. .................. 514/63 |

FOREIGN PATENT DOCUMENTS

| DE | 10346939 | 5/2005 |
| EP | 1930320 | 6/2008 |
| WO | 00/58293 | 10/2000 |
| WO | 03/082280 | 10/2003 |
| WO | 2005/030213 | 4/2005 |
| WO | 2006/135826 | 12/2006 |
| WO | 2007/087518 | 8/2007 |

OTHER PUBLICATIONS (Translation of Jap Off Act in Corres Jap Appl 2010526248 Nov. 20, 2012).
Andrews, Handbook of the stress and the brain 15:437-450 (2005).
Opherk et al., Mol. Endocrinol. 18(6):1346-1353 (2004).

(Continued)

*Primary Examiner* — Brian McDowell

(57) ABSTRACT

The present invention relates to compounds of formula I

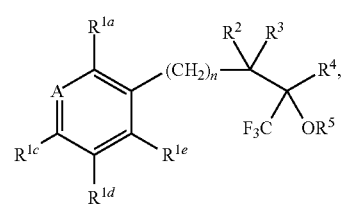

wherein A, n, $R^{1a}$ to $R^{1e}$ and $R^2$ to $R^5$ are as defined in the description and claims, and pharmaceutically acceptable salts thereof. The compounds are glucocorticoid receptor antagonists useful for the treatment and/or prevention of diseases such as diabetes, dyslipidemia, obesity, hypertension, cardiovascular diseases, adrenal imbalance or depression.

13 Claims, No Drawings

(56) References Cited

OTHER PUBLICATIONS

Defronzo, Med. Clin. N. Am. 88:787-835 (2004).
Friedman et al., J. Biol. Chem. 272(50):31475-31481 (1997).
Garrel et al., J. Clin. Endocrinol. Metab. 80(2):379-385 (1995).
Delauney et al., J. Clin. Invest. 100:2094-2098 (1997).
Zinker et al., Meta. Clin. Exp. 57:380-387 (2007).
Nieman et al., J. Clin. Endocrinol. Metab. 61(3):536-540 (1985).
Chu et al., Clin. Endocrinol. Metab. 86:3568-3573 (2001).
Young, Stress 7(4):205-208 (2004).
Gettys et al., Int. J. Obes. 21:865-873 (1997).
Von Geldern et al., J. Med. Chem. 47(17):4213-4230 (2004).
Flores et al., Neuropsychopharmacology 31:628-636 (2006).
Chiodini et al., Eur. J. Endocrinol. 153:837-844 (2005).
Sitruk-Ware et al., Contraception 68:409-420 (2003).
Hu et al., Drug Develop. Res. 67:871-883 (2006).
(International Search Report for PCT/EP2008/062412 Jan. 22, 2009).
Gaillard et al., Pro. Natl. Acad. Sci. 81:3879-3882 (1984).
(Taiwan Office Action in Appl. No. 097137403 Jul. 13, 2011).

* cited by examiner

GLUCOCORTICOID RECEPTOR ANTAGONISTS

PRIORITY TO RELATED APPLICATION(S)

This application is a divisional of U.S. application Ser. No. 12/210,247, filed Sep. 15, 2008 now pending, which claims the benefit of European Patent Application No. 07117360.3, filed Sep. 27, 2007. The entire contents of the above-identified application are hereby incorporated by reference.

FIELD OF THE INVENTION

The present invention relates to novel 1,1,1-trifluoro-2-hydroxy-3-phenylpropane or 1,1,1-trifluoro-2-hydroxy-4-phenylbutane derivatives, their manufacture, pharmaceutical compositions containing them and their use as medicaments. The active compounds of the present invention are acting as modulators of the glucocorticoid receptor, preferably antagonists, and are useful in treating diabetes and other disorders such as dyslipidemia, obesity, hypertension, cardiovascular diseases, adrenal imbalance or depression.

This application is a divisional of U.S. application Ser. No. 12/210,247, filed Sep. 15, 2008 now pending, which claims the benefit of European Patent Application No. 07117360.3, filed Sep. 27, 2007. The entire contents of the above-identified application are hereby incorporated by reference.

In particular, the present invention relates to compounds the general formula

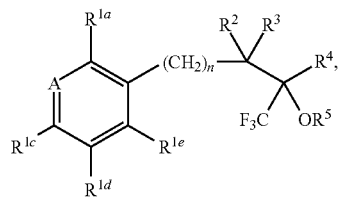

and pharmaceutically acceptable salts thereof.

All documents cited to and/or relied upon below are expressly incorporated herein by reference.

BACKGROUND

Glucocorticoids are responsible for several physiological functions including answer to stress, immune and inflammatory responses as well as stimulation of hepatic gluconeogenesis and glucose utilization at the periphery. Glucocorticoids act via an intracellular glucocorticoid receptor (GR) belonging to the family of the nuclear steroidal receptors. The non-activated GR is located in the cellular cytoplasm and is associated with several chaperone proteins. When a ligand activates the receptor, the complex is translocated in the cell nucleus and interacts with the glucocorticoid response element which is located in several gene promoters. The receptor could act in the cell nucleus as an homodimer or an heterodimer. Moreover several associated co-activators or co-repressors could also interact with the complex. This large range of possible combinations leads to several GR conformations and several possible physiological answers.

Pathologies like diabetes, Cushing's syndrome or depression have been associated with moderate to severe hypercortisolism (Chiodini et al, *Eur. J. Endocrinol.* 2005, Vol. 153, pp 837-844; Young, *Stress* 2004, Vol. 7 (4), pp 205-208). GR antagonist administration has been proven to be clinically active in depression (Flores et al, *Neuropsychopharmacology* 2006, Vol. 31, pp 628-636) or in Cushing's syndrome (Chu et al, *J. Clin. Endocrinol. Metab.* 2001, Vol. 86, pp 3568-3573). These clinical evidences illustrate the potential clinical value of a potent and selective GR antagonist in many indications like diabetes, dyslipidemia, obesity, hypertension, cardiovascular diseases or depression (Von Geldern et al, *J. Med. Chem.* 2004, Vol 47 (17), pp 4213-4230; Hu et al, *Drug Develop. Res.* 2006, Vol. 67, pp 871-883; Andrews, Handbook of the stress and the brain 2005, Vol. 15, pp 437-450). This approach might also improve peripheral insulin sensitivity (Zinker et al, *Meta. Clin. Exp.* 2007, Vol. 57, pp 380-387) and protect pancreatic beta cells (Delauney et al, *J. Clin. Invest.* 1997, Vol. (100, pp 2094-2098).

Diabetic patients have an increased level of fasting blood glucose which has been correlated in clinic with an impaired control of gluconeogenesis (DeFronzo, *Med. Clin. N. Am.* 2004, Vol. 88 pp 787-835). The hepatic gluconeogenesis process is under the control of glucocorticoids. Clinical administration of a non-specific GR antagonist (RU486/mifepristone) leads acutely to a decrease of fasting plasma glucose in normal volunteers (Garrel et al, *J. Clin. Endocrinol. Metab.* 1995, Vol. 80 (2), pp 379-385) and chronically to a decrease of plasmatic HbA1c in Cushing's patients (Nieman et al, *J. Clin. Endocrinol. Metab.* 1985, Vol. 61 (3), pp 536-540). Moreover, this drug given to leptin deficient animals normalizes fasting plasma glucose (ob/ob mice, Gettys et al, *Int. J. Obes.* 1997, Vol. 21, pp 865-873) as well as the activity of gluconeogenic enzymes (db/db mice, Friedman et al, *J. Biol. Chem.* 1997, Vol. 272 (50) pp 31475-31481). Liver-specific knockout mice have been produced and these animals display a moderate hypoglycemia when they are fasted for 48 h excluding the risk of severe hypoglycemia (Opherk et al, *Mol. Endocrinol.* 2004, Vol. 18 (6), pp 1346-1353).

Mifepristone is also known to stimulate the Hypothalamus-Pituitary gland-Adrenal gland (HPA) axis via the activation of a feed-back mechanism which leads to an increase of endogenous corticosteroids circulating in the blood (Gaillard et al, *Pro. Natl. Acad. Sci.* 1984, Vol. 81, pp 3879-3882). Mifepristone also induces some adrenal insufficiency symptoms after long term treatment (up to 1 year, for review see: Sitruk-Ware et al, 2003, Contraception, Vol. 68, pp 409-420).

For GR modulators to be used in indications such as diabetes, dyslipidemia, obesity, hypertension and cardiovascular diseases it is necessary to limit the risk to activate or inhibit the HPA axis. Several strategies can be used to achieve this goal like to have a drug with a moderate to high liver selectivity or to get a drug which would not penetrate brain. Liver selectivity can be obtained by introducing liver targeting vectors in the molecule or by limiting the volume of distribution of the substance in the body. On the opposite for GR modulators to be used in indications such as adrenal/HPA imbalance, insomnia or depression it will be necessary to obtain a drug with a moderate to high brain selectivity.

SUMMARY OF THE INVENTION

In an embodiment of the present invention, provided is a compound of formula I:

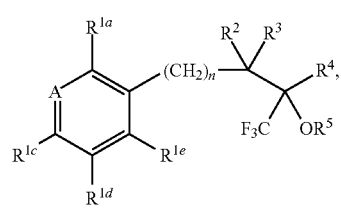

wherein:
A is C—$R^{1b}$ or N;
$R^{1a}$, $R^{1b}$, $R^{1c}$, $R^{1d}$ and $R^{1e}$ independently from each other are selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy, di-$C_{1-7}$-alkylamino, di-$C_{2-7}$-alkenylamino, $C_{1-7}$-alkylsulfonylamino, phenylcarbonylamino, phenylsulfonyloxy, heteroaryl-$C_{1-7}$-alkoxy, wherein the heteroaryl ring is selected from the group consisting of oxadiazolyl, isoxazolyl, thiadiazolyl and tetrazolyl and is unsubstituted or substituted by $C_{1-7}$-alkyl, phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy;

or $R^{1c}$ and $R^{1d}$ or $R^{1d}$ and $R^{1e}$ together are —CH═CH—CH═CH— to form a phenyl ring together with the carbon atoms to which they are attached;

$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;

$R^3$ is hydrogen or $C_{1-7}$-alkyl;

or $R^2$ and $R^3$ together with the carbon atom they are attached to form a $C_3$-$C_5$-cycloalkyl ring;

$R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrazolyl, imidazolyl, thiazolyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^6R^7N$-carbonyl-$C_{1-7}$-alkoxy, wherein $R^6$ and $R^7$ are independently selected from hydrogen or $C_{1-7}$-alkyl or $R^6$ and $R^7$ together with the nitrogen atom they are attached to form a heterocyclic ring selected from pyrrolidine, piperidine, morpholine or thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy;

pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy;

$R^5$ is hydrogen or methyl;

n is 0 or 1;

and pharmaceutically acceptable salts thereof.

In another embodiment of the present invention, provided is a pharmaceutical composition, comprising a therapeutically effective amount of a compound according to formula I and a pharmaceutically acceptable carrier and/or adjuvant.

In a further embodiment of the present invention, provided is a method for the treatment of diseases which are associated with glucocorticoid receptor modulation, comprising the step of administering a therapeutically active amount of a compound according to formula I to a human being or animal in need thereof.

DETAILED DESCRIPTION

The present invention provides for potent and highly selective modulators of the glucocorticoid receptor (GR), preferably GR antagonists, with various tissue selectivities. Such GR modulators are useful as therapeutically active substances, particularly in the treatment and/or prevention of diseases which are associated with modulation of the glucocorticoid receptors.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "lower alkenyl" or "$C_{2-7}$-alkenyl" signifies a straight-chain or branched chain hydrocarbon residue comprising an olefinic bond and 1 to 7, preferably 1 to 6, particularly preferred 1 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by cycloalkyl. A preferred example is cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy and most preferred ethoxy.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by another alkoxy group. Also included are groups wherein the second alkoxy group is substituted by a further alkoxy group. Among the preferred lower alkoxyalkoxy groups are 1-methoxymethoxy, 2-methoxyethoxy, 3-methoxypropyloxy and 2-(2-methoxyethoxy)-ethoxy.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the preferred lower hydroxyalkyl groups are hydroxymethyl or hydroxyethyl.

The term "lower hydroxyalkoxy" or "hydroxy-$C_{1-7}$-alkoxy" means a lower alkoxy group as defined herein before wherein at least one of the hydrogen atoms of the lower alkoxy group is replaced by a hydroxy group. A preferred lower hydroxyalkoxy group is 2-hydroxyethoxy.

The term "lower aminoalkoxy" or "amino-$C_{1-7}$-alkoxy" means a lower alkoxy group as defined herein before wherein at least one of the hydrogen atoms of the lower alkoxy group is replaced by an amino group. A preferred lower aminoalkoxy group is 2-aminoethoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluormethoxy and chloromethoxy, with trifluoromethoxy being especially preferred.

The term "lower alkoxycarbonyl" or "$C_{1-7}$-alkoxycarbonyl" refers to the group —CO—OR' wherein R' is lower alkyl and the term "lower alkyl" has the previously given significance. Preferred lower alkoxycarbonyl groups are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A preferred lower alkoxycarbonylalkyl group is —$CH_2$—$COOCH_3$.

The term "lower alkoxycarbonylalkoxy" or "$C_{1-7}$-alkoxycarbonyl-$C_{1-7}$-alkoxy" refers to lower alkoxy groups as defined above wherein one of the hydrogen atoms of the lower alkoxy group is replaced by $C_{1-7}$-alkoxycarbonyl. A preferred lower alkoxycarbonylalkoxy group is t-butoxycarbonylmethoxy (—O—$CH_2$—COO—$C(CH_3)_3$).

The term "lower alkoxycarbonylaminoalkoxy" or "$C_{1-7}$-alkoxycarbonylamino-$C_{1-7}$-alkoxy" refers to lower alkoxy groups as defined above wherein one of the hydrogen atoms of the lower alkoxy group is replaced by $C_{1-7}$-alkoxycarbonylamino. A preferred lower alkoxycarbonylaminoalkoxy group is —O—$CH_2$—$CH_2$—NH—COO—$C(CH_3)_3$.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the preferred lower carboxyl alkyl groups are carboxylmethyl (—$CH_2$—COOH) and carboxylethyl (—$CH_2$—$CH_2$—COOH), with carboxylmethyl being especially preferred.

The term "lower carboxylalkoxy" or "carboxyl-$C_{1-7}$-alkoxy" refers to lower alkoxy groups as defined above wherein at least one of the hydrogen atoms of the lower alkoxy group is replaced by a carboxyl group. Preferred lower carboxylalkoxy group is carboxylmethoxy (—O—$CH_2$—COOH).

The term "$C_{1-7}$-alkylcarbonyl" means the group —CO—R, wherein R is lower alkyl as defined above.

The term "$C_{1-7}$-alkylcarbonyloxy" refers to the group —O—CO—R, wherein R is lower alkyl as defined herein before.

The term "lower alkylcarbonyloxyalkoxy" or "$C_{1-7}$-alkylcarbonyloxy-$C_{1-7}$-alkoxy" refers to lower alkoxy groups as defined above wherein one of the hydrogen atoms of the lower alkoxy group is replaced by $C_{1-7}$-alkylcarbonyloxy. A preferred lower alkylcarbonyloxyalkoxy group is —O—$CH_2$—$CH_2$—O—CO—$CH_3$.

The term "aminocarbonylalkoxy" or "aminocarbonyl-$C_{1-7}$-alkoxy" refers to lower alkoxy groups as defined above wherein one of the hydrogen atoms of the lower alkoxy group is replaced by aminocarbonyl. A preferred aminocarbonylalkoxy group is the group —O—$CH_2$—CO—$NH_2$.

The term "di-$C_{1-7}$-alkylamino" signifies the group —NR'R", wherein R' and R" are lower alkyl as defined above.

The term "di-$C_{1-7}$-alkenylamino" signifies the group —NR'R", wherein R' and R" are lower alkenyl groups as defined above. A preferred dialkenylamino group is diallylamino.

The term "$C_{1-7}$-alkylsulfonyl" means the group —$S(O)_2$—R, wherein R is lower alkyl as defined above.

The term "$C_{1-7}$-alkylsulfonylamino" refers to the group —NH—$S(O)_2$—R, wherein R is lower alkyl as defined above.

The term "halogen-$C_{1-7}$-alkyl-sulfonyloxy" means the group —O—$S(O)_2$—R", wherein R" is lower halogenalkyl as defined above. Preferred halogenalkylsulfonyloxy is trifluoromethanesulfonyloxy.

The term "phenyloxy" refers to the group —O-phenyl.

The term "lower phenylalkyl" or "phenyl-$C_{1-7}$-alkyl" refers to lower alkyl groups as defined above wherein at least one of the hydrogen atoms of the lower alkyl group is replaced by a phenyl group. The phenyl group may be further substituted. Preferred lower phenylalkyl groups are benzyl or phenethyl.

The term "lower phenylalkoxy" or "phenyl-$C_{1-7}$-alkoxy" refers to lower alkoxy groups as defined above wherein at least one of the hydrogen atoms of the lower alkoxy group is replaced by a phenyl group. The phenyl group may be further substituted. Preferred lower phenylalkoxy group is benzyloxy.

The term "phenylcarbonylamino" means the group —NH—C(O)-phenyl.

The term "phenylsulfonyloxy" refers to the group —O—$S(O)_2$-phenyl.

The term "heteroaryl" in general refers to an aromatic 5- or 6-membered ring which comprises at least one nitrogen atom and can in addition comprise one or two atoms selected from nitrogen, oxygen and/or sulphur, such as pyridyl, pyrazinyl, pyrimidinyl, pyridazinyl, 2-oxo-1,2-dihydropyridinyl, oxadiazolyl, isoxazolyl, thiadiazolyl, tetrazolyl pyrazolyl, imidazolyl and thiazolyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as quinolinyl, isoquinolinyl, cinnolinyl, pyrazolyl, imidazolyl, thiazolyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl. Preferred heteroaryl groups are pyridyl and pyrazinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compounds of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I or II (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The present invention relates to compounds of the general formula

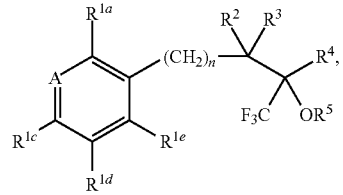

wherein
A is C—$R^{1b}$ or N;
$R^{1a}$, $R^{1b}$, $R^{1c}$, $R^{1d}$ and $R^{1e}$ independently from each other are selected from the group consisting of hydrogen, $C_{1-7}$-alkyl, $C_{3-7}$-cycloalkyl-$C_{1-7}$-alkyl,
halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano,
carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy,
di-$C_{1-7}$-alkylamino, di-$C_{2-7}$-alkenylamino, $C_{1-7}$-alkylsulfonylamino,
phenylcarbonylamino, phenylsulfonyloxy,
heteroaryl-$C_{1-7}$-alkoxy, wherein the heteroaryl ring is selected from the group consisting of oxadiazolyl, isoxazolyl, thiadiazolyl and tetrazolyl and is unsubstituted or substituted by $C_{1-7}$-alkyl,
phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy;
or $R^{1c}$ and $R^{1d}$ or $R^{1d}$ and $R^{1e}$ together are —CH═CH—CH═CH— to form a phenyl ring together with the carbon atoms to which they are attached;
$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;
$R^3$ is hydrogen or $C_{1-7}$-alkyl;
or $R^2$ and $R^3$ together with the carbon atom they are attached to form a $C_3$-$C_5$-cycloalkyl ring;
$R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrazolyl, imidazolyl, thiazolyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl,
said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-7-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^6R^7$N-carbonyl-$C_{1-7}$-alkoxy, wherein $R^6$ and $R^7$ are independently selected from hydrogen or $C_{1-7}$-alkyl or $R^6$ and $R^7$ together with the nitrogen atom they are attached to form a heterocyclic ring selected from pyrrolidine, piperidine, morpholine or thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy;

pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy;

$R^5$ is hydrogen or methyl;

n is 0 or 1;

and pharmaceutically acceptable salts thereof.

Preferred compounds of formula I of the invention are those, wherein n is 0, meaning these are compounds having the formula I-B

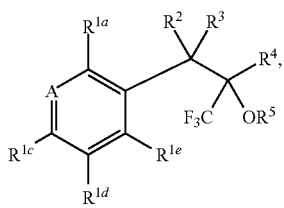

I-B wherein A, $R^{1a}$, $R^{1c}$, $R^{1d}$, $R^{1e}$, $R^2$, $R^3$, $R^4$ and $R^5$ are as defined herein before.

The present invention also comprises compounds of formula I, wherein n is 1, meaning these are compounds having the formula I-C

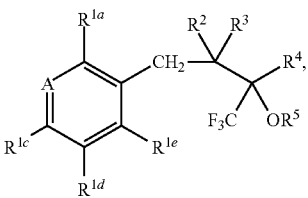

I-C wherein A, $R^{1a}$, $R^{1c}$, $R^{1d}$, $R^{1e}$, $R^2$, $R^3$, $R^4$ and $R^5$ are as defined herein before.

Preferred are furthermore compounds of formula I of the invention, wherein A is C—$R^{1b}$, meaning these are compounds having the formula I-D

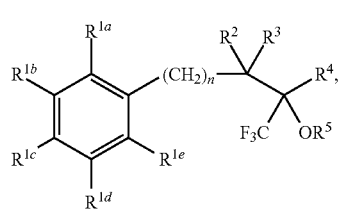

I-D wherein n, $R^{1a}$, $R^{1b}$, $R^{1c}$, $R^{1d}$, $R^{1e}$, $R^2$, $R^3$, $R^4$ and $R^5$ are as defined herein before.

The invention also embraces compounds of formula I, wherein A is N, meaning compounds having the formula I-E

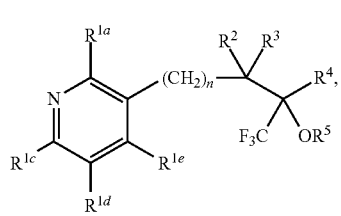

I-E wherein n, $R^{1a}$, $R^{1c}$, $R^{1d}$, $R^{1e}$, $R^2$, $R^3$, $R^4$ and $R^5$ are as defined herein before.

Further preferred are compounds of formula I according to the invention, wherein $R^{1a}$, $R^{1b}$, $R^{1c}$, $R^{1d}$ and $R^{1e}$, independently from each other are selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxy-carbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy, di-$C_{1-7}$-alkylamino, di-$C_{2-7}$-alkenylamino, $C_{1-7}$-alkylsulfonylamino, phenylcarbonylamino, phenylsulfonyloxy, heteroaryl-$C_{1-7}$-alkoxy, wherein the heteroaryl ring is selected from the group consisting of oxadiazolyl, isoxazolyl, thiadiazolyl and tetrazolyl and is unsubstituted or substituted by $C_{1-7}$-alkyl, phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy; and wherein not more than three of $R^{1a}$, $R^{1b}$, $R^{1c}$, $R^{1d}$ and $R^{1e}$ are hydrogen.

Another preferred group of compounds of formula I according to the present invention are those, wherein $R^{1a}$, $R^{1b}$, $R^{1c}$, $R^{1d}$ and $R^{1e}$ are selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, hydroxy, $C_{1-7}$-alkoxy, carboxyl, carboxyl-$C_{1-7}$-alkyl, carboxyl-$C_{1-7}$-alkoxy, phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, $C_{1-7}$-alkoxy and halogen-$C_{1-7}$-alkoxy and not more than three of $R^{1a}$, $R^{1b}$, $R^{1c}$, $R^{1d}$ and $R^{1e}$ are hydrogen.

Compounds of formula I are also preferred, wherein $R^{1a}$, $R^{1b}$, $R^{1c}$, $R^{1d}$ and $R^{1e}$ are selected from the group consisting of hydrogen, halogen, halogen-$C_{1-7}$-alkyl, hydroxy, $C_{1-7}$-alkoxy, cyano, carboxyl, $C_{1-7}$-alkoxycarbonyl, di-$C_{2-7}$-alkenylamino, heteroaryl-$C_{1-7}$-alkoxy, wherein the heteroaryl ring is selected from the group consisting of oxadiazolyl, isoxazolyl, thiadiazolyl and tetrazolyl and is unsubstituted or substituted by $C_{1-7}$-alkyl, phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy.

Further preferred are compounds of formula I of the invention, wherein $R^{1a}$, $R^{1b}$, $R^{1c}$, $R^{1d}$ and $R^{1e}$ are selected from the group consisting of hydrogen, halogen, halogen-$C_{1-7}$-alkyl, hydroxy, $C_{1-7}$-alkoxy, carboxyl, phenyloxy and phenyl-$C_{1-7}$-alkoxy.

The invention further comprises compounds of formula I, wherein $R^{1c}$ and $R^{1d}$ together or $R^{1d}$ and $R^{1e}$ together are —CH=CH—CH=CH— to form a phenyl ring together with the carbon atoms to which they are attached, meaning these are compounds of the formula I-F or I-G

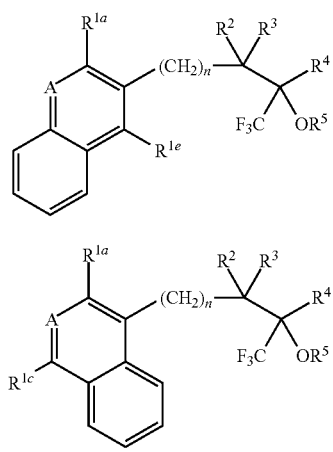

Especially preferred are compounds of formula I according to the invention, wherein $R^{1a}$ is halogen. Most preferred $R^{1a}$ is chloro.

In addition, compounds of formula I are especially preferred, wherein $R^{1a}$ is halogen and $R^{1c}$ is selected from the group consisting of halogen, $C_{1-7}$-alkoxy and phenyl-$C_{1-7}$-alkoxy.

Especially preferred are also compounds of formula I according to the present invention, wherein $R^2$ is $C_{1-7}$-alkyl. More preferably, $R^2$ is methyl.

The invention also relates to compounds of formula I, wherein $R^2$ is selected from the group consisting of $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups.

Compounds of formula I according to the invention are also preferred, wherein $R^2$ is $C_{3-7}$-cycloalkyl-$C_{1-7}$-alkyl or triazolyl-$C_{1-7}$-alkyl.

More preferably, $R^2$ is selected from methyl, ethyl, propyl, butyl, cyclopropylmethyl, methoxycarbonylmethyl, carboxylmethyl, triazolylmethyl and 2,4-dichlorophenyl.

Furthermore, compounds of formula I according to the present invention are preferred, wherein $R^3$ is hydrogen.

Another group of preferred compounds of formula I according to the invention are those, wherein $R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrazolyl, imidazolyl, thiazolyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, cyano, $C_{1-7}$-alkyl, $C_{1-7}$-alkoxy, cyano-$C_{1-7}$-alkoxy, carboxyl-$C_{1-7}$-alkoxy, $C_{1-7}$-alkoxycarbonyl, phenyl, pyridyl, pyrrolidinyl and phenyl-$C_{1-7}$-alkoxy.

Especially preferred are compounds of formula I according to the invention, wherein $R^4$ is a heteroaryl ring selected from the group consisting of pyridyl, pyrazinyl, pyrimidinyl, pyridazinyl and 2-oxo-1,2-dihydropyridinyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^6R^7N$-carbonyl-$C_{1-7}$-alkoxy, wherein $R^6$ and $R^7$ are independently selected from hydrogen or $C_{1-7}$-alkyl or $R^6$ and $R^7$ together with the nitrogen atom they are attached to form a heterocyclic ring selected from pyrrolidine, piperidine, morpholine or thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy, pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy.

More preferred are compounds of the present invention, wherein $R^4$ is a heteroaryl ring selected from the group consisting of pyridyl, pyrazinyl, pyrimidinyl and pyridazinyl, said heteroaryl ring being unsubstituted or substituted by one, two or three substituents selected from the group consisting of halogen, halogen-$C_{1-7}$-alkyl, $C_{1-7}$-alkyl, $C_{3-7}$-cycloalkyl-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy.

Further preferred are compounds of formula I according to the invention, wherein $R^4$ is pyridyl, said pyridyl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^6R^7N$-carbonyl-$C_{1-7}$-alkoxy, wherein $R^6$ and $R^7$ are independently selected from hydrogen or $C_{1-7}$-alkyl or $R^6$ and $R^7$ together with the nitrogen atom they are attached to form a heterocyclic ring selected from pyrrolidine, piperidine, morpholine or thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy; pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy.

More preferred are compounds of formula I according to the invention, wherein $R^4$ is pyridyl, said pyridyl ring being unsubstituted or substituted by one, two or three substituents selected from the group consisting of halogen, halogen-$C_{1-7}$-alkyl, $C_{1-7}$-alkyl, $C_{3-7}$-cycloalkyl-$C_{1-7}$-alkyl, $C_{1-7}$-alkoxy, cyano, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy, with those compounds of formula I being most preferred, wherein $R^4$ is pyridyl substituted by one, two or three substituents selected from the group consisting of halogen, $C_{1-7}$-alkyl, cyano, $C_{1-7}$-alkoxy and carboxyl-$C_{1-7}$-alkoxy.

Further preferred compounds of formula I according to the invention are those, wherein $R^4$ is a heteroaryl ring selected from the group consisting of quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^6R^7$N-carbonyl-$C_{1-7}$-alkoxy, wherein $R^6$ and $R^7$ are independently selected from hydrogen or $C_{1-7}$-alkyl or $R^6$ and $R^7$ together with the nitrogen atom they are attached to form a heterocyclic ring selected from pyrrolidine, piperidine, morpholine or thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy; pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy.

More preferred are those compounds of formula I, wherein $R^4$ is a heteroaryl ring selected from the group consisting of quinolinyl, pyrazolo[1,5-a]pyridyl, imidazo[1,2-a]pyridyl, quinoxalinyl, benzothiazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, $C_{1-7}$-alkyl, $C_{3-7}$-cycloalkyl-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy.

Compounds of formula I according to the invention are especially preferred, wherein $R^4$ is quinolinyl, said quinolinyl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy.

Also especially preferred are compounds of formula I according to the invention, wherein $R^4$ is benzothiazolyl, said benzothiazolyl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy.

Further preferred are compounds of formula I according to the present invention, wherein $R^4$ is a heteroaryl ring selected from the group consisting of pyrazolyl, imidazolyl and thiazolyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^6R^7$N-carbonyl-$C_{1-7}$-alkoxy, wherein $R^6$ and $R^7$ are independently selected from hydrogen or $C_{1-7}$-alkyl or $R^6$ and $R^7$ together with the nitrogen atom they are attached to form a heterocyclic ring selected from pyrrolidine, piperidine, morpholine or thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy; pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy.

More preferably, said pyrazolyl, imidazolyl and thiazolyl ring is unsubstituted or substituted by one, two or three substituents selected from the group consisting of halogen, halogen-$C_{1-7}$-alkyl, $C_{1-7}$-alkyl, $C_{3-7}$-cycloalkyl-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy.

Especially preferred are further compounds of formula I according to the invention, wherein $R^5$ is hydrogen.

Compounds of formula I according to the invention are also preferred, wherein $R^5$ is methyl.

Especially preferred are furthermore compounds of formula I having the formula

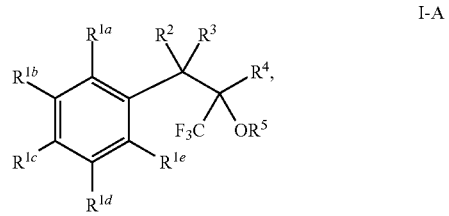

I-A wherein
$R^{1a}, R^{1b}, R^{1c}, R^{1d}$ and $R^{1e}$ independently from each other are selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, hydroxy, $C_{1-7}$-alkoxy, carboxyl, carboxyl-$C_{1-7}$-alkyl, carboxyl-$C_{1-7}$-alkoxy, phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, $C_{1-7}$-alkoxy and halogen-$C_{1-7}$-alkoxy;
$R^2$ is selected from the group consisting of $C_{1-7}$-alkyl, $C_{3-7}$-cycloalkyl-$C_{1-7}$-alkyl and triazolyl-$C_{1-7}$-alkyl;
$R^3$ is hydrogen or $C_{1-7}$-alkyl;
$R^4$ is a heteroaryl ring selected from the group consisting of pyridyl, pyrazinyl, pyrimidinyl, pyridazinyl, quinolinyl, pyrazolyl, imidazolyl, thiazolyl, pyrazolo[1,5-a]pyridyl, imidazo[1,2-a]pyridyl, quinoxalinyl, benzothiazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, $C_{1-7}$-alkyl, $C_{3-7}$-cycloalkyl-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy;
$R^5$ is hydrogen or methyl;
and pharmaceutically acceptable salts thereof.

The following are preferred compounds of formula I of the present invention:

3-(2-chloro-4-methoxy-phenyl)-1,1,1-trifluoro-2-(5-methyl-pyrazin-2-yl)-butan-2-ol,
1,1,1-trifluoro-2-(2-methyl-pyridin-4-yl)-3-phenyl-butan-2-ol,
3-(2-chloro-4-methoxy-phenyl)-1,1,1-trifluoro-2-(2-methyl-pyridin-4-yl)-butan-2-ol,
3-(2-chloro-4-ethoxy-phenyl)-1,1,1-trifluoro-2-(2-methyl-pyridin-4-yl)-pentan-2-ol,
3-(2-chloro-4-propoxy-phenyl)-1,1,1-trifluoro-2-(2-methyl-pyridin-4-yl)-hexan-2-ol,
3-(2,3-dichloro-4-methoxy-phenyl)-1,1,1-trifluoro-2-(2-methyl-pyridin-4-yl)-butan-2-ol,
3-(2-chloro-5-methoxy-phenyl)-1,1,1-trifluoro-2-(2-methyl-pyridin-4-yl)-butan-2-ol,
3-(2,5-dichloro-phenyl)-1,1,1-trifluoro-2-(2-methyl-pyridin-4-yl)-butan-2-ol,
1,1,1-trifluoro-3-phenyl-2-pyridin-4-yl-butan-2-ol,
3-(2,4-dichloro-phenyl)-1,1,1-trifluoro-2-pyridin-3-yl-butan-2-ol,
3-(2,4-dichloro-phenyl)-1,1,1-trifluoro-2-pyridin-4-yl-butan-2-ol,
3-(2,4-dichloro-phenyl)-1,1,1-trifluoro-2-pyridin-2-yl-butan-2-ol,
3-(2,4-dichloro-phenyl)-1,1,1-trifluoro-2-pyridin-3-yl-heptan-2-ol,
3-(2,4-dichloro-phenyl)-1,1,1-trifluoro-2-pyridin-3-yl-hexan-2-ol,
3-(2,4-dichloro-phenyl)-1,1,1-trifluoro-2-pyridin-3-yl-pentan-2-ol,
4-cyclopropyl-3-(2,4-dichloro-phenyl)-1,1,1-trifluoro-2-pyridin-3-yl-butan-2-ol,
3-(4-chloro-2-fluoro-phenyl)-1,1,1-trifluoro-2-pyridin-3-yl-butan-2-ol,
3-(2-chloro-phenyl)-1,1,1-trifluoro-2-pyridin-3-yl-butan-2-ol,
3-(3,4-dichloro-phenyl)-1,1,1-trifluoro-2-pyridin-3-yl-butan-2-ol,
3-(2,3-dichloro-phenyl)-1,1,1-trifluoro-2-pyridin-3-yl-butan-2-ol,
3-(3-chloro-phenyl)-1,1,1-trifluoro-2-pyridin-3-yl-butan-2-ol,
3-(2,4-dichloro-phenyl)-1,1,1-trifluoro-2-(6-trifluoromethyl-pyridin-3-yl)-butan-2-ol,
3-(2,4-dichloro-phenyl)-1,1,1-trifluoro-2-pyridin-3-yl-4-[1,2,4]triazol-1-yl-butan-2-ol,
3-(2,4-dichloro-phenyl)-1,1,1-trifluoro-2-pyridin-4-yl-hexan-2-ol,
3-(2-chloro-4-fluoro-phenyl)-1,1,1-trifluoro-2-pyridin-4-yl-hexan-2-ol,
1,1,1-trifluoro-3-(2-methoxy-phenyl)-2-pyridin-4-yl-hexan-2-ol,
3-(2,4-dichloro-phenyl)-1,1,1-trifluoro-2-(2-methyl-pyridin-4-yl)-butan-2-ol,
3-(2,4-dichloro-phenyl)-1,1,1-trifluoro-2-(2-methyl-pyridin-4-yl)-hexan-2-ol,
3-(2,4-dichloro-phenyl)-1,1,1-trifluoro-2-pyrazin-2-yl-butan-2-ol,
1,1,1-trifluoro-3-(2-methoxy-phenyl)-2-(2-methyl-pyridin-4-yl)-butan-2-ol,
3-(2-chloro-5-trifluoromethyl-phenyl)-1,1,1-trifluoro-2-pyridin-4-yl-butan-2-ol,
3-(2-chloro-6-fluoro-phenyl)-1,1,1-trifluoro-2-pyridin-4-yl-butan-2-ol,
1,1,1-trifluoro-2-pyridin-4-yl-3-o-tolyl-butan-2-ol,
3-(2-chloro-4-fluoro-phenyl)-2-(2-chloro-pyridin-4-yl)-1,1,1-trifluoro-butan-2-ol,
3-(2,4-dichloro-phenyl)-1,1,1-trifluoro-2-pyridazin-4-yl-butan-2-ol,
1,1,1-trifluoro-3-(2-phenoxy-phenyl)-2-pyridin-4-yl-butan-2-ol,
3-(2,4-dichloro-phenyl)-1,1,1-trifluoro-2-(2-methoxy-pyridin-4-yl)-butan-2-ol,
3-(2,4-dichloro-phenyl)-1,1,1-trifluoro-2-(5-methyl-pyrazin-2-yl)-butan-2-ol,
3-(2,4-dichloro-phenyl)-1,1,1-trifluoro-2-(6-methyl-pyrazin-2-yl)-butan-2-ol,
(2S,3S)-3-(2,4-dichloro-phenyl)-1,1,1-trifluoro-2-(6-methyl-pyrazin-2-yl)-butan-2-ol,
(2R,3R)-3-(2,4-dichloro-phenyl)-1,1,1-trifluoro-2-(6-methyl-pyrazin-2-yl)-butan-2-ol,
3-(2-chloro-4-fluoro-phenyl)-2-(2-chloro-6-methoxy-pyridin-4-yl)-1,1,1-trifluoro-butan-2-ol,
3-(2,4-dichloro-phenyl)-1,1,1-trifluoro-2-(1-methyl-1H-pyrazol-4-yl)-butan-2-ol,
2-(2-chloro-6-methyl-pyridin-4-yl)-3-(2,4-dichloro-phenyl)-1,1,1-trifluoro-butan-2-ol,
3-(2,4-dichloro-phenyl)-1,1,1-trifluoro-2-quinolin-3-yl-butan-2-ol,
3-(2,4-dichloro-phenyl)-1,1,1-trifluoro-2-pyrimidin-4-yl-butan-2-ol,
3-(2,4-dichloro-phenyl)-1,1,1-trifluoro-2-(1-methyl-1H-imidazol-4-yl)-butan-2-ol,
4-[2-(2,4-dichloro-phenyl)-1-methoxy-1-trifluoromethyl-propyl]-pyridine,
3-(2,4-dichloro-phenyl)-1,1,1-trifluoro-2-pyrazolo[1,5-a]pyridin-2-yl-butan-2-ol,
3-(2,4-dichloro-phenyl)-1,1,1-trifluoro-2-(1-methyl-1H-pyrazol-3-yl)-butan-2-ol,
3-(2,4-dichloro-phenyl)-1,1,1-trifluoro-2-imidazo[1,2-a]pyridin-2-yl-butan-2-ol,
3-(2,4-dichloro-phenyl)-1,1,1-trifluoro-2-quinolin-6-yl-butan-2-ol,
3-(2,4-dichloro-phenyl)-1,1,1-trifluoro-2-quinoxalin-6-yl-butan-2-ol,
2-(2-benzyloxy-pyridin-4-yl)-3-(2,4-dichloro-phenyl)-1,1,1-trifluoro-butan-2-ol,
3-(2,4-dichloro-phenyl)-1,1,1-trifluoro-2-(6-methoxy-pyridin-3-yl)-butan-2-ol,
3-(2,4-dichloro-phenyl)-1,1,1-trifluoro-2-(5-methyl-1-phenyl-1H-pyrazol-4-yl)-butan-2-ol,
2-benzothiazol-6-yl-3-(2,4-dichloro-phenyl)-1,1,1-trifluoro-butan-2-ol,
3-(2,4-dichloro-phenyl)-1,1,1-trifluoro-2-quinoxalin-2-yl-butan-2-ol,
3-(2,4-dichloro-phenyl)-1,1,1-trifluoro-2-(2-pyridin-4-yl-thiazol-4-yl)-butan-2-ol,
3-(2,4-dichloro-phenyl)-1,1,1-trifluoro-2-thiazol-2-yl-butan-2-ol,
7-[2-(2,4-dichloro-phenyl)-1-hydroxy-1-trifluoromethyl-propyl]-3,4-dihydro-1H-isoquinoline-2-carboxylic acid tert-butyl ester,
3-(2,4-dichloro-phenyl)-1,1,1-trifluoro-2-pyrimidin-5-yl-butan-2-ol,
2-(1-benzyl-1H-pyrazol-4-yl)-3-(2,4-dichloro-phenyl)-1,1,1-trifluoro-butan-2-ol,
3-(2,4-dichloro-phenyl)-1,1,1-trifluoro-2-(4-methyl-3,4-dihydro-2H-pyrido[3,2-b][1,4]oxazin-7-yl)-butan-2-ol,
3-(2-chloro-4-fluoro-phenyl)-1,1,1-trifluoro-2-quinolin-3-yl-butan-2-ol,
3-(2-chloro-4-methoxy-phenyl)-1,1,1-trifluoro-2-quinoxalin-2-yl-butan-2-ol, 3-(2-chloro-4-fluoro-phenyl)-1,1,1-trifluoro-2-quinolin-6-yl-butan-2-ol,
3-(2,4-dichloro-phenyl)-1,1,1-trifluoro-2-(6-pyrrolidin-1-yl-pyridin-2-yl)-butan-2-ol,
3-(2-chloro-4-fluoro-phenyl)-1,1,1-trifluoro-2-(6-methyl-pyrazin-2-yl)-butan-2-ol,
(2S,3S)-3-(2,4-dichloro-phenyl)-1,1,1-trifluoro-2-quinolin-6-yl-butan-2-ol,
(2R,3R)-3-(2,4-dichloro-phenyl)-1,1,1-trifluoro-2-quinolin-6-yl-butan-2-ol,
3-chloro-4-[3,3,3-trifluoro-2-hydroxy-1-methyl-2-(5-methyl-pyrazin-2-yl)-propyl]-phenol,
3-chloro-4-[3,3,3-trifluoro-2-hydroxy-1-methyl-2-(2-methyl-pyridin-4-yl)-propyl]-phenol,
3-(4-benzyloxy-2-chloro-phenyl)-1,1,1-trifluoro-2-(2-methyl-pyridin-4-yl)-butan-2-ol,
{4-[2-(2,4-dichloro-phenyl)-1-hydroxy-1-trifluoromethyl-propyl]-pyridin-2-yloxy}-acetic acid,
4-chloro-3-[3,3,3-trifluoro-2-hydroxy-1-methyl-2-(6-methyl-pyrazin-2-yl)-propyl]-benzoic acid,
3-[2-chloro-4-(2-methoxy-ethoxy)-phenyl]-1,1,1-trifluoro-2-(2-methyl-pyridin-4-yl)-butan-2-ol,
{3-chloro-4-[3,3,3-trifluoro-2-hydroxy-1-methyl-2-(2-methyl-pyridin-4-yl)-propyl]-phenoxy}-acetic acid tert-butyl ester,
{3-chloro-4-[3,3,3-trifluoro-2-hydroxy-1-methyl-2-(2-methyl-pyridin-4-yl)-propyl]-phenoxy}-acetic acid,
2-{3-chloro-4-[3,3,3-trifluoro-2-hydroxy-1-methyl-2-(5-methyl-pyrazin-2-yl)-propyl]-phenoxy}-acetamide,
3-{2-chloro-4-[2-(2-methoxy-ethoxy)-ethoxy]-phenyl}-1,1,1-trifluoro-2-(5-methyl-pyrazin-2-yl)-butan-2-ol,
{3-chloro-4-[3,3,3-trifluoro-2-hydroxy-1-methyl-2-(5-methyl-pyrazin-2-yl)-propyl]-phenoxy}-acetic acid tert-butyl ester,
acetic acid 2-{3-chloro-4-[3,3,3-trifluoro-2-hydroxy-1-methyl-2-(5-methyl-pyrazin-2-yl)-propyl]-phenoxy}-ethyl ester,
(2-{3-chloro-4-[3,3,3-trifluoro-2-hydroxy-1-methyl-2-(5-methyl-pyrazin-2-yl)-propyl]-phenoxy}-ethyl)-carbamic acid tert-butyl ester,
3-[2-chloro-4-(2,2-difluoro-ethoxy)-phenyl]-1,1,1-trifluoro-2-(5-methyl-pyrazin-2-yl)-butan-2-ol,
3-[2-chloro-4-(2-methoxy-ethoxy)-phenyl]-1,1,1-trifluoro-2-(5-methyl-pyrazin-2-yl)-butan-2-ol,
3-[2-chloro-4-([1,2,4]oxadiazol-3-ylmethoxy)-phenyl]-1,1,1-trifluoro-2-(5-methyl-pyrazin-2-yl)-butan-2-ol,
3-[2-chloro-4-(5-methyl-isoxazol-3-ylmethoxy)-phenyl]-1,1,1-trifluoro-2-(5-methyl-pyrazin-2-yl)-butan-2-ol,
3-[2-chloro-4-(2-hydroxy-ethoxy)-phenyl]-1,1,1-trifluoro-2-(5-methyl-pyrazin-2-yl)-butan-2-ol,
3-[4-(2-amino-ethoxy)-2-chloro-phenyl]-1,1,1-trifluoro-2-(5-methyl-pyrazin-2-yl)-butan-2-ol,
3-[2-chloro-4-(1-methyl-1H-tetrazol-5-ylmethoxy)-phenyl]-1,1,1-trifluoro-2-(5-methyl-pyrazin-2-yl)-butan-2-ol,
3-[2-chloro-4-(3-methyl-[1,2,4]thiadiazol-5-ylmethoxy)-phenyl]-1,1,1-trifluoro-2-(5-methyl-pyrazin-2-yl)-butan-2-ol,
3-(2-chloro-4-fluoro-phenyl)-1,1,1-trifluoro-2-(2-methoxy-pyridin-4-yl)-butan-2-ol,
1,1,1-trifluoro-2-(5-methyl-pyrazin-2-yl)-3-naphthalen-1-yl-butan-2-ol,
2-(6-chloro-pyrazin-2-yl)-3-(2,4-dichloro-phenyl)-1,1,1-trifluoro-butan-2-ol,
3-(2,4-dichloro-phenyl)-1,1,1-trifluoro-2-isoquinolin-5-yl-butan-2-ol,
2-cinnolin-4-yl-3-(2,4-dichloro-phenyl)-1,1,1-trifluoro-butan-2-ol,
3-(2,4-dichloro-phenyl)-1,1,1-trifluoro-2-pyrazolo[1,5-a]pyridin-3-yl-butan-2-ol,
3-(2,4-dichloro-phenyl)-1,1,1-trifluoro-2-(1-phenethyl-1H-pyrazol-4-yl)-butan-2-ol,
2-(6-chloro-pyridin-3-yl)-3-(2,4-dichloro-phenyl)-1,1,1-trifluoro-butan-2-ol,
5-[2-(2,4-dichloro-phenyl)-1-hydroxy-1-trifluoromethyl-propyl]-pyridine-2-carbonitrile,
3-(2-chloro-4-phenethyloxy-phenyl)-1,1,1-trifluoro-2-(2-methyl-pyridin-4-yl)-butan-2-ol,
3-(2,4-dichloro-phenyl)-1,1,1-trifluoro-2-(2-methoxy-pyrimidin-5-yl)-butan-2-ol,
3-(2-chloro-4-methoxy-phenyl)-1,1,1-trifluoro-2-pyridin-4-yl-butan-2-ol,
3-chloro-4-(3,3,3-trifluoro-2-hydroxy-1-methyl-2-pyridin-4-yl-propyl)-phenol,
3-(2-chloro-4-methoxy-phenyl)-1,1,1-trifluoro-2-(3-isopropyl-3H-benzotriazol-5-yl)-butan-2-ol,
3-(2-chloro-4-methoxy-phenyl)-2-cinnolin-4-yl-1,1,1-trifluoro-butan-2-ol,
3-chloro-4-(2-cinnolin-4-yl-3,3,3-trifluoro-2-hydroxy-1-methyl-propyl)-phenol,
3-(2-chloro-4-methoxy-phenyl)-1,1,1-trifluoro-2-pyrazolo[1,5-a]pyridin-3-yl-butan-2-ol,
3-chloro-4-(3,3,3-trifluoro-2-hydroxy-1-methyl-2-pyrazolo[1,5-a]pyridin-3-yl-propyl)-phenol,
2-(2-chloro-pyridin-4-yl)-3-{2-chloro-4-[3-((1H)-tetrazol-5-yl)-propoxy]-phenyl}-1,1,1-trifluoro-butan-2-ol,
3-(2-chloro-4-hydroxymethyl-phenyl)-2-(2-chloro-pyridin-4-yl)-1,1,1-trifluoro-butan-2-ol,
{3-chloro-4-[2-(2-chloro-pyridin-4-yl)-3,3,3-trifluoro-2-hydroxy-1-methyl-propyl]-phenyl}-acetic acid,
3-{3-chloro-4-[2-(2-chloro-pyridin-4-yl)-3,3,3-trifluoro-2-hydroxy-1-methyl-propyl]-phenyl}-propionic acid,
3-(2-chloro-5-methoxy-phenyl)-2-(2-chloro-pyridin-4-yl)-1,1,1-trifluoro-butan-2-ol,
4-chloro-3-[2-(2-chloro-pyridin-4-yl)-3,3,3-trifluoro-2-hydroxy-1-methyl-propyl]-phenol,
3-(2,4-dichloro-phenyl)-5,5,5-trifluoro-4-hydroxy-4-(6-methyl-pyrazin-2-yl)-pentanoic acid methyl ester,
3-(2,4-dichloro-phenyl)-5,5,5-trifluoro-4-hydroxy-4-(6-methyl-pyrazin-2-yl)-pentanoic acid,
4-[2-(2,4-dichloro-phenyl)-1-hydroxy-1-trifluoromethyl-propyl]-1H-pyridin-2-one,
{4-[2-(2,4-dichloro-phenyl)-1-hydroxy-1-trifluoromethyl-propyl]-pyridin-2-yloxy}-acetic acid methyl ester,
{4-[2-(2,4-dichloro-phenyl)-1-hydroxy-1-trifluoromethyl-propyl]-2-oxo-2H-pyridin-1-yl}-acetic acid methyl ester,
{4-[2-(2,4-dichloro-phenyl)-1-hydroxy-1-trifluoromethyl-propyl]-2-oxo-2H-pyridin-1-yl}-acetic acid,
2-{4-[2-(2,4-dichloro-phenyl)-1-hydroxy-1-trifluoromethyl-propyl]-pyridin-2-yloxy}-acetamide,
3-(2,4-dichloro-phenyl)-1,1,1-trifluoro-2-[2-(2-methoxy-ethoxy)-pyridin-4-yl]-butan-2-ol,
{4-[2-(2,4-dichloro-phenyl)-1-hydroxy-1-trifluoromethyl-propyl]-pyridin-2-yloxy}-acetonitrile,
3-(2,4-dichloro-phenyl)-1,1,1-trifluoro-2-[2-(2-hydroxy-ethoxy)-pyridin-4-yl]-butan-2-ol,
2-{4-[2-(2,4-dichloro-phenyl)-1-hydroxy-1-trifluoromethyl-propyl]-pyridin-2-yloxy}-1-morpholin-4-yl-ethanone,
4-[2-(2,4-dichloro-phenyl)-4,4,4-trifluoro-3-hydroxy-3-(6-methyl-pyrazin-2-yl)-butyl]-benzoic acid ethyl ester,
4-[2-(2,4-dichloro-phenyl)-4,4,4-trifluoro-3-hydroxy-3-(6-methyl-pyrazin-2-yl)-butyl]-benzoic acid,
4-chloro-3-[3,3,3-trifluoro-2-hydroxy-1-methyl-2-(6-methyl-pyrazin-2-yl)-propyl]-benzoic acid methyl ester, 3-(2-chloro-4-methoxy-phenyl)-2-(2-chloro-pyridin-4-yl)-1,1,1-trifluoro-butan-2-ol,
3-chloro-4-[2-(2-chloro-pyridin-4-yl)-3,3,3-trifluoro-2-hydroxy-1-methyl-propyl]-phenol,
2-{3-chloro-4-[2-(2-chloro-pyridin-4-yl)-3,3,3-trifluoro-2-hydroxy-1-methyl-propyl]-phenoxy}-2-methyl-propionamide,
3-chloro-4-[2-(2-chloro-pyridin-4-yl)-3,3,3-trifluoro-2-hydroxy-1-methyl-propyl]-benzoic acid methyl ester,
4-[2-(2-chloro-4-methoxycarbonyl-phenyl)-1-hydroxy-1-trifluoromethyl-propyl]-pyridine-2-carboxylic acid methyl ester,
3-chloro-4-[2-(2-chloro-pyridin-4-yl)-3,3,3-trifluoro-2-hydroxy-1-methyl-propyl]-benzoic acid,
4-[2-(4-carboxy-2-chloro-phenyl)-1-hydroxy-1-trifluoromethyl-propyl]-pyridine-2-carboxylic acid,
3-(2-chloro-4-methoxy-phenyl)-1,1,1-trifluoro-2-(2-iodo-pyridin-4-yl)-butan-2-ol,
4-{4-[2-(2-chloro-4-methoxy-phenyl)-1-hydroxy-1-trifluoromethyl-propyl]-pyridin-2-yl}-benzoic acid ethyl ester,
4-{4-[2-(2-chloro-4-methoxy-phenyl)-1-hydroxy-1-trifluoromethyl-propyl]-pyridin-2-yl}-benzoic acid,
3-{4-[2-(2-chloro-4-methoxy-phenyl)-1-hydroxy-1-trifluoromethyl-propyl]-pyridin-2-yl}-benzoic acid methyl ester,
3-{4-[2-(2-chloro-4-methoxy-phenyl)-1-hydroxy-1-trifluoromethyl-propyl]-pyridin-2-yl}-benzoic acid,
3-(2-chloro-4-fluoro-phenyl)-1,1,1-trifluoro-2-(2-iodo-pyridin-4-yl)-butan-2-ol,
3-{4-[2-(2-chloro-4-fluoro-phenyl)-1-hydroxy-1-trifluoromethyl-propyl]-pyridin-2-yl}-benzoic acid methyl ester,
5-{4-[2-(2-chloro-4-fluoro-phenyl)-1-hydroxy-1-trifluoromethyl-propyl]-pyridin-2-yl}-2-fluoro-benzonitrile,
3-{4-[2-(2-chloro-4-fluoro-phenyl)-1-hydroxy-1-trifluoromethyl-propyl]-pyridin-2-yl}-benzoic acid,
4'-[2-(2-chloro-4-trifluoromethanesulfonyloxy-phenyl)-1-hydroxy-1-trifluoromethyl-propyl]-3,4,5,6-tetrahydro-2H-[1,2']bipyridinyl-4-carboxylic acid ethyl ester,
4'-[2-(2-chloro-4-hydroxy-phenyl)-1-hydroxy-1-trifluoromethyl-propyl]-3,4,5,6-tetrahydro-2H-[1,2']bipyridinyl-4-carboxylic acid,
2-chloro-5-{4-[2-(2-chloro-4-fluoro-phenyl)-1-hydroxy-1-trifluoromethyl-propyl]-pyridin-2-yl}-benzoic acid ethyl ester,
5-{4-[2-(2-chloro-4-fluoro-phenyl)-1-hydroxy-1-trifluoromethyl-propyl]-pyridin-2-yl}-2-fluoro-benzoic acid ethyl ester,
5-{4-[2-(2-chloro-4-fluoro-phenyl)-1-hydroxy-1-trifluoromethyl-propyl]-pyridin-2-yl}-2-fluoro-benzoic acid,
2-chloro-5-{4-[2-(2-chloro-4-fluoro-phenyl)-1-hydroxy-1-trifluoromethyl-propyl]-pyridin-2-yl}-benzoic acid,
4'-[2-(2-chloro-4-methoxy-phenyl)-1-hydroxy-1-trifluoromethyl-propyl]-3,4,5,6-tetrahydro-2H-[1,2']bipyridinyl-4-carboxylic acid ethyl ester,
4'-[2-(2-chloro-4-methoxy-phenyl)-1-hydroxy-1-trifluoromethyl-propyl]-3,4,5,6-tetrahydro-2H[1,2']bipyridinyl-4-carboxylic acid,
4'-[2-(2-chloro-4-ethoxy-phenyl)-1-hydroxy-1-trifluoromethyl-propyl]-3,4,5,6-tetrahydro-2H-[1,2']bipyridinyl-4-carboxylic acid,
1,1,1-trifluoro-3-(6-methoxy-4-methyl-pyridin-3-yl)-2-pyridin-4-yl-butan-2-ol,
1,1,1-trifluoro-2-pyridin-4-yl-3-quinolin-3-yl-butan-2-ol,
3-(3,4-dichloro-phenyl)-1,1,1-trifluoro-2-pyridin-4-yl-butan-2-ol,
1,1,1-trifluoro-3-(4-methoxy-phenyl)-2-pyridin-4-yl-butan-2-ol,
1,1,1-trifluoro-3-(4-methoxy-2-methyl-phenyl)-2-pyridin-4-yl-butan-2-ol,
3-(2,4-difluoro-phenyl)-1,1,1-trifluoro-2-pyridin-4-yl-butan-2-ol,
1,1,1-trifluoro-3-(2-methoxy-naphthalen-1-yl)-2-pyridin-4-yl-butan-2-ol,
1,1,1-trifluoro-3-naphthalen-2-yl-2-pyridin-4-yl-butan-2-ol,
3-(2-chloro-4-diallylamino-phenyl)-2-(2-chloro-pyridin-4-yl)-1,1,1-trifluoro-butan-2-ol,
N-{3-chloro-4-[2-(2-chloro-pyridin-4-yl)-3,3,3-trifluoro-2-hydroxy-1-methyl-propyl]-phenyl}-methanesulfonamide,
N-{3-chloro-4-[2-(2-chloro-pyridin-4-yl)-3,3,3-trifluoro-2-hydroxy-1-methyl-propyl]-phenyl}-benzamide,
3-(2-chloro-4-fluoro-phenyl)-2-(6-chloro-pyridin-3-yl)-1,1,1-trifluoro-butan-2-ol,
5-[2-(2-chloro-4-fluoro-phenyl)-1-hydroxy-1-trifluoromethyl-propyl]-pyridine-2-carboxylic acid,
4-[2-(2-chloro-4-fluoro-phenyl)-1-hydroxy-1-trifluoromethyl-propyl]-pyridine-2-carboxylic acid,
3-(4-bromo-2-chloro-phenyl)-1,1,1-trifluoro-2-(2-methyl-pyridin-4-yl)-butan-2-ol,
1-[1-(4-chloro-phenyl)-cyclopropyl]-2,2,2-trifluoro-1-quinolin-3-yl-ethanol,
1-[1-(2,4-dichloro-phenyl)-cyclopropyl]-2,2,2-trifluoro-1-quinolin-3-yl-ethanol,
1-(2-chloro-pyridin-4-yl)-1-[1-(2,4-dichloro-phenyl)-cyclopropyl]-2,2,2-trifluoro-ethanol,
2-(2-chloro-pyridin-4-yl)-3-(2,4-dichloro-phenyl)-1,1,1-trifluoro-3-methyl-butan-2-ol,
3-(4-chloro-phenyl)-1,1,1-trifluoro-3-methyl-2-(2-methyl-pyridin-4-yl)-butan-2-ol,
3-(2,6-dichloro-pyridin-3-yl)-1,1,1-trifluoro-2-(5-methyl-pyrazin-2-yl)-butan-2-ol,
3-(2-chloro-4-methoxy-phenyl)-1,1,1-trifluoro-2-quinolin-3-yl-butan-2-ol,
3-chloro-4-(3,3,3-trifluoro-2-hydroxy-1-methyl-2-quinolin-3-yl-propyl)-phenol,
3-[2-chloro-4-(4-methanesulfonyl-benzyloxy)-phenyl]-1,1,1-trifluoro-2-quinolin-3-yl-butan-2-ol,
benzenesulfonic acid 3-chloro-4-(3,3,3-trifluoro-2-hydroxy-1-methyl-2-quinolin-3-yl-propyl)-phenyl ester,
3-(2-chloro-4-methoxy-phenyl)-1,1,1-trifluoro-2-isoquinolin-5-yl-butan-2-ol,
3-chloro-4-(3,3,3-trifluoro-2-hydroxy-isoquinolin-5-yl-1-methyl-propyl)-phenol,
3-[2-(2-chloro-4-methoxy-phenyl)-1-hydroxy-1-trifluoromethyl-propyl]-quinoline-6-carbonitrile,
3-(2,4-dichloro-phenyl)-1,1,1-trifluoro-2-(5-fluoro-1H-indol-3-yl)-butan-2-ol,
3-(2,4-dichloro-phenyl)-1,1,1-trifluoro-2-(1-phenyl-1H-indazol-5-yl)-butan-2-ol,
3-(2,4-dichloro-phenyl)-1,1,1-trifluoro-2-[1-(3-methoxy-phenyl)-1H-indazol-5-yl]-butan-2-ol,
3-{5-[2-(2,4-dichloro-phenyl)-1-hydroxy-1-trifluoromethyl-propyl]-indazol-1-yl}-phenol,
3-(2,4-dichloro-phenyl)-1,1,1-trifluoro-2-[1-(2-methoxy-phenyl)-1H-indazol-5-yl]-butan-2-ol,
2-{5-[2-(2,4-dichloro-phenyl)-1-hydroxy-1-trifluoromethyl-propyl]-indazol-1-yl}-phenol,
3-(2,4-dichloro-phenyl)-1,1,1-trifluoro-2-[1-(4-methoxy-phenyl)-1H-indazol-5-yl]-butan-2-ol,
4-{5-[2-(2,4-dichloro-phenyl)-1-hydroxy-1-trifluoromethyl-propyl]-indazol-1-yl}-phenol,
3-(2-chloro-4-methoxy-phenyl)-1,1,1-trifluoro-2-(6-methoxy-pyridin-3-yl)-butan-2-ol, 5-[2-(2-chloro-4-methoxy-phenyl)-1-hydroxy-1-trifluoromethyl-propyl]-1H-pyridin-2-one,
5-[2-(2-chloro-4-methoxy-phenyl)-1-hydroxy-1-trifluoromethyl-propyl]-1-methyl-1H-pyridin-2-one,
5-[2-(2-chloro-4-hydroxy-phenyl)-1-hydroxy-1-trifluoromethyl-propyl]-1-methyl-1H-pyridin-2-one,
4-{3-chloro-4-[3,3,3-trifluoro-2-hydroxy-1-methyl-2-(1-methyl-6-oxo-1,6-dihydro-pyridin-3-yl)-propyl]-phenoxy}-3-fluoro-benzonitrile,
3-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzonitrile,
5-{2-[2-chloro-4-(4-fluoro-3-methoxy-phenoxy)-phenyl]-1-hydroxy-1-trifluoromethyl-propyl}-1-methyl-1H-pyridin-2-one,
5-{2-[2-chloro-4-(4-fluoro-3-hydroxy-phenoxy)-phenyl]-1-hydroxy-1-trifluoromethyl-propyl}-1-methyl-1H-pyridin-2-one,
5-[2-(2,4-dichloro-phenyl)-1-hydroxy-1-trifluoromethyl-propyl]-1-methyl-1H-pyridin-2-one,
5-[2-(2,4-dichloro-phenyl)-1-hydroxy-1-trifluoromethyl-propyl]-1-ethyl-1H-pyridin-2-one,
5-[2-(4-bromo-2-chloro-phenyl)-1-hydroxy-1-trifluoromethyl-propyl]-1-methyl-1H-pyridin-2-one,
3-(4-bromo-2-chloro-phenyl)-1,1,1-trifluoro-2-(6-methoxy-pyridin-3-yl)-butan-2-ol,
5-[2-(4-bromo-2-chloro-phenyl)-1-hydroxy-1-trifluoromethyl-propyl]-1H-pyridin-2-one,
5-[2-(4-bromo-2-chloro-phenyl)-1-hydroxy-1-trifluoromethyl-propyl]-1-ethyl-1H-pyridin-2-one,
5-[2-(2-chloro-5-methoxy-phenyl)-1-hydroxy-1-trifluoromethyl-propyl]-1-methyl-1H-pyridin-2-one,
5-[2-(2,3-dichloro-4-methoxy-phenyl)-1-hydroxy-1-trifluoromethyl-propyl]-1-methyl-1H-pyridin-2-one,
5-[2-(2,3-dichloro-4-hydroxy-phenyl)-1-hydroxy-1-trifluoromethyl-propyl]-1-methyl-1H-pyridin-2-one,
5-[2-(2-chloro-5-fluoro-4-methoxy-phenyl)-1-hydroxy-1-trifluoromethyl-propyl]-1-methyl-1 H-pyridin-2-one,
and pharmaceutically acceptable salts thereof.

Especially preferred compounds of formula I of the present invention are the following:
3-(2-chloro-4-methoxy-phenyl)-1,1,1-trifluoro-2-(5-methyl-pyrazin-2-yl)-butan-2-ol,
3-(2-chloro-4-methoxy-phenyl)-1,1,1-trifluoro-2-(2-methyl-pyridin-4-yl)-butan-2-ol,
3-(2-chloro-4-ethoxy-phenyl)-1,1,1-trifluoro-2-(2-methyl-pyridin-4-yl)-pentan-2-ol,
3-(2-chloro-4-propoxy-phenyl)-1,1,1-trifluoro-2-(2-methyl-pyridin-4-yl)-hexan-2-ol,
3-(2,4-dichloro-phenyl)-1,1,1-trifluoro-2-(2-methyl-pyridin-4-yl)-butan-2-ol,
3-(2,4-dichloro-phenyl)-1,1,1-trifluoro-2-(2-methoxy-pyridin-4-yl)-butan-2-ol,
3-(2-chloro-4-fluoro-phenyl)-2-(2-chloro-6-methoxy-pyridin-4-yl)-1,1,1-trifluoro-butan-2-ol,
2-(2-chloro-6-methyl-pyridin-4-yl)-3-(2,4-dichloro-phenyl)-1,1,1-trifluoro-butan-2-ol,
3-(2,4-dichloro-phenyl)-1,1,1-trifluoro-2-quinolin-3-yl-butan-2-ol,
3-(2,4-dichloro-phenyl)-1,1,1-trifluoro-2-pyrazolo[1,5-a]pyridin-2-yl-butan-2-ol,
3-(2,4-dichloro-phenyl)-1,1,1-trifluoro-2-quinolin-6-yl-butan-2-ol,
3-(2,4-dichloro-phenyl)-1,1,1-trifluoro-2-quinoxalin-6-yl-butan-2-ol,
2-benzothiazol-6-yl-3-(2,4-dichloro-phenyl)-1,1,1-trifluoro-butan-2-ol,
3-(2-chloro-4-methoxy-phenyl)-1,1,1-trifluoro-2-quinoxalin-2-yl-butan-2-ol,
3-(4-benzyloxy-2-chloro-phenyl)-1,1,1-trifluoro-2-(2-methyl-pyridin-4-yl)-butan-2-ol,
and pharmaceutically acceptable salts thereof.

Furthermore, the following compounds of formula I are especially preferred:
3-[2-chloro-4-(5-methyl-isoxazol-3-ylmethoxy)-phenyl]-1,1,1-trifluoro-2-(5-methyl-pyrazin-2-yl)-butan-2-ol,
3-(2,4-dichloro-phenyl)-1,1,1-trifluoro-2-isoquinolin-5-yl-butan-2-ol,
2-cinnolin-4-yl-3-(2,4-dichloro-phenyl)-1,1,1-trifluoro-butan-2-ol,
3-(2,4-dichloro-phenyl)-1,1,1-trifluoro-2-pyrazolo[1,5-a]pyridin-3-yl-butan-2-ol,
2-(6-chloro-pyridin-3-yl)-3-(2,4-dichloro-phenyl)-1,1,1-trifluoro-butan-2-ol,
3-(2-chloro-4-phenethyloxy-phenyl)-1,1,1-trifluoro-2-(2-methyl-pyridin-4-yl)-butan-2-ol,
3-(2-chloro-4-methoxy-phenyl)-2-cinnolin-4-yl-1,1,1-trifluoro-butan-2-ol,
3-(2-chloro-4-methoxy-phenyl)-1,1,1-trifluoro-2-pyrazolo[1,5-a]pyridin-3-yl-butan-2-ol,
3-(2-chloro-4-hydroxymethyl-phenyl)-2-(2-chloro-pyridin-4-yl)-1,1,1-trifluoro-butan-2-ol,
3-(2-chloro-5-methoxy-phenyl)-2-(2-chloro-pyridin-4-yl)-1,1,1-trifluoro-butan-2-ol,
{4-[2-(2,4-dichloro-phenyl)-1-hydroxy-1-trifluoromethyl-propyl]-pyridin-2-yloxy}-acetonitrile,
3-(2-chloro-4-methoxy-phenyl)-2-(2-chloro-pyridin-4-yl)-1,1,1-trifluoro-butan-2-ol,
3-chloro-4-[2-(2-chloro-pyridin-4-yl)-3,3,3-trifluoro-2-hydroxy-1-methyl-propyl]-benzoic acid methyl ester,
3-(2-chloro-4-methoxy-phenyl)-1,1,1-trifluoro-2-(2-iodo-pyridin-4-yl)-butan-2-ol,
3-(2-chloro-4-fluoro-phenyl)-1,1,1-trifluoro-2-(2-iodo-pyridin-4-yl)-butan-2-ol,
3-(2-chloro-4-diallylamino-phenyl)-2-(2-chloro-pyridin-4-yl)-1,1,1-trifluoro-butan-2-ol,
3-(2-chloro-4-fluoro-phenyl)-2-(6-chloro-pyridin-3-yl)-1,1,1-trifluoro-butan-2-ol,
3-(4-bromo-2-chloro-phenyl)-1,1,1-trifluoro-2-(2-methyl-pyridin-4-yl)-butan-2-ol,
3-(2-chloro-4-methoxy-phenyl)-1,1,1-trifluoro-2-quinolin-3-yl-butan-2-ol,
3-(2-chloro-4-methoxy-phenyl)-1,1,1-trifluoro-2-isoquinolin-5-yl-butan-2-ol,
3-chloro-4-(3,3,3-trifluoro-2-hydroxy-2-isoquinolin-5-yl-1-methyl-propyl)-phenol,
3-[2-(2-chloro-4-methoxy-phenyl)-1-hydroxy-1-trifluoromethyl-propyl]-quinoline-6-carbonitrile,
4-{3-chloro-4-[3,3,3-trifluoro-2-hydroxy-1-methyl-2-(1-methyl-6-oxo-1,6-dihydro-pyridin-3-yl)-propyl]-phenoxy}-3-fluoro-benzonitrile,
5-[2-(4-bromo-2-chloro-phenyl)-1-hydroxy-1-trifluoromethyl-propyl]-1-methyl-1H-pyridin-2-one,
5-[2-(4-bromo-2-chloro-phenyl)-1-hydroxy-1-trifluoromethyl-propyl]-1-ethyl-1H-pyridin-2-one,
and pharmaceutically acceptable salts thereof.

Furthermore, the pharmaceutically acceptable salts of the compounds of formula I constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises treating a compound of the formula II

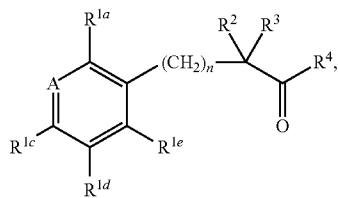

wherein A, n, $R^{1a}$ to $R^{1e}$, $R^2$, $R^3$ and $R^4$ are as defined herein before, with trifluoromethyltrimethylsilane and a suitable fluoride, to obtain a compound of the formula Ia

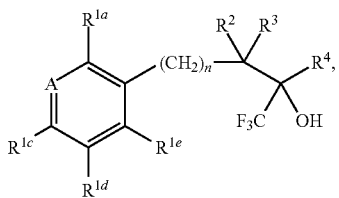

and, if desired, alkylating the compound of formula Ia with methyliodide in the presence of a base such as NaH to obtain a compound of formula Ib

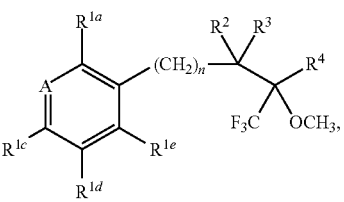

and, if desired, converting the compound obtained into a pharmaceutically acceptable salt.

The compounds of formula I can be manufactured by the methods given below, by the methods given in the examples or by analogous methods. Appropriate reaction conditions for the individual reaction steps are known to a person skilled in the art.

The synthesis of compounds with the general structure I is described in scheme 1.

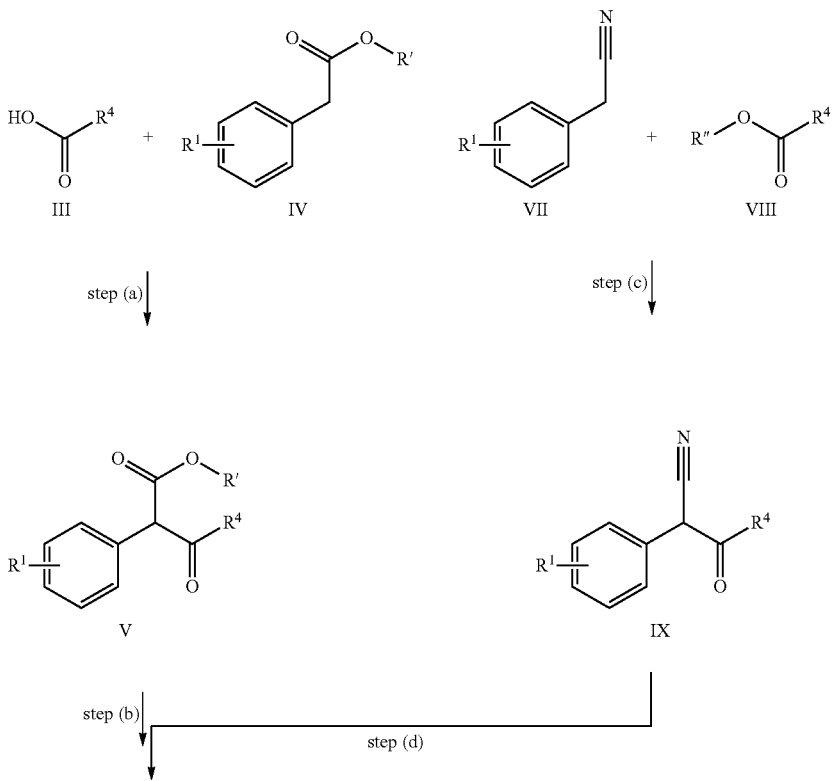

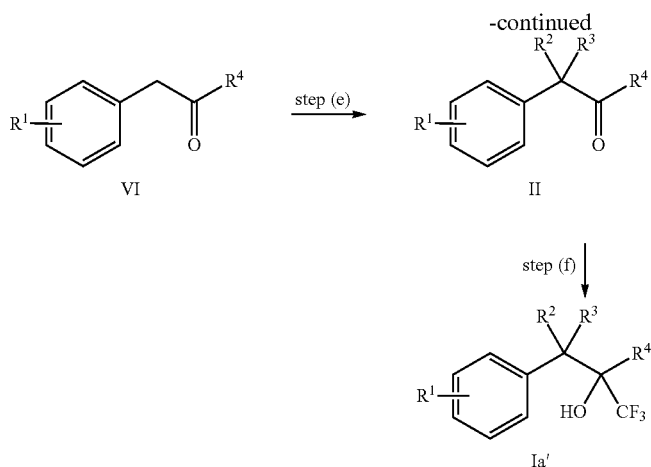

$R^4$ is a heteroaryl ring as defined herein before; $R^1$ corresponds to $R^{1a}$ to $R^{1e}$ as defined herein before; $R^2$ and $R^3$ are as defined herein before, R' is typically methyl or ethyl.

A heteroaryl carboxylic acid III is suitably activated, e.g. by reaction with 1,1'-carbonyldiimidazole (CDI), and reacted with a phenyl-acetic acid ester IV, which is deprotonated in situ by a suitable base, such as NaH, to give the compound of formula V (step a). The reaction is carried out at a temperature of $-10°$ C. to $0°$ C. in a suitable solvent such as DMF. Compound V is then saponified and decarboxylated, e.g. by heating of V in a mixture of DMSO, water and NaCl to a temperature of $140°$ C. to give the ketone VI (step b).

Alternatively, ketone VI can be obtained as outlined via steps (c) and (d): A phenyl-acetonitrile VII is deprotonated by a suitable base, such as potassium tert-pentylate, in suitable solvent such as THF and reacted with a heteroarylcarboxylic acid ester VIII to give a compound of formula IX (step c). The nitrile of formula IX is then saponified and decarboxylated, e.g. by heating a mixture of IX with concentrated hydrobromic acid to reflux followed by addition of a base such as $NaHCO_3$, to give the ketone of formula VI (step d).

Compound VI is then deprotonated by a base, such as NaH, in a suitable solvent such as DMF, and the resulting anion is reacted with an alkylating agent, such as methyl iodide, to give the alpha substituted ketone of formula II (e). In a final step (f), the ketone of formula II is converted to a compound of formula Ia', wherein $R^5$ is hydrogen, typically by treatment with trifluoromethyltrimethylsilane and a suitable fluoride, such as tetrabutylammonium fluoride, at a temperature of $0°$ C. Compounds of formula I, wherein $R^5$ is methyl, can be obtained form compounds of formula Ia' by O-methylation with the help of a base such as NaH and methyliodide in a suitable solvent such as dimethylformamide.

Alternatively, suitably substituted ketone precursors of formula II can be made available using alternative routes. One additional approach is based on addition of a metallated intermediate M-$R^4$ to a suitably substituted aldehyde as a key step. This route is outlined in scheme 2.

Scheme 2

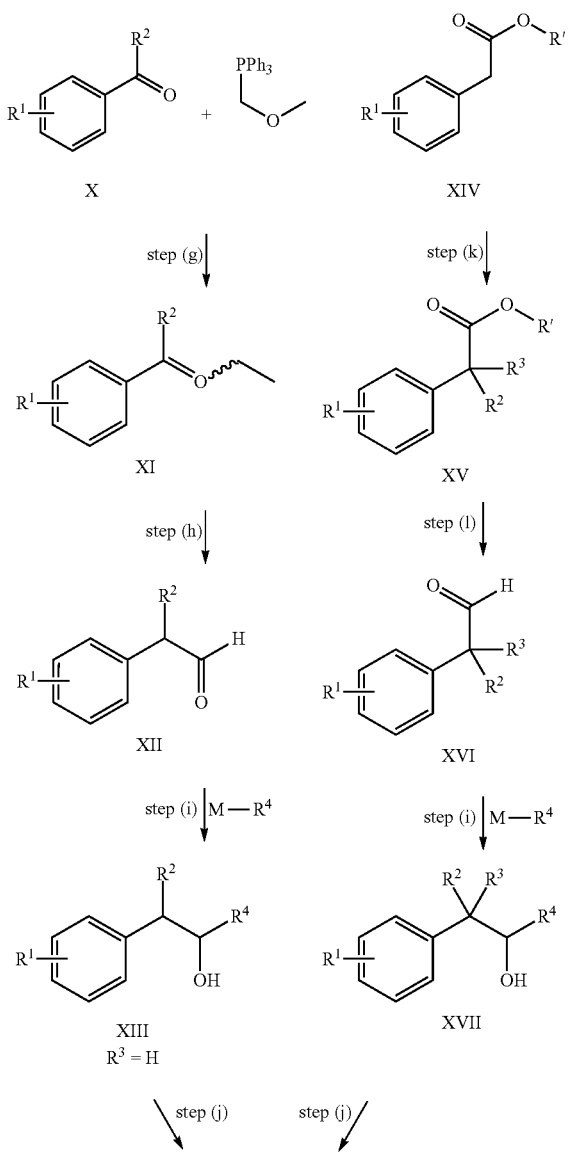

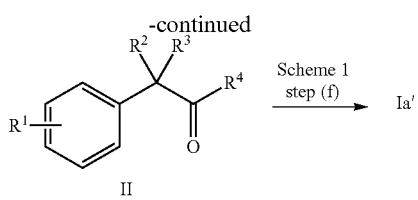

Aldehydes of formula XII and XVI are key intermediates in that approach. Monosubstituted aldehydes of formula XII are conveniently made from aryl ketones of formula X, e.g. by treatment with a suitable Wittig reagent such as methoxymethyl-triphenyl-λ5-phosphane and a base such as NaH, LDA, BuLi or the like (step (g)) to give enol ether intermediates of formula XI which are conveniently hydrolyzed under acidic conditions (step (h)) with aq. HCl, $H_2SO_4$ or other acids to provide monosubstituted aldehydes of formula XII.

Alternatively, mono- or disubstituted aldehydes of formula XVI are accessible via alkylation of a suitably substituted arylacetic acid ester XIV (step (k)) under similar conditions that have been outlined above in scheme 1, step (e) to give suitably substituted intermediates of formula XV. Esters of formula XV can be reduced to aldehydes of formula XVI e.g. by treatment with reducing agents such as DIBAH, SMEAH or the like (step (l)) or, alternatively, by reduction to the alcohol and subsequent re-oxidation (not shown in scheme 2).

Aldehydes of formula XII or XVI can be treated with suitable nucleophiles M-$R^4$ to give secondary alcohols of formula XIII and XVII, respectively (step (i)). The nucleophile M-$R^4$ can be generated for example from suitable aryl or heteroaryl halides by treatment with e.g. BuLi or isopropylmagnesiumchloride or the like to affect a halogen metal exchange.

Subsequent oxidation of alcohols of formula XIII or XVII, respectively (step (j)) with e.g. TPAP, NMO or Dess-Martin periodinane or under Swern conditions or the like will provide ketone intermediates of formula II which are further converted to the desired products of formula Ia' as outlined in scheme 1, step (f).

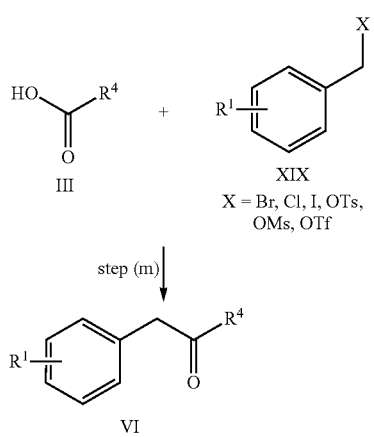

An alternative synthesis of ketone precursors VI is described in Scheme 3: A carboxylic acid III is suitably activated, e.g. by transformation to the acid chloride or to the Weinreb amide and reacted with a tolyl derivative XIX containing a leaving group such as Br, Cl, I, OTs, OMs, OTf in the presence of a metal such as zinc, magnesium or manganese or a metal derivative such as n-butyllithium, optionally in the presence of a catalyst such as tetrakis(triphenylphosphine)palladium(0) in a suitable solvent such as 1,2-dimethoxyethane or tetrahydrofuran at temperatures of –78° C. to room temperature. Ketones VI can then be transformed to compounds of formula I by the methods outlined in Scheme 1, steps e and f.

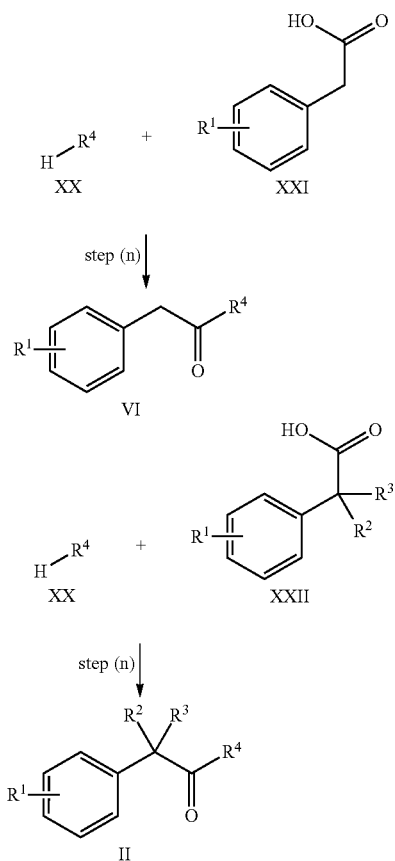

Another method for the synthesis of ketone precursors VI and II is described in Scheme 4: A phenylacetic acid XXI or an alpha substituted phenylacetic acid XXII is suitably activated e.g. by transformation to the acid chloride and reacted with a heteroaryl compound XX in the presence of a Lewis acid, e.g. $AlCl_3$, or $ZnCl_2$ in a suitable solvent such as 1,2-dichloroethane or $CS_2$ at temperatures from –10° C. to reflux of the solvent to give in a Friedel-Crafts acylation reaction ketones VI or II.

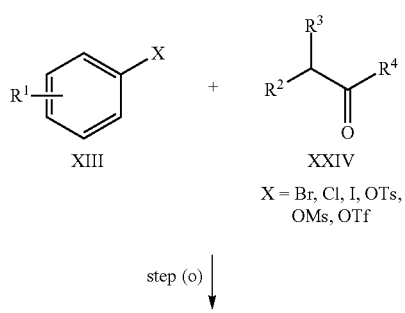

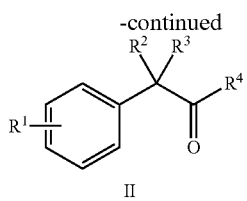

II

An alternative synthesis of ketone precursor II is described in Scheme 5: A ketone derivative XXIV is arylated with an aryl or heteroaryl halide or activated phenol derivative such as triflate, mesylate or tosylate XXIII in a suitable solvent such as toluene, THF or dioxane at temperatures preferably from room temperature to reflux of the solvent or above reflux of the solvent under pressure. The reaction requires the addition of a suitable base such as caesium carbonate, potassium phosphate or alkali alkoholates and a suitable catalyst such as chloro(di-2-norbornylphosphino)(2-dimethylamino-methyl-ferrocen-1-yl)palladium (II) (CAS Reg. No. 614753-51-4), described in *Pharm Chem* 2004, 3, 29, catalysts described by S. Buchwald such as in *J. Am. Chem. Soc.* 1997, 119, 11108, catalysts described by J. Hartwig such as in *J. Am. Chem. Soc.* 1999, 121, 1473, and suitable catalysts described by others skilled in the art.

All starting materials are either commercially available, have been described in the literature, or can be prepared by methods well known in the art.

Compounds of formula I contain stereocenters and can optionally be separated into optically pure enantiomers or diastereomers by methods well known in the art, e.g. by chromatography on a chiral HPLC column.

As described above, the compounds of formula I of the present invention can be used as medicaments for the treatment and/or prevention of diseases which are associated with glucocorticoid receptor (GR) modulation.

In this context, the expression 'diseases which are associated with glucocorticoid receptor (GR) modulation' means diseases which can be treated and/or prevented by glucocorticoid receptor (GR) modulation, i.e. preferably by treatment with a glucocorticoid receptor antagonist. Such diseases encompass, but are not limited to, diabetes, preferably type 2 diabetes, dyslipidemia, obesity, metabolic syndrome, hypertension, adrenal imbalance, cardiovascular diseases, Cushing's syndrome, stress-related immunosuppression and neurological disorders such as depression.

In a preferable aspect, the expression 'diseases which are associated with glucocorticoid receptor modulation' relates to diabetes, preferably type 2 diabetes, dyslipidemia, obesity, hypertension, adrenal imbalance, cardiovascular diseases and depression. More preferably, the expression 'diseases which are associated with glucocorticoid receptor modulation' relates to diabetes, preferably type 2 diabetes.

Exceptionally, the compounds of the present invention can also be useful in treating immune, autoimmune and inflammatory diseases when they are selectively activating the glucocorticoid receptor.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with glucocorticoid receptor modulation.

In another embodiment, the invention relates to a method for the treatment and/or prevention of diseases which are associated with glucocorticoid receptor modulation, which method comprises administering a therapeutically active amount of a compound of formula I to a human being or animal. A method for the treatment and/or prevention of diabetes is preferred.

The invention further relates to the use of compounds of formula I as defined above for the treatment and/or prevention of diseases which are associated with glucocorticoid receptor modulation.

In addition, the invention relates to the use of compounds of formula I as defined above for the preparation of medicaments for the treatment and/or prevention of diseases which are associated with glucocorticoid receptor modulation. The use of compounds of formula I as defined above for the preparation of medicaments for the treatment and/or prevention of diabetes is preferred.

The compounds of the present invention can also be used in combination therapy with other antidiabetic drugs. Suitable antidiabetic drugs for use in combination with the compounds of the present invention include, but are not limited to insulin and insulin analogs (e.g. LysPro insulin, inhaled formulations comprising insulin); sulfonylureas and analogs (e.g. chlorpropamide, glibenclamide, tolbutamide, tolazamide, acetohexamide, glypizide, glyburide, glimepiride); biguanides (e.g. metformin hydrochloride, phenformin, buformin); alpha-glucosidase inhibitors (acarbose, epalrestat, miglitol, voglibose), alpha2-antagonists and imidazolines (e.g. midaglizole, isaglidole, deriglidole, idazoxan, efaroxan, fluparoxan); thiazolidinediones and PPAR-gamma agonists (e.g. ciglitazone, pioglitazone hydrochloride, troglitazone, rosiglitazone maleate, balaglitazone); PPAR-alpha agonists (e.g. fenofibrate, gemfibrozil); PPAR alpha/gamma dual agonists (e.g. muraglitazar, aleglitazar, peliglitazar); dipeptidyl peptidase-IV (DPP-4) inhibitors (e.g. saxagliptin, sitagliptin, vildagliptin, alogliptin and denagliptin); glucagon like peptide-1 (GLP-1) receptor agonists (e.g. Exenatide (Byetta™), NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™); insulin secretagogues (e.g. linogliride, nateglinide, repaglinide, mitiglinide calcium hydrate, meglitinide); SGLT-2 inhibitors (e.g. dapagliflozin (BMS), sergliflozin (Kissei), AVE 2268 (Sanofi-Aventis)); Angiotensin AT1 antagonists (e.g. irbesartan, valsartan); amylin agonists (e.g. pramlintide, AC-137) and Glucokinase activators such as the compounds disclosed in e.g. WO 00/58293 A1.

As described above, the compounds of formula I and their pharmaceutically acceptable salts possess valuable pharmacological properties. Specifically, it has been found that compounds of the present invention are excellent glucocorticoid receptor antagonists.

The following tests were carried out in order to determine the activity of the compounds of formula I.

Glucocorticoid Receptor Binding Assay

The ability of the substances to bind to the glucocorticoid receptor was determined with the help of a commercial Glucocorticoid Receptor Competitor Assay far red kit provided by Panvera/Invitrogen (PV4302). This kit is used as provided by the supplier. It contains some partially purified full length human recombinant glucocorticoid receptor, a coactivator related GR stabilizing peptide, a tight-binding fluorescent GR ligand Fluormone™ GS Far Red as labeled tracer and a screening buffer. All reagents are prepared and the assay is run according to the recommendations of the kit manufacturer.

Briefly, the GR stabilizing peptide and the human recombinant glucocorticoid receptor are both diluted with the screening buffer (pH 7.4) and are gently mixed (no vortexing) just before the assay and kept on ice until use. The fluorescent-labeled ligand is also diluted with the screening buffer just before the assay and kept on ice until use. The substances to test are pre-diluted in pure DMSO then some water is added to get an intermediate 4.2% DMSO stock solution. Ten microliter of the intermediate stock solution is gently mixed with 5 l of diluted fluorescent-labeled ligand and 5 l of diluted human recombinant glucocorticoid receptor in a 384-well plate (low volume, ultraclear, glass plate from Greiner ref 788896). The plate is centrifuged, sealed and incubated for 3 hours at 22° C. in the dark. The polarized fluorescence is measured with a Zeiss-HTS reader or any equivalent equipment (610-660 nm).

All compounds were tested to determine $IC_{50}$ in a serial dilution experiment. The concentration at which 50% inhibition of the fluorescent GR ligand Fluormone™ GS Far Red is obtained (the $IC_{50}$) is determined after fitting with a sigmoidal dose-response model of a plot of the logarithm of the concentration versus percent inhibition measured for the different concentrations. $K_i$'s were calculated from $IC_{50}$ based on Cheng-Prusoff equation (Cheng, Y, Prusoff, W H (1973) *Biochem Pharmacol* 22, 3099-3108): $K_i = IC_{50}/[1 + D/Kd]$ wherein D is the concentration of the fluorescent ligand and Kd is the binding constant for the fluorescent ligand binding to the receptor under the conditions used in the competition experiment.

The compounds of the present invention exhibit $K_i$ values within the range of about 1 nM to about 5000 nM, preferably of about 1 nM to about 1000 nM, and more preferably of about 1 nM to about 30 nM, most preferably of about 1 nM to about 10 nM. The following table shows measured values for some selected compounds of the present invention.

| | $K_i$ (M) |
|---|---|
| Example 1 | 0.016 |
| Example 5 | 0.003 |
| Example 10 | 0.085 |
| Example 13 | 0.091 |
| Example 14 | 0.024 |
| Example 16 | 0.110 |
| Example 22 | 0.076 |
| Example 27 | 0.003 |
| Example 29 | 0.068 |
| Example 30 | 0.196 |
| Example 35 | 0.237 |
| Example 38 | 0.024 |
| Example 41 | 0.027 |
| Example 42 | 0.007 |
| Example 43 | 0.061 |
| Example 44 | 0.004 |
| Example 45 | 0.004 |
| Example 46 | 0.119 |
| Example 49 | 0.031 |
| Example 51 | 0.12 |
| Example 52 | 0.003 |
| Example 53 | 0.01 |
| Example 57 | 0.002 |
| Example 58 | 0.009 |
| Example 60 | 0.327 |
| Example 62 | 0.125 |
| Example 63 | 0.149 |
| Example 73 | 0.0028 |
| Example 77 | 0.016 |
| Example 81 | 0.406 |
| Example 83 | 0.432 |
| Example 85 | 0.06 |
| Example 87 | 0.013 |
| Example 88 | 0.008 |
| Example 92 | 0.049 |
| Example 97 | 0.004 |
| Example 98 | 0.0014 |
| Example 99 | 0.226 |
| Example 100 | 0.0033 |
| Example 102 | 0.0055 |
| Example 108 | 0.1002 |
| Example 111 | 0.0385 |
| Example 112 | 0.0087 |
| Example 117 | 0.3004 |
| Example 120 | 0.1857 |
| Example 123 | 0.0674 |
| Example 125 | 0.0064 |
| Example 128 | 0.659 |
| Example 132 | 0.0013 |
| Example 136 | 0.0294 |
| Example 139 | 0.001 |
| Example 143 | 0.022 |
| Example 145 | 0.0391 |
| Example 149 | 0.0552 |
| Example 153 | 0.8458 |
| Example 163 | 0.8543 |
| Example 165 | 0.0058 |
| Example 167 | 0.1094 |
| Example 172 | 0.0963 |
| Example 175 | 0.5049 |
| Example 180 | 0.007 |
| Example 181 | 0.0109 |
| Example 183 | 0.0011 |
| Example 185 | 0.0369 |
| Example 188 | 0.012 |
| Example 192 | 0.0593 |
| Example 194 | 0.011 |
| Example 195 | 0.0048 |
| Example 197 | 0.0006 |
| Example 202 | 0.0006 |
| Example 204 | 0.002 |
| Example 209 | 0.025 |

Tyrosine-Amino-Transferase Assay

To assess functional agonist or antagonist activities, substances were tested in primary rat hepatocytes for their abilities to modulate tyrosine amino-transferase (TAT) activity. TAT is an enzyme under the control of the glucocorticoid receptor. Binding of an agonist to the glucocorticoid receptor leads to an increase of the TAT activity in primary rat hepatocytes.

To get a primary cell suspension, a Sprague Dawley rat is anesthetized, its liver is cannulated and washed with EDTA and then infused with collagenase. Cells are dissociated by mechanical action and then washed and purified with a Percoll gradient. Cells are plated on 96-well plates coated with collagen type I (50 000 cells/well). To assess a potential agonist activity the substance is given to untreated cells for 24 h. Then the TAT activity is measured as described in Granner et al, *Method in Enyzmology*, Vol. 80, pp 633-637.

To assess a potential antagonist activity, cells are first pre-treated with the potential antagonist. Thirty minutes later a challenge with dexamethasone is done (20 nM). The activity of the TAT is also measured 24 h later.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable salts into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 0.5 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner.

EXAMPLES

Abbreviations: DCM=dichloromethane, DMAP=N,N-Dimethyl-4-aminopyridine, DMF=N,N-dimethylformamide, DMSO=dimethyl sulfoxide, EDC=1-ethyl-3-(3-dimethylaminopropyl) carbodiimide hydrochloride, EI=electron impact (ionization), HPLC=high performance liquid chromatography, ISP=ion spray positive (mode), NMR=nuclear magnetic resonance, MS=mass spectrum, LCMS=liquid chromatography mass spectrometry, THF=tetrahydrofurane, TLC=thin layer chromatography.

General Remark: Reactions were carried out under an atmosphere of nitrogen or argon, where appropriate.

Example 1

3-(2-Chloro-4-methoxy-phenyl)-1,1,1-trifluoro-2-(5-methyl-pyrazin-2-yl)-butan-2-ol Step 1: (2-Chloro-4-methoxy-phenyl)-acetic acid ethyl ester Ethanol (8.72 mL, 150 mmol), DMAP (304 mg, 2 mmol), EDC (9.56 g, 50 mmol), and triethylamine (6.91 mL, 50 mmol) were added under cooling (ice) to a solution of (2-chloro-4-methoxy-phenyl)-acetic acid (10.00 g, 50 mmol, [CAS Reg. No. 91367-09-8]) in $CH_2Cl_2$ (200 mL). The reaction mixture was stirred at r.t. overnight, then diluted ($CH_2Cl_2$), and washed (1N aqueous HCl). The organic layer was dried ($Na_2SO_4$), and the solvent was evaporated. Purification of the residue by column chromatography (silica gel, heptane:ethyl acetate=100:0-70:30) gave the title compound (7.27 g, 64%). $^1H$ NMR (300 MHz, $CDCl_3$) 7.18 (1H, d), 6.94 (1H, d), 6.79 (1H, dd), 4.17 (2H, q), 3.79 (3H, s), 3.69 (2H, s), 1.26 (3H, t).

Step 2: 2-(2-Chloro-4-methoxy-phenyl)-3-(5-methyl-pyrazin-2-yl)-3-oxo-propionic acid ethyl ester Steps 2 and 3 were conducted in close analogy to the method of Gibson et al., *J. Org. Chem.* 2002, 67, 9354. 1,1'-Carbonyldiimidazole (2.46 g, 15 mmol) were added to a solution of 5-methylpyrazine-2-carboxylic acid (2.00 g, 14 mmol, [CAS Reg. No. 5521-55-1]) in DMF (50 mL), and the mixture was stirred for 1.5 h at 50° C. At −10° C., (2-chloro-4-methoxy-phenyl)-acetic acid ethyl ester (3.48 g, 0.15 mmol) was added to the light-brown solution, followed by sodium hydride (50% in mineral oil, 2.31 g, 48 mmol) in small portions over 30 min. The viscous reaction mixture was stirred for 2 h at 0° C., until the reaction was complete (HPLC-UV). The mixture was poured into a $NH_4Cl$ solution/ice, and extracted with ethyl acetate. The organic layer was washed with $H_2O$ and brine, dried ($Na_2SO_4$), and the solvent was evaporated. The title compound (700 mg, 14%) was obtained from the residue by column chromatography (silica gel, heptane:ethyl acetate=100:0-70:30). $^1H$ NMR (300 MHz, $CDCl_3$) 9.15 (1H, s), 8.50 (1H, s), 7.28 (1H, d), 6.97 (1H, d), 6.82 (1H, dd), 6.46 (1H, s), 4.21 (2H, q), 3.79 (3H, s), 2.66 (3H, s), 1.23 (3H, t).

Step 3: 2-(2-Chloro-4-methoxy-phenyl)-1-(5-methyl-pyrazin-2-yl)-ethanone

A mixture of 2-(2-chloro-4-methoxy-phenyl)-3-(5-methyl-pyrazin-2-yl)-3-oxo-propionic acid ethyl ester (700 mg, 2 mmol), sodium chloride (130 mg), water (55 mg) and DMSO (10 mL) was heated for 5 h to 140° C. Upon cooling, the reaction mixture was taken up in ethyl acetate and washed (water, brine). The organic layer was dried ($Na_2SO_4$), and the solvent was evaporated. Purification of the residue by column chromatography (silica gel, heptane:ethyl acetate=100:0-80: 20) gave the title compound (370 mg, 67%). $^1H$ NMR (300 MHz, $CDCl_3$) 9.13 (1H, s), 8.54 (1H, s), 7.18 (1H, d), 6.97 (1H, d), 6.70 (1H, dd), 4.57 (2H, s), 3.80 (3H, s), 2.68 (3H, s); MS (m/e)=277.0 [$MH^+$].

Step 4: 2-(2-Chloro-4-methoxy-phenyl)-1-(5-methyl-pyrazin-2-yl)-propan-1-one

A solution of 2-(2-chloro-4-methoxy-phenyl)-1-(5-methyl-pyrazin-2-yl)-ethanone (370 mg, 1.3 mmol) in DMF (5 mL) was added slowly over 30 min to a suspension of NaH (50% in mineral oil, 96 mg, 1.9 mmol) in DMF (2 mL). After 30 min, methyl iodide (199 mg, 1.4 mmol) was added slowly, and the mixture was stirred for 2d at r.t. The reaction mixture was taken up in ethyl acetate, and washed (water, brine). The organic layer was separated, dried ($Na_2SO_4$), and the solvent was evaporated to give a residue, which was purified by column chromatography (silica gel, heptane:ethyl acetate=100:0-80:20) to give the title compound (290 mg, 75%). $^1$H NMR (300 MHz, $CDCl_3$) 9.08 (1H, s), 8.45 (1H, s), 7.11 (1H, d), 6.92 (1H, d), 6.73 (1H, dd), 5.53 (1H, q), 3.75 (3H, s), 2.61 (3H, s), 1.49 (3H, d); MS (m/e)=291.0 [$MH^+$].

Step 5: 3-(2-Chloro-4-methoxy-phenyl)-1,1,1-trifluoro-2-(5-methyl-pyrazin-2-yl)-butan-2-ol Trifluoromethyltrimethylsilane (2N in THF, 0.6 mL, 1.2 mmol) was added at 0° C. to a solution of 2-(2-chloro-4-methoxy-phenyl)-1-(5-methyl-pyrazin-2-yl)-propan-1-one (290 mg, 1.0 mmol) in THF (7 mL), followed by the addition of tetrabutylammonium fluoride trihydrate (31 mg, 0.1 mmol). After stirring overnight at r.t., the title compound (87 mg, 24%) was isolated from the reaction mixture by reversed-phase, preparative HPLC (Agilent Zorbax XdB-C18 column, solvent gradient 5-95% $CH_3CN$ in 0.1% TFA[aq]). $^1$H NMR (300 MHz, $CDCl_3$) 8.75 (1H, s), 8.13 (1H, s), 7.44 (1H, d), 6.64 (1H, d), 6.59 (1H, dd), 5.90 (1H, s), 4.33 (1H, q), 3.67 (3H, s), 2.50 (3H, s), 1.54 (3H, d); MS (m/e, ISP neg. ion)= 359.1 [$M-H^+$].

Example 2

1,1,1-Trifluoro-2-(2-methyl-pyridin-4-yl)-3-phenyl-butan-2-ol

Step 1: 3-(2-Methyl-pyridin-4-yl)-3-oxo-2-phenyl-propionitrile

Potassium tert-pentylate (25% in toluene, 11.3 mL, 20 mmol) was added dropwise to a solution of phenylacteonitrile (590 mg, 5.0 mmol, [CAS Reg. No. 140-29-4]) in THF (8 mL). After 45 min, 2-methyl-isonicotinic acid ethyl ester (998 mg, 6.0 mmol, [CAS Reg. No. 25635-17-0]) was added drop wise, and the mixture was stirred for 3 h at r.t. The solvent was evaporated, and the residue was taken up in ethyl acetate, and washed with 1N aqueous HCl. The combined water layers were saturated with NaCl, and the crude title compound (as an orange precipitate) was collected by filtration. Evaporation of the organic layer gave an additional small crop of crude product. The combined material (1.02 g, 85%) was used in the next step without further purification. $^1$H NMR (300 MHz, DMSO-$D_6$) 8.81 (1H, d), 7.94 (1H, s), 7.86 (1H, d), 7.78 (2H, d), 7.44 (2H, dd), 7.33 (1H, d), 2.71 (3H, s); MS (m/e)=237.1 [$MH^+$].

Step 2: 1-(2-Methyl-pyridin-4-yl)-2-phenyl-ethanone 3-(2-Methyl-pyridin-4-yl)-3-oxo-2-phenyl-propionitrile (1.02 g, 4.3 mmol) was suspended in HBr (48%, 10 mL) and heated to reflux overnight. The mixture was poured onto ice (20 g), was made alkaline (pH=11) by addition of $NaHCO_3$ (satd.), and extracted with ethyl acetate. The combined organic layers were combined and dried ($Na_2SO_4$). After evaporation of the solvent, the title compound (233 mg, 26%) was isolated from the residue by column chromatography (silica gel, heptane:ethyl acetate=100:0-50:50). $^1$H NMR (300 MHz, DMSO-$D_6$) 8.66 (1H, d), 7.78 (1H, s), 7.69 (1H, d), 7.35-7.24 (5H, m), 4.43 (2H, s), 2.57 (3H, s); MS (m/e)= 212.1 [$MH^+$].

Step 3: 1-(2-Methyl-pyridin-4-yl)-2-phenyl-propan-1-one 1-(2-Methyl-pyridin-4-yl)-2-phenyl-ethanone (233 mg, 1.1 mmol, solution in 5 mL DMF) was added over 15 min to a suspension of NaH (55% in mineral oil, 58 mg, 1.3 mmol) in DMF (2 mL). After 30 min, methyl iodide (0.07 mL, 1.2 mmol) was added slowly drop by drop. The mixture was poured onto ice and extracted with ethyl acetate. The combined organic layers were washed (brine), dried ($Na_2SO_4$), and the solvent was evaporated. Purification by column chromatography (silica gel, heptane:ethyl acetate=100:0-50:50) afforded the title compound (142 mg, 54%). $^1$H NMR (300 MHz, DMSO-$D_6$) 8.56 (1H, d), 7.68 (1H, s), 7.61 (1H, d), 7.30-7.27 (4H, m), 7.20-7.18 (1H, m), 4.92 (1H, q), 1.40 (3H, d); MS (m/e)=226.3 [$MH^+$].

Step 4: 1,1,1-Trifluoro-2-(2-methyl-pyridin-4-yl)-3-phenyl-butan-2-ol

Trifluoromethyltrimethylsilane (2N in THF, 0.76 mL, 1.5 mmol) was added at 0° C. to a solution of 1-(2-methyl-pyridin-4-yl)-2-phenyl-propan-1-one (142 mg, 0.63 mmol) in THF (5 mL), followed by the addition of tetrabutylammonium fluoride trihydrate (40 mg, 0.13 mmol). After stirring overnight at r.t., an additional amount of trifluoromethyltrimethylsilane (0.38 mL), followed by tetrabutylammonium fluoride trihydrate (20 mg) was added to drive the reaction towards completion. The solvent was evaporated, the residue was taken up in methanol, and the title compound (42 mg, 23%) was isolated by reversed-phase, preparative HPLC (Agilent Zorbax XdB-C18 column, solvent gradient 5-95% $CH_3CN$ in 0.1% TFA[aq]). $^1$H NMR (300 MHz, DMSO-$D_6$) 8.25 (1H, d), 7.17 (1H, s), 7.11 (2H, d), 7.09-7.00 (4H, m), 6.93 (1H, s), 3.62 (1H, q), 2.35 (3H, s), 1.42 (3H, d); MS (m/e)=296.4 [$MH^+$].

Example 3

3-(2-Chloro-4-methoxy-phenyl)-1,1,1-trifluoro-2-(2-methyl-pyridin-4-yl)-butan-2-ol Step 1: 2-(2-Chloro-4-methoxy-phenyl)-3-(2-methyl-pyridin-4-yl)-3-oxo-propionitrile The title compound was prepared from (2-chloro-4-methoxy-phenyl)-acetonitrile [CAS Reg. No. 170737-93-6] in analogy to Example 2, step 1. $^1$H NMR (300 MHz, DMSO-$D_6$) 8.80 (1H, d), 7.92 (1H, s), 7.82 (1H, d), 7.45 (1H, d), 7.17-7.14 (1H, m), 7.07-7.01 (1H, m), 3.82 (3H, s), 2.72 (3H, s) (corresponding to the enol form of the title compound); MS (m/e)=301.1 [$MH^+$].

Step 2: 2-(2-Chloro-4-hydroxy-phenyl)-1-(2-methyl-pyridin-4-yl)-ethanone 2-(2-Chloro-4-methoxy-phenyl)-3-(2-methyl-pyridin-4-yl)-3-oxo-propionitrile (1.2 g, 4.0 mmol) was suspended in aqueous HBr (48%, 12 mL) and heated to reflux overnight. Upon cooling, the precipitated yellow solid was filtered and dried. The product (420 mg, 40%) was used in the next step without further purification. $^1$H NMR (300 MHz, DMSO-$D_6$)

8.84 (1H, d), 8.09 (1H, s), 7.97 (1H, d), 7.19 (1H, d), 6.85 (1H, d), 6.73 (1H, dd), 4.49 (2H, s), 2.69 (3H, s); MS (m/e)=262.0 [MH⁺].

Step 3: 2-(2-Chloro-4-methoxy-phenyl)-1-(2-methyl-pyridin-4-yl)-propan-1-one 2-(2-Chloro-4-hydroxy-phenyl)-1-(2-methyl-pyridin-4-yl)-ethanone (420 mg, 1.6 mmol, solution in 10 mL DMF) was added over 30 min to a suspension of NaH (55% in mineral oil, 168 mg, 3.9 mmol) in DMF (4 mL). After 30 min, methyl iodide (0.21 mL, 3.4 mmol) was added drop-wise and slowly. The mixture was poured onto ice and extracted with ethyl acetate. The combined organic layers were washed (brine), dried ($Na_2SO_4$), and the solvent was evaporated. Purification by column chromatography (silica gel, heptane:ethyl acetate=100:0-80:20) afforded the title compound (183 mg, 39%). $^1$H NMR (300 MHz, $CDCl_3$) 8.58 (1H, d), 7.57 (1H, s), 7.45 (1H, d), 6.97 (1H, d), 6.96 (1H, d), 6.71 (1H, dd), 4.98 (1H, q), 3.78 (1H, s), 2.58 (1H, s), 1.46 (3H, d); MS (m/e)=290.1 [MH⁺].

Step 4: 3-(2-Chloro-4-methoxy-phenyl)-1,1,1-trifluoro-2-(2-methyl-pyridin-4-yl)-butan-2-ol The title compound was prepared from 2-(2-chloro-4-methoxy-phenyl)-1-(2-methyl-pyridin-4-yl)-propan-1-one in analogy to Example 2, step 4. $^1$H NMR (300 MHz, DMSO-$D_6$) 8.25 (1H, d), 7.44 (1H, d), 7.21 (1H, s), 7.16 (1H, s), 7.06 (1H, d) 6.76-6.72 (1H, m), 4.05 (1H, q), 3.64 (3H, s), 2.36 (3H, s); MS (m/e)=360.1 [MH⁺].

Example 4

3-(2-Chloro-4-ethoxy-phenyl)-1,1,1-trifluoro-2-(2-methyl-pyridin-4-yl)-pentan-2-ol The title compound was prepared in analogy to Example 3, but using ethyl iodide instead of methyl iodide in step 3. MS (m/e)=388.3 [MH⁺].

Example 5

3-(2-Chloro-4-propoxy-phenyl)-1,1,1-trifluoro-2-(2-methyl-pyridin-4-yl)-hexan-2-ol The title compound was prepared in analogy to Example 3, using propyl iodide in step 3. MS (m/e)=416.4 [MH⁺].

Example 6

3-(2,3-Dichloro-4-methoxy-phenyl)-1,1,1-trifluoro-2-(2-methyl-pyridin-4-yl)-butan-2-ol The title compound was prepared in analogy to Example 1, steps 2 to 5, from (2,3-dichloro-4-methoxy-phenyl)-acetic acid methyl ester [CAS Reg. No. 91361-41-0] and 2-methyl-isonicotinic acid [4021-11-8]. MS (m/e)=394.0 [MH⁺].

Example 7

3-(2-Chloro-5-methoxy-phenyl)-1,1,1-trifluoro-2-(2-methyl-pyridin-4-yl)-butan-2-ol The title compound was prepared in analogy to Example 1 from (2-chloro-5-methoxy-phenyl)-acetic acid [CAS Reg. No. 91367-10-1] and 2-methyl-isonicotinic acid [CAS Reg. No. 4021-11-8]. MS (m/e)=360.0 [MH⁺].

Example 8

3-(2,5-Dichloro-phenyl)-1,1,1-trifluoro-2-(2-methyl-pyridin-4-yl)-butan-2-ol

The title compound was prepared in analogy to Example 1, steps 2 to 5, from (2,5-dichloro-phenyl)-acetic acid ethyl ester [CAS Reg. No. 135941-21-8] and 2-methyl-isonicotinic acid [CAS Reg. No. 4021-11-8]. MS (m/e, ISP neg. ion)=362.3 [M–H⁺].

Example 9

1,1,1-Trifluoro-3-phenyl-2-pyridin-4-yl-butan-2-ol

The title compound was prepared in analogy to Example 2, steps 2 to 4, from 3-oxo-2-phenyl-3-pyridin-4-yl-propionitrile [CAS Reg. No. 42899-64-9]. MS (m/e)=282.1 [MH⁺].

Example 10

3-(2,4-Dichloro-phenyl)-1,1,1-trifluoro-2-pyridin-3-yl-butan-2-ol

The title compound was prepared in analogy to Example 1, steps 4 to 5, from 2-(2,4-dichlorophenyl)-1-(3-pyridinyl)-ethanone [CAS Reg. No. 84901-56-4]. MS (m/e)=350.2 [MH⁺].

Example 11

3-(2,4-Dichloro-phenyl)-1,1,1-trifluoro-2-pyridin-4-yl-butan-2-ol

The title compound was prepared in analogy to Example 1, steps 4-5, from 2-(2,4-dichlorophenyl)-1-(4-pyridinyl)-ethanone [CAS Reg. No. 902170-69-8]. MS (m/e)=350.3 [MH⁺].

Example 12

3-(2,4-Dichloro-phenyl)-1,1,1-trifluoro-2-pyridin-2-yl-butan-2-ol

The title compound was prepared in analogy to Example 2, steps 1 to 4, from 2-(2,4-dichlorophenyl)-acetonitrile [CAS Reg. No. 6306-60-1] and picolinic acid ethyl ester [CAS Reg. No. 2524-52-9]. MS (m/e)=350.2 [MH⁺].

Example 13

3-(2,4-Dichloro-phenyl)-1,1,1-trifluoro-2-pyridin-3-yl-heptan-2-ol

The title compound was prepared in analogy to Example 1, steps 4 to 5, from 2-(2,4-dichlorophenyl)-1-(3-pyridinyl)-ethanone [CAS Reg. No. 84901-56-4], using 1-iodo-butane as the alkylation agent in step 4. MS (m/e)=392.1 [MH⁺].

Example 14

3-(2,4-Dichloro-phenyl)-1,1,1-trifluoro-2-pyridin-3-yl-hexan-2-ol

The title compound was prepared in analogy to Example 1, steps 4 to 5, from 2-(2,4-dichlorophenyl)-1-(3-pyridinyl)-

Example 15

3-(2,4-Dichloro-phenyl)-1,1,1-trifluoro-2-pyridin-3-yl-pentan-2-ol

The title compound was prepared in analogy to Example 1, steps 4 to 5, from 2-(2,4-dichlorophenyl)-1-(3-pyridinyl)-ethanone [CAS Reg. No. 84901-56-4], using iodo ethane as the alkylation agent in step 4. MS (m/e)=363.9 [MH$^+$].

Example 16

4-Cyclopropyl-3-(2,4-dichloro-phenyl)-1,1,1-trifluoro-2-pyridin-3-yl-butan-2-ol

The title compound was prepared in analogy to Example 1, steps 4 to 5, from 2-(2,4-dichlorophenyl)-1-(3-pyridinyl)-ethanone [CAS Reg. No. 84901-56-4], using bromomethyl cyclopropane as the alkylation agent in step 4. MS (m/e)=390.2 [MH$^+$].

Example 17

3-(4-Chloro-2-fluoro-phenyl)-1,1,1-trifluoro-2-pyridin-3-yl-butan-2-ol

The title compound was prepared in analogy to Example 2, steps 1 to 4, from 5-chloro-2-fluorobenzeneacetonitrile [CAS Reg. No. 75279-53-7] and nicotinic acid ethyl ester [CAS Reg. No. 614-18-6]. MS (m/e)=334.1 [MH$^+$].

Example 18

3-(2-Chloro-phenyl)-1,1,1-trifluoro-2-pyridin-3-yl-butan-2-ol

The title compound was prepared in analogy to Example 1, steps 4 to 5, from 2-(2-chlorophenyl)-1-(3-pyridinyl)-ethanone [CAS Reg. No. 31362-68-2]. MS (m/e)=316.0 [MH$^+$].

Example 19

3-(3,4-Dichloro-phenyl)-1,1,1-trifluoro-2-pyridin-3-yl-butan-2-ol

The title compound was prepared in analogy to Example 2, steps 1-4, from 3,4-dichlorobenzeneacetonitrile [CAS Reg. No. 3218-49-3] and nicotinic acid ethyl ester [CAS Reg. No. 614-18-6]. MS (m/e)=350.2 [MH$^+$].

Example 20

3-(2,3-Dichloro-phenyl)-1,1,1-trifluoro-2-pyridin-3-yl-butan-2-ol

The title compound was prepared in analogy to Example 2, steps 1 to 4, from 2,3-dichlorobenzeneacetonitrile [CAS Reg. No. 3218-45-9] and nicotinic acid ethyl ester [CAS Reg. No. 614-18-6]. MS (m/e)=350.2 [MH$^+$].

Example 21

3-(3-Chloro-phenyl)-1,1,1-trifluoro-2-pyridin-3-yl-butan-2-ol

The title compound was prepared in analogy to Example 2, steps 1 to 4, from 3-chlorobenzeneacetonitrile [CAS Reg. No. 1529-41-5] and nicotinic acid ethyl ester [CAS Reg. No. 614-18-6]. MS (m/e)=316.1 [MH$^+$].

Example 22

3-(2,4-Dichloro-phenyl)-1,1,1-trifluoro-2-(6-trifluoromethyl-pyridin-3-yl)-butan-2-ol The title compound was prepared in analogy to Example 2, steps 1-4, from 2,4-dichlorobenzeneacetonitrile [CAS Reg. No. 6306-60-1] and 6-(trifluoromethyl)-3-pyridinecarboxylic acid ethyl ester [CAS Reg. No. 597532-36-0]. MS (m/e)=418.1 [MH$^+$].

Example 23

3-(2,4-Dichloro-phenyl)-1,1,1-trifluoro-2-pyridin-3-yl-4-[1,2,4]triazol-1-yl-butan-2-ol The title compound was prepared in analogy to Example 1, steps 4-5, from 2-(2,4-dichlorophenyl)-1-(3-pyridinyl)-3-(1H-1,2,4-triazol-1-yl)-1-propanone [CAS Reg. No. 98617-42-6]. MS (m/e)=417.2 [MH$^+$].

Example 24

3-(2,4-Dichloro-phenyl)-1,1,1-trifluoro-2-pyridin-4-yl-hexan-2-ol

The title compound was prepared in analogy to Example 1, steps 4-5, from 2-(2,4-dichlorophenyl)-1-(4-pyridinyl)-ethanone [CAS Reg. No. 902170-69-8], using 1-iodo-propane as the alkylation agent in step 4. MS (m/e)=378.2 [MH$^+$].

Example 25

3-(2-Chloro-4-fluoro-phenyl)-1,1,1-trifluoro-2-pyridin-4-yl-hexan-2-ol

The title compound was prepared in analogy to Example 2, steps 1 to 4, from 2-chloro-4-fluorobenzeneacetonitrile [CAS Reg. No. 75279-56-0] and isonicotinic acid methyl ester [CAS Reg. No. 2459-09-8], using 1-iodo-propane as the alkylation agent in step 3. MS (m/e)=292.2 [MH$^+$].

Example 26

1,1,1-Trifluoro-3-(2-methoxy-phenyl)-2-pyridin-4-yl-hexan-2-ol

The title compound was prepared in analogy to Example 1, steps 2 to 5, from (2-methoxybenzene)-acetic acid methyl ester [CAS Reg. No. 27798-60-3] and isonicotinic acid [CAS Reg. No. 55-22-1], using 1-iodo-propane as the alkylation agent in step 4. MS (m/e)=340.1 [MH$^+$].

Example 27

3-(2,4-Dichloro-phenyl)-1,1,1-trifluoro-2-(2-methyl-pyridin-4-yl)-butan-2-ol

The title compound was prepared in analogy to Example 1, steps 2 to 5, from (2,4-dichlorobenzene)-acetic acid methyl ester [CAS Reg. No. 91361-41-0] and 2-methyl-isonicotinic acid [CAS Reg. No. 4021-11-8]. MS (m/e)=364.1 [MH$^+$].

Example 28

3-(2,4-Dichloro-phenyl)-1,1,1-trifluoro-2-(2-methyl-pyridin-4-yl)-hexan-2-ol

The title compound was prepared in analogy to Example 1, steps 2 to 5, from (2,4-dichlorobenzene)-acetic acid methyl ester [CAS Reg. No. 91361-41-0] and 2-methyl-isonicotinic acid [CAS Reg. No. 4021-11-8], using 1-iodo-propane as the alkylation agent in step 4. MS (m/e)=392.1 [MH$^+$].

Example 29

3-(2,4-Dichloro-phenyl)-1,1,1-trifluoro-2-pyrazin-2-yl-butan-2-ol

The title compound was prepared in analogy to Example 1, steps 2 to 5, from (2,4-dichlorobenzene)-acetic acid methyl ester [CAS Reg. No. 91361-41-0] and pyrazine-2-carboxylic acid [CAS Reg. No. 98-97-5]. MS (m/e)=352.0 [MH$^+$].

Example 30

1,1,1-Trifluoro-3-(2-methoxy-phenyl)-2-(2-methyl-pyridin-4-yl)-butan-2-ol

The title compound was prepared in analogy to Example 1, steps 2-5, from (2-methoxybenzene)-acetic acid methyl ester [CAS Reg. No. 27798-60-3] and 2-methyl-isonicotinic acid [CAS Reg. No. 4021-11-8]. MS (m/e)=326.1 [MH$^+$].

Example 31

3-(2-Chloro-5-trifluoromethyl-phenyl)-1,1,1-trifluoro-2-pyridin-4-yl-butan-2-ol

Step 1: 2-Chloro-4-(trifluoromethyl)-benzeneacetic acid methyl ester

2-Chloro-4-(trifluoromethyl)-benzeneacetic acid (3 g) [CAS Reg. No. 601513-26-2] was dissolved in DCM (30 mL) and methyl chloroformate (1.18 g, 0.97 mL) followed by triethylamine (1.4 g, 1.93 mL) were added drop by drop. To the mixture was added DMAP (0.154 g) and the yellow mixture was allowed to stir for 1 hour at 0° C. A clear solution was obtained. The mixture was diluted with DCM (30 mL) and was poured into sat. NH$_4$Cl solution. The layers were separated and the aqueous phase was further extracted with 2 portions of DCM. The organic layers were washed with brine, dried over Na$_2$SO$_4$ and evaporated to give the title compound (3.0 g) that was used without further purification. NMR, (CDCl$_3$): 7.6-7.4 (m, 3H); 3.84 (s, 2H); 3.74 (s, 3H).

Steps 2 to 5: 3-(2-Chloro-5-trifluoromethyl-phenyl)-1,1,1-trifluoro-2-pyridin-4-yl-butan-2-ol The title compound was prepared in analogy to Example 1, steps 2-5, from 2-chloro-4-(trifluoromethyl)-benzeneacetic acid methyl ester and isonicotinic acid [CAS Reg. No. 55-22-1]. MS (m/e)=384.1 [MH$^+$].

Example 32

3-(2-Chloro-6-fluoro-phenyl)-1,1,1-trifluoro-2-pyridin-4-yl-butan-2-ol

The title compound was prepared in low yield in analogy to Example 1, steps 2 to 5, from (2-chloro-6-fluorobenzene)-acetic acid methyl ester [CAS Reg. No. 103473-99-0] and isonicotinic acid [CAS Reg. No. 55-22-1]. MS (m/e, ISP neg. ion)=334.2 [M−H$^+$]. 4-(4-Chloro-3-methyl-2-trifluoromethyl-2,3-dihydro-benzufuran-2-yl)-pyridine was obtained as the main product in step 5 of this reaction sequence. MS (m/e)=314.1 [MH$^+$].

Example 33

1,1,1-Trifluoro-2-pyridin-4-yl-3-o-tolyl-butan-2-ol

The title compound was prepared in analogy to Example 1, steps 2 to 5, from 2-methylbenzenecetic acid methyl ester [CAS Reg. No. 40851-62-5] and isonicotinic acid [CAS Reg. No. 55-22-1]. MS (m/e)=296.3 [MH$^+$].

Example 34

3-(2-Chloro-4-fluoro-phenyl)-2-(2-chloro-pyridin-4-yl)-1,1,1-trifluoro-butan-2-ol The title compound was prepared in analogy to Example 1, steps 2 to 5, from 2-chloro-4-fluorobenzenecetic acid methyl ester [CAS Reg. No. 214262-88-1] and 2-chloroisonicotinic acid [CAS Reg. No. 6313-54-8]. MS (EI)=367.0 [M$^+$].

Example 35

3-(2,4-Dichloro-phenyl)-1,1,1-trifluoro-2-pyridazin-4-yl-butan-2-ol

The title compound was prepared in analogy to Example 1, steps 2 to 5, from 2,4-dichlorobenzeneacetic acid methyl ester [CAS Reg. No. 91361-41-0] and 4-pyridazinecarboxylic acid [CAS Reg. No. 50681-25-9]. MS (m/e)=351.1 [MH$^+$].

Example 36

1,1,1-Trifluoro-3-(2-phenoxy-phenyl)-2-pyridin-4-yl-butan-2-ol

Step 1: 2-Phenoxy-benzeneacetic acid methyl ester

This material was made in analogy to Example 31, step 1, from 2-phenoxybenzene-acetic acid [CAS Reg. No. 25563-02-4]: NMR, (CDCl$_3$): 7.37-7.2 (m, 4H); 7.13-7.04 (m, 2H); 6.98-6.93 (m, 2H); 9.89 (d, 1H); 3.70 (s, 2H); 3.61 (s, 3H).

Steps 2 to 5: 1,1,1-Trifluoro-3-(2-phenoxy-phenyl)-2-pyridin-4-yl-butan-2-ol

The title compound was prepared in analogy to Example 1, steps 2-5, from 2-phenoxy-benzeneacetic acid methyl ester and isonicotinic acid [CAS Reg. No. 55-22-1]. MS (m/e)=374.1 [MH$^+$].

Example 37

3-(2,4-Dichloro-phenyl)-1,1,1-trifluoro-2-(2-methoxy-pyridin-4-yl)-butan-2-ol

The title compound was prepared in analogy to Example 1, steps 2 to 5, from 2,4-dichlorobenzeneacetic acid methyl ester [CAS Reg. No. 91361-41-0] and 2-methoxyisonicotininc acid [CAS Reg. No. 105596-63-2]. MS (m/e)=380.1 [MH$^+$].

Example 38

3-(2,4-Dichloro-phenyl)-1,1,1-trifluoro-2-(5-methyl-pyrazin-2-yl)-butan-2-ol The title compound was prepared in analogy to Example 1, steps 2 to 5, from 2,4-dichlorobenzeneacetic acid methyl ester [CAS Reg. No. 91361-41-0] and 5-methyl-2-pyrazinecarboxylic acid [CAS Reg. No. 5521-55-1]. MS (m/e)= 365.1 [MH$^+$].

Example 39

3-(2,4-Dichloro-phenyl)-1,1,1-trifluoro-2-(6-methyl-pyrazin-2-yl)-butan-2-ol The title compound was prepared in analogy to Example 1, steps 2 to 5, from 2,4-dichlorobenzeneacetic acid methyl ester [CAS Reg. No. 91361-41-0] and 6-methyl-2-pyrazinecarboxylic acid [CAS Reg. No. 5521-61-9], which was made from 2,6-dimethylpyrazine following a procedure from Vishweshwar et al.; *J. Org. Chem.* 2002, 2, 556. MS (m/e)= 365.1 [MH$^+$].

Example 40 and Example 41

(2S,3S)-3-(2,4-Dichloro-phenyl)-1,1,1-trifluoro-2-(6-methyl-pyrazin-2-yl)-butan-2-ol and (2R,3R)-3-(2,4-Dichloro-phenyl)-1,1,1-trifluoro-2-(6-methyl-pyrazin-2-yl)-butan-2-ol These compounds were obtained by preparative HPLC (Column: Chiralpack AD; solvent: 1% isopropanol in heptane) from racemic 3-(2,4-dichloro-phenyl)-1,1,1-trifluoro-2-(6-methyl-pyrazin-2-yl)-butan-2-ol (Example 39).

Example 42

3-(2-Chloro-4-fluoro-phenyl)-2-(2-chloro-6-methoxy-pyridin-4-yl)-1,1,1-trifluoro-butan-2-ol The title compound was prepared in analogy to Example 1, steps 2-5, from 2-chloro-4-fluorobenzeneacetic acid methyl ester [CAS Reg. No. 214262-88-1] and 2-chloro-6-methoxy-4-pyridinecarboxylic acid [CAS Reg. No. 15855-06-8]. MS (m/e)=398.1 [MH$^+$].

Example 43

3-(2,4-Dichloro-phenyl)-1,1,1-trifluoro-2-(1-methyl-1H-pyrazol-4-yl)-butan-2-ol The title compound was prepared in analogy to Example 1, steps 2 to 5, from 2,4-dichlorobenzeneacetic acid methyl ester [CAS Reg. No. 91361-41-0] and 1-methyl-1H-pyrazole-4-carboxylic acid [CAS Reg. No. 5952-92-1]. MS (m/e)= 353.1 [MH$^+$].

Example 44

2-(2-Chloro-6-methyl-pyridin-4-yl)-3-(2,4-dichloro-phenyl)-1,1,1-trifluoro-butan-2-ol The title compound was prepared in analogy to Example 1, steps 2 to 5, from 2,4-dichlorobenzeneacetic acid methyl ester [CAS Reg. No. 91361-41-0] and 2-chloro-6-methyl-4-pyridinecarboxylic acid [CAS Reg. No. 25462-85-5]. MS (m/e)=398.0 [MH$^+$].

Example 45

3-(2,4-Dichloro-phenyl)-1,1,1-trifluoro-2-quinolin-3-yl-butan-2-ol

The title compound was prepared in analogy to Example 1, steps 2 to 5, from 2,4-dichlorobenzeneacetic acid methyl ester [CAS Reg. No. 91361-41-0] and 3-quinolinecarboxylic acid [CAS Reg. No. 6480-68-8]. MS (m/e)=400.0 [MH$^+$].

Example 46

3-(2,4-Dichloro-phenyl)-1,1,1-trifluoro-2-pyrimidin-4-yl-butan-2-ol

The title compound was prepared in analogy to Example 1, steps 2 to 5, from 2,4-dichlorobenzeneacetic acid methyl ester [CAS Reg. No. 91361-41-0] and 4-pyrimidinecarboxylic acid [CAS Reg. No. 31462-59-6]. MS (m/e, ISP, neg. ion)=349.0 [M–H$^+$].

Example 47

3-(2,4-Dichloro-phenyl)-1,1,1-trifluoro-2-(1-methyl-1H-imidazol-4-yl)-butan-2-ol The title compound was prepared in analogy to Example 1, steps 2-5, from 2,4-dichlorobenzeneacetic acid methyl ester [CAS Reg. No. 91361-41-0] and 1-methyl-1H-imidazole-4-carboxylic acid [CAS Reg. No. 41716-18-1]. MS (m/e)= 353.1 [MH$^+$].

Example 48

4-[2-(2,4-Dichloro-phenyl)-1-methoxy-1-trifluoromethyl-propyl]-pyridine

The title compound was prepared from 3-(2,4-dichloro-phenyl)-1,1,1-trifluoro-2-pyridin-4-yl-butan-2-ol (Example 11) by 0-methylation: 3-(2,4-dichloro-phenyl)-1,1,1-trifluoro-2-pyridin-4-yl-butan-2-ol (45 mg) was dissolved in dry DMF (4 mL) under argon at room temperature. To the mixture was added sodium hydride (8.4 mg, 50% in mineral oil) and the mixture was allowed to stir for 30 minutes. Iodomethane (22 mg, 0.01 mL) was added and stirring was continued for 1 hour at room temperature. The mixture was poured into ice water and extracted with ethyl acetate. The organic layer was washed with brine, dried over Na$_2$SO$_4$ and evaporated. The residue was purified by flash chromatography (20 g silica gel, gradient of ethyl acetate in heptane (10 to 40%) to give the desired material as light yellow oil (28 mg). MS (m/e)=364.1 [MH$^+$].

Example 49

3-(2,4-Dichloro-phenyl)-1,1,1-trifluoro-2-pyrazolo[1,5-a]pyridin-2-yl-butan-2-ol The title compound was prepared in analogy to Example 1, steps 2 to 5, from 2,4-dichlorobenzeneacetic acid methyl ester [CAS Reg. No. 91361-41-0] and pyrazolo[1,5-a]pyridine-2-carboxylic acid [CAS Reg. No. 63237-88-7]. MS (m/e)=389.2 [MH$^+$].

Example 50

3-(2,4-Dichloro-phenyl)-1,1,1-trifluoro-2-(1-methyl-1H-pyrazol-3-yl)-butan-2-ol

The title compound was prepared in analogy to Example 1, steps 2 to 5, from 2,4-dichlorobenzeneacetic acid methyl ester [CAS Reg. No. 91361-41-0] and 1-methyl-1H-pyrazole-3-carboxylic acid [CAS Reg. No. 25016-20-0]. MS (m/e)=353.1 [MH$^+$].

Example 51

3-(2,4-Dichloro-phenyl)-1,1,1-trifluoro-2-imidazo[1,2-a]pyridin-2-yl-butan-2-ol

The title compound was prepared in analogy to Example 1, steps 2 to 5, from 2,4-dichlorobenzeneacetic acid methyl ester [CAS Reg. No. 91361-41-0] and imidazo[1,2-a]pyridine-2-carboxylic acid [CAS Reg. No. 64951-08-2]. MS (m/e)=389.1 [MH$^+$].

Example 52

3-(2,4-Dichloro-phenyl)-1,1,1-trifluoro-2-quinolin-6-yl-butan-2-ol

The title compound was prepared in analogy to Example 1, steps 2 to 5, from 2,4-dichlorobenzeneacetic acid methyl ester [CAS Reg. No. 91361-41-0] and 6-quinolinecarboxylic acid [CAS Reg. No. 10349-57-2]. MS (m/e)=400.0 [MH$^+$].

Example 53

3-(2,4-Dichloro-phenyl)-1,1,1-trifluoro-2-quinoxalin-6-yl-butan-2-ol

The title compound was prepared in analogy to Example 1, steps 2 to 5, from 2,4-dichlorobenzeneacetic acid methyl ester [CAS Reg. No. 91361-41-0] and 6-quinoxalinecarboxylic acid [CAS Reg. No. 6925-00-4]. MS (m/e)=401.1 [MH$^+$].

Example 54

2-(2-Benzyloxy-pyridin-4-yl)-3-(2,4-dichloro-phenyl)-1,1,1-trifluoro-butan-2-ol

Step 1: 2-(Phenylmethoxy)-4-pyridinecarboxylic acid

2-Chloro-isonicotinic acid [CAS Reg. No. 6313-54-8] (4 g) and benzyl alcohol (3.3 g) were added to dry toluene (50 mL). Sodium hydride (2.66 g, 50% in mineral oil) was added in 2 portions and the mixture was allowed to stir at room temperature for 30 minutes. 18-Crown-6 (906 mg) was added and the mixture was then heated to 125° C. for 12 hours. An unstirrable, yellow mixture was obtained. This was diluted with more toluene (80 mL) and stirring was continued for another 4 hours at 125° C. TLC analysis confirmed that there was still 2-chloro-isonicotinic acid left. More benzyl alcohol (3.3 g) and sodium hydride was (2.66 g) added and the mixture was heated for another 12 hours. The mixture was cooled and quenched with 1M aqueous HCl (100 mL). Hexane (200 ml) was added and the mixture was stirred at 0° C. for 1 hour; a light brown solid was obtained. The solid was filtered off and washed with hexane. To remove residual water from the solid, toluene was added and removed again. A colorless solid was obtained (4.8 g). MS (m/e, ISP neg ion): 228.3 (M–H$^+$).

Steps 2 to 5: 2-(2-Benzyloxy-pyridin-4-yl)-3-(2,4-dichloro-phenyl)-1,1,1-trifluoro-butan-2-ol The title compound was prepared in analogy to the reaction sequence outlined in Example 1, steps 2 to 5, from 2-chloro-4-(trifluoromethyl)-benzeneacetic acid methyl ester and 2-(phenylmethoxy)-4-pyridinecarboxylic acid with the following modification:

In the methylation step (Example 1, step 4), an inseparable mixture of the desired intermediate 1-(2-benzyloxy-pyridin-4-yl)-2-(2,4-dichloro-phenyl)-propan-1-one with the dimethylated compound 2-benzyloxy-4-[(E or Z)-2-(2,4-dichloro-phenyl)-1-methoxy-propenyl]-pyridine was obtained. This mixture was treated as follows:

A mixture of 1-(2-benzyloxy-pyridin-4-yl)-2-(2,4-dichloro-phenyl)-propan-1-one and 2-benzyloxy-4-[(E or Z)-2-(2,4-dichloro-phenyl)-1-methoxy-propenyl]-pyridine (345 mg) was treated with 50% aqueous H$_2$SO$_4$ (8 mL) at 100° C. for 60 minutes, but some of the starting material could not be dissolved. THF (2 mL) was added and stirring at 100° C. was continued for another hour. The reaction mixture was cooled, poured into ice and basified with sat. Na$_2$CO$_3$ to pH 10. The aqueous phase was then extracted with ethyl acetate and the organic layer was washed with brine, dried over Na$_2$SO$_4$ and evaporated. This material, which was used without further purification was identified to be 4-[2-(2,4-dichloro-phenyl)-propionyl]-1H-pyridin-2-one. MS (m/e)= 296.2 [MH$^+$].

This material was re-benzylated as follows: 4-[2-(2,4-Dichloro-phenyl)-propionyl]-1H-pyridin-2-one (100 mg) was dissolved in absolute benzene (6 mL) and silver carbonate (65 mg) and benzyl bromide (70 mg, 0.05 mL) were added. The mixture was stirred at 50° C. over night and was then poured into ice water. The aqueous phase was extracted with ethyl acetate and the organic layer was washed with brine, dried over Na$_2$SO$_4$ and evaporated. The residue was purified by flash chromatography (20 g silica gel, gradient of ethyl aceate in heptane (0 to 20%)) to give 1-(2-benzyloxy-pyridin-4-yl)-2-(2,4-dichloro-phenyl)-propan-1-one (78 mg) as a colorless oil. MS (m/e)=386.0 [MH$^+$].

Introduction of the trifluoromethyl group was performed as outlined in example 1, step 5, using 1-(2-benzyloxy-pyridin-4-yl)-2-(2,4-dichloro-phenyl)-propan-1-one as the staring material. 2-(2-Benzyloxy-pyridin-4-yl)-3-(2,4-dichloro-phenyl)-1,1,1-trifluoro-butan-2-ol was obtained as a light yellow oil. MS (m/e)=456.1 [MH$^+$].

Example 55

3-(2,4-Dichloro-phenyl)-1,1,1-trifluoro-2-(6-methoxy-pyridin-3-yl)-butan-2-ol

The title compound was prepared in analogy to Example 1, steps 2-5, from 2,4-dichlorobenzeneacetic acid methyl ester [CAS Reg. No. 91361-41-0] and 6-methoxy-3-pyridinecarboxylic acid [CAS Reg. No. 66572-55-2]. MS (m/e)=480.1 [MH$^+$].

Example 56

3-(2,4-Dichloro-phenyl)-1,1,1-trifluoro-2-(5-methyl-1-phenyl-1H-pyrazol-4-yl)-butan-2-ol The title compound was prepared in analogy to Example 1, steps 2 to 5, from 2,4-dichlorobenzeneacetic acid methyl ester [CAS Reg. No. 91361-41-0] and 5-methyl-1-phenyl-1H-pyrazole-4-carboxylic acid [CAS Reg. No. 91138-00-0]. MS (m/e)=429.2 [MH$^+$].

Example 57

2-Benzothiazol-6-yl-3-(2,4-dichloro-phenyl)-1,1,1-trifluoro-butan-2-ol

The title compound was prepared in analogy to Example 1, steps 2 to 5, from 2,4-dichlorobenzeneacetic acid methyl ester [CAS Reg. No. 91361-41-0] and 6-benzothiazolecarboxylic acid [CAS Reg. No. 3622-35-3]. MS (m/e)=406.1 [MH$^+$].

Example 58

3-(2,4-Dichloro-phenyl)-1,1,1-trifluoro-2-quinoxalin-2-yl-butan-2-ol

The title compound was prepared in analogy to Example 1, steps 2 to 5, from 2,4-dichlorobenzeneacetic acid methyl ester [CAS Reg. No. 91361-41-0] and 2-quinoxalinecarboxylic acid [CAS Reg. No. 879-65-2]. MS (m/e)=401.1[MH$^+$].

Example 59

3-(2,4-Dichloro-phenyl)-1,1,1-trifluoro-2-(2-pyridin-4-yl-thiazol-4-yl)-butan-2-ol The title compound was prepared in analogy to Example 1, steps 2 to 5, from 2,4-dichlorobenzeneacetic acid methyl ester [CAS Reg. No. 91361-41-0] and 2-(4-pyridinyl)-4-thiazolecarboxylic acid [CAS Reg. No. 21278-86-4]. MS (m/e)=433.1[MH$^+$].

Example 60

3-(2,4-Dichloro-phenyl)-1,1,1-trifluoro-2-thiazol-2-yl-butan-2-ol

The title compound was prepared in analogy to Example 1, steps 2 to 5, from 2,4-dichlorobenzeneacetic acid methyl ester [CAS Reg. No. 91361-41-0] and 2-thiazolecarboxylic acid [CAS Reg. No. 14190-59-1]. MS (m/e, ISP neg. ion)=354.0[(M−H$^+$)$^-$].

Example 61

7-[2-(2,4-Dichloro-phenyl)-1-hydroxy-1-trifluoromethyl-propyl]-3,4-dihydro-1H-isoquinoline-2-carboxylic acid tert-butyl ester The title compound was prepared in analogy to Example 1, steps 2 to 5, from 2,4-dichlorobenzeneacetic acid methyl ester [CAS Reg. No. 91361-41-0] and 3,4-dihydro-2,7(1H)-isoquinolinedicarboxylic acid 2-(1,1-dimethylethyl) ester [CAS Reg. No. 149353-95-7]. MS (m/e)=504.0 (weak, MH$^+$); 448.0[(M−C$_4$H$_9$+H$^+$)$^-$].

Example 62

3-(2,4-Dichloro-phenyl)-1,1,1-trifluoro-2-pyrimidin-5-yl-butan-2-ol

The title compound was prepared in analogy to Example 1, steps 2 to 5, from 2,4-dichlorobenzeneacetic acid methyl ester [CAS Reg. No. 91361-41-0] and 5-pyrimidinecarboxylic acid [CAS Reg. No. 4595-61-3]. MS (m/e, ISP neg. ion)=349.0[(M−H$^+$)$^-$].

Example 63

2-(1-Benzyl-1H-pyrazol-4-yl)-3-(2,4-dichloro-phenyl)-1,1,1-trifluoro-butan-2-ol

Step 1: 1-Benzyl-1H-pyrazole-4-carboxylic acid ethyl ester

1H-Pyrazole-4-carboxylic acid, ethyl ester [CAS Reg. No. 37622-90-5] (1.52 g) was dissolved in dry DMF (25 mL) and cooled to 0° C. under argon. To the mixture was added sodium hydride (651 mg, 60% in mineral oil) and the mixture was allowed to stir at 0° C. for 30 minutes. Benzyl bromide (2.23 g, 1.55 mL) was added over a period of 15 minutes and stirring was continued again for 1 hour at 0° C. The reaction mixture was poured into ice water and extracted with ethyl acetate. The organic layer was washed with brine, dried over Na$_2$SO$_4$ and evaporated. Toluene was added and the removed by evaporation to remove some residual water. The residue was purified by flash chromatography (50 g silica gel, gradient of ethyl acetate in heptane (10% to 40%) to give the desired material as a light yellow liquid (2.36 g). MS (m/e)=231.1[MH$^+$].

Step 2: 1-Benzyl-1H-pyrazole-4-carboxylic acid

This known compound [CAS Reg. No. 401647-24-3] was made from 1-benzyl-1 H-pyrazole-4-carboxylic acid ethyl ester by saponification: 1-benzyl-1H-pyrazole-4-carboxylic acid ethyl ester (2.35 g) was dissolved in dry THF (25 mL) and then a 1M aqueous solution of LiOH (15.31 mL) was added. The mixture was stirred at 60° C. for 2.5 hours and analyzed by TLC: starting material was still visible. Another batch of LiOH monohydrate (1.29 g) was added and the mixture was allowed to stir at room temperature for 48 hours. The mixture was poured into ice water and acidified with 2M aqueous HCl (20 mL). The aqueous phase was extracted with ethyl acetate and the organic layer was washed with brine, dried over Na$_2$SO$_4$ and evaporated to give the title compound as a colorless solid (1.55 g). MS (m/e, ISP neg. ion)=201.6 [(M−H$^+$)$^-$].

Steps 3 to 6: 2-(1-Benzyl-1H-pyrazol-4-yl)-3-(2,4-dichloro-phenyl)-1,1,1-trifluoro-butan-2-ol The title compound was prepared in analogy to Example 1, steps 2 to 5, from 2,4-dichlorobenzeneacetic acid methyl ester [CAS Reg. No. 91361-41-0] and 1-benzyl-1H-pyrazole-4-carboxylic acid. MS (m/e)=429.1 (MH$^+$).

Example 64

3-(2,4-Dichloro-phenyl)-1,1,1-trifluoro-2-(4-methyl-3,4-dihydro-2H-pyrido[3,2-b][1,4]oxazin-7-yl)-butan-2-ol The title compound was prepared in analogy to Example 1, steps 2-5, from 2,4-dichlorobenzeneacetic acid methyl ester [CAS Reg. No. 91361-41-0] and 3,4-dihydro-4-methyl-2H-pyrido[3,2-b]-1,4-oxazine-7-carboxylic acid [CAS Reg. No. 915707-58-3]. MS (m/e)=421.0 (MH$^+$).

Example 65

3-(2-Chloro-4-fluoro-phenyl)-1,1,1-trifluoro-2-quinolin-3-yl-butan-2-ol

The title compound was prepared in analogy to Example 1, steps 2-5, from 2-chloro-4-fluorobenzenecetic acid methyl ester [CAS Reg. No. 214262-88-1] and 3-quinolinecarboxylic acid [CAS Reg. No. 6480-68-8]. MS (m/e)=384.1 (MH$^+$).

Example 66

3-(2-Chloro-4-methoxy-phenyl)-1,1,1-trifluoro-2-quinoxalin-2-yl-butan-2-ol

The title compound was prepared in analogy to Example 1, steps 1 to 5, from (2-chloro-4-methoxy-phenyl)-acetic acid [CAS Reg. No. 91367-09-8] and 2-quinoxalinecarboxylic acid [CAS Reg. No. 879-65-2] with the following modification: (2-chloro-4-methoxy-phenyl)-acetic acid methyl ester was made in step 1 (by using methanol instead of ethanol) and this methyl ester was used as a starting material for step 2. Title compound 3-(2-chloro-4-methoxy-phenyl)-1,1,1-trifluoro-2-quinoxalin-2-yl-butan-2-ol: MS (m/e)=397.2 (MH$^+$).

Example 67

3-(2-Chloro-4-fluoro-phenyl)-1,1,1-trifluoro-2-quinolin-6-yl-butan-2-ol

The title compound was prepared in analogy to Example 1, steps 2 to 5, from 2-chloro-4-fluorobenzene acetic acid methyl ester [CAS Reg. No. 214262-88-1] and 6-quinolinecarboxylic acid [CAS Reg. No. 10349-57-2]. MS (m/e)=384.1 (MH$^+$).

Example 68

3-(2,4-Dichloro-phenyl)-1,1,1-trifluoro-2-(6-pyrrolidin-1-yl-pyridin-2-yl)-butan-2-ol The title compound was prepared in analogy to Example 1, steps 2 to 5, from 2,4-dichlorobenzeneacetic acid methyl ester [CAS Reg. No. 91361-41-0] and 6(1-pyrrolidinyl)-2-pyridinecarboxylic acid [CAS Reg. No. 450368-20-4]. MS (m/e)=419.2 (MH$^+$).

Example 69

3-(2-Chloro-4-fluoro-phenyl)-1,1,1-trifluoro-2-(6-methyl-pyrazin-2-yl)-butan-2-ol The title compound was prepared in analogy to Example 1, steps 2 to 5, from 2-chloro-4-fluorobenzene acetic acid methyl ester [CAS Reg. No. 214262-88-1] and 6-methyl-2-pyrazinecarboxylic acid [CAS Reg. No. 5521-61-9], which was made as outlined in example 39. MS (m/e)=349.2 (MH$^+$).

Example 70 and Example 71

(2S,3S)-3-(2,4-Dichloro-phenyl)-1,1,1-trifluoro-2-quinolin-6-yl-butan-2-ol and (2R,3R)-3-(2,4-Dichloro-phenyl)-1,1,1-trifluoro-2-quinolin-6-yl-butan-2-ol These materials were obtained by preparative HPLC (Column: Chiralpack AD; solvent: 1% isopropanol in heptane) from racemic 3-(2,4-dichloro-phenyl)-1,1,1-trifluoro-2-quinolin-6-yl-butan-2-ol (example 52).

Example 72

3-Chloro-4-[3,3,3-trifluoro-2-hydroxy-1-methyl-2-(5-methyl-pyrazin-2-yl)-propyl]-phenol A solution of 3-(2-chloro-4-methoxy-phenyl)-1,1,1-trifluoro-2-(5-methyl-pyrazin-2-yl)-butan-2-ol (Example 1, 60 mg, 0.17 mmol) in aqueous HBr (48%, 2 mL) was refluxed for 3 h. The reaction mixture was poured into ice/water, and extracted (ethyl acetate). The combined organic layers were dried (Na$_2$SO$_4$), filtered and evaporated. The residue was taken up in methanol and purified (reversed-phase, preparative HPLC, Agilent Zorbax XdB-C18 column, solvent gradient 5-95% CH$_3$CN in 0.1% TFA[aq]) to give the title compound (44 mg). MS (m/e)=347.1 (MH$^+$).

Example 73

3-Chloro-4-[3,3,3-trifluoro-2-hydroxy-1-methyl-2-(2-methyl-pyridin-4-yl)-propyl]-phenol The title compound was prepared in analogy to Example 72 from 3-(2-chloro-4-methoxy-phenyl)-1,1,1-trifluoro-2-(2-methyl-pyridin-4-yl)-butan-2-ol (Example 3). MS (m/e)=346.1 (MH$^+$).

Example 74

3-(4-Benzyloxy-2-chloro-phenyl)-1,1,1-trifluoro-2-(2-methyl-pyridin-4-yl)-butan-2-ol Potassium iodide (4 mg, 0.02 mmol), potassium carbonate (45 mg, 0.33 mmol), and benzyl chloride (41 mg, 0.33 mmol) were added to a solution of 3-chloro-4-[3,3,3-trifluoro-2-hydroxy-1-methyl-2-(2-methyl-pyridin-4-yl)-propyl]-phenol (Example 73, 50 mg, 0.14 mmol) in acetone (3 mL), and the mixture was refluxed for 3.5 h. The green suspension was filtered, the solvent evaporated, and the title compound (14 mg) was isolated from the residue by reversed-phase, preparative HPLC (Agilent Zorbax XdB-C18 column, solvent gradient 5-95% CH$_3$CN in 0.1% TFA[aq]). MS (m/e)=436.1 (MH$^+$).

Example 75

{4-[2-(2,4-Dichloro-phenyl)-1-hydroxy-1-trifluoromethyl-propyl]-pyridin-2-yloxy}-acetic acid Step 1: 4-[2-(2,4-Dichloro-phenyl)-1-hydroxy-1-trifluoromethyl-propyl]-1H-pyridin-2-one 2-(2-Benzyloxy-pyridin-4-yl)-3-(2,4-dichloro-phenyl)-1,1,1-trifluoro-butan-2-ol (Example 54, 300 mg) was dissolved in ethyl acetate (10 mL) and the flask was flushed with argon. Palladium on activated charcoal (10% Pd, 75 mg) was added and the mixture was hydrogenated for 2 hours with vigorous stirring. The suspension was filtered and the catalyst was washed with methanol. The filtrate was concentrated in vacuo and the residue was dried in high vacuum to give the title compound as a light brown powder (217 mg). MS (m/e, ISP neg. ion): 364.4 (M–H$^+$)$^-$.

Step 2: {4-[2-(2,4-Dichloro-phenyl)-1-hydroxy-1-trifluoromethyl-propyl]-pyridin-2-yloxy}-acetic acid methyl ester To a solution of 4-[2-(2,4-dichloro-phenyl)-1-hydroxy-1-trifluoromethyl-propyl]-1H-pyridin-2-one (100 mg) in toluene (5 mL) was added bromoacetic acid methyl ester (50 mg, 0.03 mL) and Ag$_2$CO$_3$ (53 mg) and the mixture was allowed to stir for 3.5 hours at 145° C. The mixture was cooled to room temperature, filtered and the residue was purified by flash chromatography (10 silica gel cartridge, using ethyl acetate/heptane 1:9 as an eluent) to provide the title compound as a colorless oil (54 mg). MS (m/e): 438.1 (MH$^+$).

Step 3: {4-[2-(2,4-Dichloro-phenyl)-1-hydroxy-1-trifluoromethyl-propyl]-pyridin-2-yloxy}-acetic acid To a solution of {4-[2-(2,4-dichloro-phenyl)-1-hydroxy-1-trifluoromethyl-propyl]-pyridin-2-yloxy}-acetic acid methyl ester (127 mg) in methanol (2 mL) was added an aqueous solution of NaOH (1N, 0.58 mL) and the mixture was allowed to stir at 55° C. for 2 hours. The pH of the mixture was adjusted to pH 2 with aqueous 1N HCl solution and methanol was removed by evaporation. The aqueous solution was extracted twice with ethyl acetate and the organic layers were washed with brine, dried and evaporated. The residual oil was stirred in hexane (5 mL) over night and the suspension was filtered to give the title compound as a colorless powder (96 mg). MS (m/e): 424.2 (MH)$^+$.

Example 76

4-Chloro-3-[3,3,3-trifluoro-2-hydroxy-1-methyl-2-(6-methyl-pyrazin-2-yl)-propyl]-benzoic acid Steps 1 to 4: 4-Chloro-3-[3,3,3-trifluoro-2-hydroxy-1-methyl-2-(6-methyl-pyrazin-2-yl)-propyl]-benzoic acid methyl ester This material was prepared in analogy to Example 1, steps 2 to 5, from known 2-chloro-5-(methoxycarbonyl)-benzeneacetic acid methyl ester [CAS Reg. No. 903899-45-6] and 6-methyl-2-pyrazinecarboxylic acid ([CAS Reg. No. 5521-61-9], preparation see Example 39). MS (m/e)=389.4 (MH$^+$).

Step 5: 4-Chloro-3-[3,3,3-trifluoro-2-hydroxy-1-methyl-2-(6-methyl-pyrazin-2-yl)-propyl]-benzoic acid To a solution of 4-chloro-3-[3,3,3-trifluoro-2-hydroxy-1-methyl-2-(6-methyl-pyrazin-2-yl)-propyl]-benzoic acid methyl ester (50 mg) in methanol (1 mL) was added an aqueous solution of 1N NaOH (0.257 mL) and the mixture was allowed to stir at 40° C. for 12 hours. Methanol was removed by evaporation and the residue was diluted with water. The solution was extracted with ethyl acetate and the organic layer was washed with water. The aqueous layers were combined and aqueous HCl (1N, 0.257 mL) was added. The solution was extracted with ethyl acetate twice and the organic layers were washed with brine, dried over MgSO$_4$ and evaporated. The residue was evaporated once from heptane to give, after drying, the title compound as a white solid (47 mg). MS (m/e, ISP neg. ion): 373.1 (M–H$^+$)$^-$.

Example 77

3-[2-Chloro-4-(2-methoxy-ethoxy)-phenyl]-1,1,1-trifluoro-2-(2-methyl-pyridin-4-yl)-butan-2-ol The title compound was prepared in analogy to Example 74 from 2-bromoethyl methyl ether. MS (m/e)=404.4 (MH$^+$).

Example 78

{3-Chloro-4-[3,3,3-trifluoro-2-hydroxy-1-methyl-2-(2-methyl-pyridin-4-yl)-propyl]-phenoxy}-acetic acid tert-butyl ester The title compound was prepared in analogy to Example 74 from tert-butyl bromoacetate. MS (m/e)=460.3 (MH$^+$).

Example 79

{3-Chloro-4-[3,3,3-trifluoro-2-hydroxy-1-methyl-2-(2-methyl-pyridin-4-yl)-propyl]-phenoxy}-acetic acid Under an atmosphere of nitrogen, trifluoroacetic acid (1.5 ml) was added to a solution of {3-chloro-4-[3,3,3-trifluoro-2-hydroxy-1-methyl-2-(2-methyl-pyridin-4-yl)-propyl]-phenoxy}-acetic acid tert-butyl ester (Example 78, 98 mg) in dichloromethane (1.5 ml). The reaction mixture was stirred for 1 h at r.t., and then diluted with water, and extracted (ethyl acetate). The combined organic layers were dried (Na$_2$SO$_4$), filtered, and evaporated. Flash chromatography provided the title compound (27 mg, 31%). MS (m/e)=404.4 (MH$^+$).

Example 80

2-{3-Chloro-4-[3,3,3-trifluoro-2-hydroxy-1-methyl-2-(5-methyl-pyrazin-2-yl)-propyl]-phenoxy}-acetamide The title compound was prepared in analogy to Example 74 from 2-bromoacetamide and 3-chloro-4-[3,3,3-trifluoro-2-hydroxy-1-methyl-2-(5-methyl-pyrazin-2-yl)-propyl]-phenol (Example 72). MS (m/e)=404.4 (MH$^+$).

Example 81

3-{2-Chloro-4-[2-(2-methoxy-ethoxy)-ethoxy]-phenyl}-1,1,1-trifluoro-2-(5-methyl-pyrazin-2-yl)-butan-2-ol The title compound was prepared in analogy to Example 74 from 1-bromo-2-(2-methoxyethoxy)ethane and 3-chloro-4-[3,3,3-trifluoro-2-hydroxy-1-methyl-2-(5-methyl-pyrazin-2-yl)-propyl]-phenol (Example 72). MS (m/e)=449.0 (MH$^+$).

Example 82

{3-Chloro-4[3,3,3-trifluoro-2-hydroxy-1-methyl-2-(5-methyl-pyrazin-2-yl)-propyl]-phenoxy}-acetic acid tert-butyl ester The title compound was prepared in analogy to Example 74 from tert-butyl bromoacetate and 3-chloro-4-[3,3,3-trifluoro- 2-hydroxy-1-methyl-2-(5-methyl-pyrazin-2-yl)-propyl]-phenol (Example 72). MS (m/e)=461.1 (MH$^+$).

Example 83

Acetic acid 2-{3-chloro-4-[3,3,3-trifluoro-2-hydroxy-1-methyl-2-(5-methyl-pyrazin-2-yl)-propyl]-phenoxy}-ethyl ester The title compound was prepared in analogy to Example 74 from 2-bromoethyl acetate and 3-chloro-4-[3,3,3-trifluoro-2-hydroxy-1-methyl-2-(5-methyl-pyrazin-2-yl)-propyl]-phenol (Example 72). MS (m/e)=433.1 (MH$^+$).

Example 84

(2-{3-Chloro-4-[3,3,3-trifluoro-2-hydroxy-1-methyl-2-(5-methyl-pyrazin-2-yl)-propyl]-phenoxy}-ethyl)-carbamic acid tert-butyl ester The title compound was prepared in analogy to Example 74 from 2-(BOC-amino)ethyl bromide and 3-chloro-4-[3,3,3-trifluoro-2-hydroxy-1-methyl-2-(5-methyl-pyrazin-2-yl)-propyl]-phenol (Example 72). MS (m/e)=489.9 (MH$^+$).

Example 85

3-[2-Chloro-4-(2,2-difluoro-ethoxy)-phenyl]-1,1,1-trifluoro-2-(5-methyl-pyrazin-2-yl)-butan-2-ol The title compound was prepared in analogy to Example 74 from 2-bromo-1,1-difluoroethane and 3-chloro-4-[3,3,3-trifluoro-2-hydroxy-1-methyl-2-(5-methyl-pyrazin-2-yl)-propyl]-phenol (Example 72). MS (m/e)=411.0 (MH$^+$).

Example 86

3-[2-Chloro-4-(2-methoxy-ethoxy)-phenyl]-1,1,1-trifluoro-2-(5-methyl-pyrazin-2-yl)-butan-2-ol The title compound was prepared in analogy to Example 74 from 2-bromoethyl methyl ether and 3-chloro-4-[3,3,3-trifluoro-2-hydroxy-1-methyl-2-(5-methyl-pyrazin-2-yl)-propyl]-phenol (Example 72). MS (m/e)=405.3 (MH$^+$).

Example 87

3-[2-Chloro-4-([1,2,4]oxadiazol-3-ylmethoxy)-phenyl]-1,1,1-trifluoro-2-(5-methyl-pyrazin-2-yl)-butan-2-ol The title compound was prepared in analogy to Example 74 from 3-(chloromethyl)-1,2,4-oxadiazole and 3-chloro-4-[3,3,3-trifluoro-2-hydroxy-1-methyl-2-(5-methyl-pyrazin-2-yl)-propyl]-phenol (Example 72). MS (m/e)=429.3 (MH$^+$).

Example 88

3-[2-Chloro-4-(5-methyl-isoxazol-3-ylmethoxy)-phenyl]-1,1,1-trifluoro-2-(5-methyl-pyrazin-2-yl)-butan-2-ol The title compound was prepared in analogy to Example 74 from 3-chloromethyl-5-methylisoxazole and 3-chloro-4-[3,3,3-trifluoro-2-hydroxy-1-methyl-2-(5-methyl-pyrazin-2-yl)-propyl]-phenol (Example 72). MS (m/e)=442.3 (MH$^+$).

Example 89

3-[2-Chloro-4-(2-hydroxy-ethoxy)-phenyl]-1,1,1-trifluoro-2-(5-methyl-pyrazin-2-yl)-butan-2-ol A solution of acetic acid 2-{3-chloro-4-[3,3,3-trifluoro-2-hydroxy-1-methyl-2-(5-methyl-pyrazin-2-yl)-propyl]-phenoxy}-ethyl ester in ethanol was added to a solution of KOH in ethanol. The reaction mixture was stirred for 3 h at r.t., before it was taken up in ethyl acetate, washed with water and brine, and the solvent was evaporated. Flash chromatography provided the title compound. MS (m/e)=391.0 (MH$^+$).

Example 90

3-[4-(2-Amino-ethoxy)-2-chloro-phenyl]-1,1,1-trifluoro-2-(5-methyl-pyrazin-2-yl)-butan-2-ol Under an atmosphere of nitrogen, trifluoroacetic acid was added to a solution of (2-{3-chloro-4-[3,3,3-trifluoro-2-hydroxy-1-methyl-2-(5-methyl-pyrazin-2-yl)-propyl]-phenoxy}-ethyl)-carbamic acid tert-butyl ester (example 84) in dichloromethane. The reaction mixture was stirred for 1 h at r.t., and then diluted with water, neutralised (satd. NaHCO$_3$) and extracted (ethyl acetate). The combined organic layers were dried, filtered, and evaporated. Flash chromatography provided the title compound. MS (m/e)=390.3 (MH$^+$).

Example 91

3-[2-Chloro-4-(1-methyl-1H-tetrazol-5-ylmethoxy)-phenyl]-1,1,1-trifluoro-2-(5-methyl-pyrazin-2-yl)-butan-2-ol The title compound was prepared in analogy to Example 74 from 5-chloromethyl-1-methyl-1H-tetrazole [57235-84-4] and 3-chloro-4-[3,3,3-trifluoro-2-hydroxy-1-methyl-2-(5-methyl-pyrazin-2-yl)-propyl]-phenol (Example 72). MS (m/e)=443.4 (MH$^+$).

Example 92

3-[2-Chloro-4-(3-methyl-[1,2,4]thiadiazol-5-ylmethoxy)-phenyl]-1,1,1-trifluoro-2-(5-methyl-pyrazin-2-yl)-butan-2-ol The title compound was prepared in analogy to Example 74 from 5-chloromethyl-3-methyl-[1,2,4]thiadiazole [163009-79-8] and 3-chloro-4-[3,3,3-trifluoro-2-hydroxy-1-methyl-2-(5-methyl-pyrazin-2-yl)-propyl]-phenol (Example 72). MS (m/e)=459.5 (MH$^+$).

Example 93

3-(2-Chloro-4-fluoro-phenyl)-1,1,1-trifluoro-2-(2-methoxy-pyridin-4-yl)-butan-2-ol The title compound was prepared in analogy to Example 1, steps 2 to 5, from methyl-2-chloro-4-fluoro-phenyl acetate [CAS Reg. No. 214262-88-1] and 2-methoxyisonicotinic acid [CAS Reg. No. 105596-63-2]. MS (m/e)=364.1 (MH$^+$).

Example 94

1,1,1-Trifluoro-2-(5-methyl-pyrazin-2-yl)-3-naphthalen-1-yl-butan-2-ol

The title compound was prepared in analogy to Example 1, steps 2 to 5, from 1-naphthaleneacetic acid methyl ester [CAS Reg. No. 2876-78-0] and 5-methyl-2-pyrazinecarboxylic acid [CAS Reg. No. 5521-55-1]. MS (m/e)=347.1 (MH$^+$).

Example 95

2-(6-Chloro-pyrazin-2-yl)-3-(2,4-dichloro-phenyl)-1,1,1-trifluoro-butan-2-ol

The title compound was prepared in analogy to Example 1, steps 2 to 5, from 2,4-dichloro-benzeneacetic acid methyl ester [CAS Reg. No. 55954-23-9] and 6-chloro-2-pyrazinecarboxylic acid [CAS Reg. No. 23688-89-3]. MS (m/e)=384.0 (M$^+$).

Example 96

3-(2,4-Dichloro-phenyl)-1,1,1-trifluoro-2-isoquinolin-5-yl-butan-2-ol

The title compound was prepared in analogy to Example 1, steps 2 to 5, from 2,4-dichloro-benzeneacetic acid methyl ester [CAS Reg. No. 55954-23-9] and 5-isoquinolineacetic acid [CAS Reg. No. 395074-85-8]. MS (m/e)=400.3 (MH$^+$).

Example 97

2-Cinnolin-4-yl-3-(2,4-dichloro-phenyl)-1,1,1-trifluoro-butan-2-ol

The title compound was prepared in analogy to Example 1, steps 2 to 5, from 2,4-dichloro-benzeneacetic acid methyl ester [CAS Reg. No. 55954-23-9] and 4-cinnolinecarboxylic acid [CAS Reg. No. 21905-86-2]. MS (m/e)=401.3 (MH$^+$).

Example 98

3-(2,4-Dichloro-phenyl)-1,1,1-trifluoro-2-pyrazolo[1,5-a]pyridin-3-yl-butan-2-ol The title compound was prepared in analogy to Example 1, steps 2 to 5, from 2,4-dichloro-benzeneacetic acid methyl ester [CAS Reg. No. 55954-23-9] and pyrazolo[1,5-a]pyridine-3-carboxylic acid [CAS Reg. No. 16205-46-2]. MS (neg. ion, m/e)=387.1 ((M–H)$^-$).

Example 99

3-(2,4-Dichloro-phenyl)-1,1,1-trifluoro-2-(1-phenethyl-1H-pyrazol-4-yl)-butan-2-ol The title compound was prepared in low yield in analogy to Example 1, steps 2 to 5, from 2,4-dichloro-benzeneacetic acid methyl ester [CAS Reg. No. 55954-23-9] and 1-(2-phenyl-ethyl)-1H-pyrazole-4-carboxylic acid [CAS Reg. No. 898910-39-9]. MS (m/e)=443.2 (MH$^+$).

Example 100

2-(6-Chloro-pyridin-3-yl)-3-(2,4-dichloro-phenyl)-1,1,1-trifluoro-butan-2-ol

The title compound was prepared in analogy to Example 1, steps 2 to 5, from 2,4-dichloro-benzeneacetic acid methyl ester [CAS Reg. No. 55954-23-9] and 6-chloronicotinic acid [CAS Reg. No. 5326-23-8]. MS (neg. ion, m/e)=382.0 ((M–H)$^-$).

Example 101

5-[2-(2,4-Dichloro-phenyl)-1-hydroxy-1-trifluoromethyl-propyl]-pyridine-2-carbonitrile The title compound was prepared in analogy to Example 1, steps 2 to 5, from 2,4-dichloro-benzeneacetic acid methyl ester [CAS Reg. No. 55954-23-9] and 6-cyanonicotinic acid [CAS Reg. No. 70165-31-0]. MS (neg. ion, m/e)=373.1 ((M–H)$^-$).

Example 102

3-(2-Chloro-4-phenethyloxy-phenyl)-1,1,1-trifluoro-2-(2-methyl-pyridin-4-yl)-butan-2-ol Sodium hydride (60% in mineral oil, 20.4 mg) was added to abs. DMF (2 mL). To this mixture was added a solution of 3-chloro-4-[3,3,3-trifluoro-2-hydroxy-1-methyl-2-(2-methyl-pyridin-4-yl)-propyl]-phenol (Example 73, 80 mg) in DMF (2 mL) over 15 minutes. The mixture was then allowed to stir for 30 min at RT. The mixture was cooled to 0° C. and a solution of 2-bromoethylbenzene ((0.033 mL) in DMF (1 mL) was added within 10 minutes. The mixture was then heated to 50° C. over night. The reaction mixture was poured into ice/water and extracted with ethyl acetate. The organic extracts were washed with brine, dried over Na$_2$SO$_4$ and evaporated. The residue was purified by flash chromatography (silica gel, gradient of ethyl acetate in heptane) to give the title compound as a colorless oil (12 mg). MS (m/e)=450.2 (MH$^+$).

Example 103

3-(2,4-Dichloro-phenyl)-1,1,1-trifluoro-2-(2-methoxy-pyrimidin-5-yl)-butan-2-ol

The title compound was prepared in analogy to Example 1, steps 2 to 5, from 2,4-dichloro-benzeneacetic acid methyl ester [CAS Reg. No. 55954-23-9] and 2-methoxy-5-pyrimidinecarboxylic acid [CAS Reg. No. 344325-95-7]. MS (neg. ion, m/e)=379.1 ((M–H)$^-$).

Example 104

3-(2-Chloro-4-methoxy-phenyl)-1,1,1-trifluoro-2-pyridin-4-yl-butan-2-ol

The title compound was prepared in analogy to Example 1, steps 2 to 5, from 2-chloro-4-methoxy-benzeneacetic acid methyl ester [CAS Reg. No. 847604-18-6] and 4-pyridinecarboxylic acid [CAS Reg. No. 55-22-1]. MS (m/e)=346.1 (MH$^+$).

Example 105

3-Chloro-4-(3,3,3-trifluoro-2-hydroxy-1-methyl-2-pyridin-4-yl-propyl)-phenol

The title compound was prepared in analogy to Example 72 from 3-(2-chloro-4-methoxy-phenyl)-1,1,1-trifluoro-2-pyri-

Example 106

3-(2-Chloro-4-methoxy-phenyl)-1,1,1-trifluoro-2-(3-isopropyl-3H-benzotriazol-5-yl)-butan-2-ol The title compound was prepared in low yield in analogy to Example 1, steps 2 to 5, from 2-chloro-4-methoxy-benzene-acetic acid methyl ester [CAS Reg. No. 847604-18-6] and 1-(1-methylethyl)-1H-benzotriazole-5-carboxylic acid [CAS Reg. No. 306935-41-1]. MS (m/e)=428.2 (MH$^+$).

Example 107

3-(2-Chloro-4-methoxy-phenyl)-2-cinnolin-4-yl-1,1,1-trifluoro-butan-2-ol

The title compound was prepared in low yield in analogy to Example 1, steps 2 to 5, from 2-chloro-4-methoxy-benzene-acetic acid methyl ester [CAS Reg. No. 847604-18-6] and cinnoline-4-carbocylic acid [CAS Reg. No. 21905-86-2]. MS (m/e)=397.1 (MH$^+$).

Example 108

3-Chloro-4-(2-cinnolin-4-yl-3,3,3-trifluoro-2-hydroxy-1-methyl-propyl)-phenol The title compound was prepared in analogy to Example 72 from 3-(2-chloro-4-methoxy-phenyl)-2-cinnolin-4-yl-1,1,1-trifluoro-butan-2-ol (Example 107) by treatment with aqueous HBr. MS (m/e)=383.2 (MH$^+$).

Example 109

3-(2-Chloro-4-methoxy-phenyl)-1,1,1-trifluoro-2-pyrazolo[1,5-a]pyridin-3-yl-butan-2-ol The title compound was prepared in low yield in analogy to Example 1, steps 2 to 5, from 2-chloro-4-methoxy-benzene-acetic acid methyl ester [CAS Reg. No. 847604-18-6] and pyrazolo[1,5-a]pyridine-3-carboxylic acid [CAS Reg. No. 16205-46-2]. MS (m/e)=385.1 (MH$^+$).

Example 110

3-Chloro-4-(3,3,3-trifluoro-2-hydroxy-1-methyl-2-pyrazolo[1,5-a]pyridin-3-yl-propyl)-phenol The title compound was prepared in analogy to Example 72 from 3-(2-chloro-4-methoxy-phenyl)-1,1,1-trifluoro-2-pyrazolo[1,5-a]pyridin-3-yl-butan-2-ol (Example 109) by treatment with aqueous HBr. MS (m/e)=371.1 (MH$^+$).

Example 111

2-(2-Chloro-pyridin-4-yl)-3-{2-chloro-4-[3-((1H)-tetrazol-5-yl)-propoxy]-phenyl}-1,1,1-trifluoro-butan-2-ol

Step 1: 2-(2-Chloro-pyridin-4-yl)-3-{2-chloro-4-[3-(1-trityl-(1H)-tetrazol-5-yl)-propoxy]-phenyl}-1,1,1-trifluoro-butan-2-ol To a suspension of K$_2$CO$_3$ (93 mg), KI (90 mg) in N-methyl-2-pyrrolidone (0.5 mL) were added 5-(3-chloropropyl)-1-(triphenylmethyl)-1H-tetrazole (137 mg, CAS 823797-34-8, preparation see Bosmans et al., WO2005003124 A1, page 23) and 3-chloro-4-[2-(2-chloro-pyridin-4-yl)-3,3,3-trifluoro-2-hydroxy-1-methyl-propyl]-phenol (99 mg, Example 133). The mixture was heated to 60° C. for 20 hours and TLC confirmed almost complete conversion. The mixture was allowed to cool and poured into water. The aqueous layer was extracted with ethyl acetate and the organic extracts were washed with brine, dried and evaporated. The residue was purified by flash chromatography (silica gel, gradient of ethyl acetate in heptane) to give the title compound as a colorless solid (100 mg). MS (neg. ion, m/e)=716.2 ((M–H)$^-$).

Step 2: 2-(2-Chloro-pyridin-4-yl)-3-{2-chloro-4-[3-((1H)-tetrazol-5-yl)-propoxy]-phenyl}-1,1,1-trifluoro-butan-2-ol 2-(2-Chloro-pyridin-4-yl)-3-{2-chloro-4-[3-(1-trityl-(1H)-tetrazol-5-yl)-propoxy]-phenyl}-1,1,1-trifluoro-butan-2-ol (80 mg, from previous step) was dissolved in CH$_2$Cl$_2$ (2.5 mL). To the solution was added trifluoroacetic acid (1.25 mL) at RT and the mixture was allowed to stir for 48 hours; almost complete conversion was observed. The reaction mixture was concentrated in vacuo and diluted with ethyl acetate and water. The layers were separated and the organic extracts were washed with brine, dried over Na$_2$SO$_4$ and evaporated. The residue was purified by flash chromatography (silica gel, gradient of ethyl acetate in heptane) to give the desired compounds as a white solid (46 mg). MS (m/e)=476.1 (MH$^+$).

Example 112

3-(2-Chloro-4-hydroxymethyl-phenyl)-2-(2-chloro-pyridin-4-yl)-1,1,1-trifluoro-butan-2-ol 3-Chloro-4-[2-(2-chloro-pyridin-4-yl)-3,3,3-trifluoro-2-hydroxy-1-methyl-propyl]-benzoic acid methyl ester (488 mg, Example 135) was dissolved in CH$_2$Cl$_2$ under argon. The solution was cooled to –15° C. in an ice/salt bath and a solution of DIBAL-H (1M in CH$_2$Cl$_2$, 3 mL) was added drop wise. Stirring was continued and the mixture was allowed to warm to 0° C. over a period of 2 hours. The mixture was then poured into ice/water and extracted with ethyl acetate. The organic extracts were washed with brine, dried over Na$_2$SO$_4$ and evaporated. The residue was purified by flash chromatography (silica gel, gradient of ethyl acetate in heptane) to give the title compound as a colorless solid (200 mg). MS (m/e)=380.1 (MH$^+$).

Example 113

{3-Chloro-4-[2-(2-chloro-pyridin-4-yl)-3,3,3-trifluoro-2-hydroxy-1-methyl-propyl]-phenyl}-acetic acid

Step 1: Methanesulfonic acid 3-chloro-4-[2-(2-chloro-pyridin-4-yl)-3,3,3-trifluoro-2-hydroxy-1-methyl-propyl]-benzyl ester To a solution of 3-(2-chloro-4-hydroxymethyl-phenyl)-2-(2-chloro-pyridin-4-yl)-1,1,1-trifluoro-butan-2-ol (50 mg, Example 112) in THF (1 mL) was added NEt$_3$ (30 mg, 0.03 mL) under argon at –10° C. Methanesulfonyl chloride (18 mg, 0.01 mL) was added and the mixture was allowed to stir for 30 minutes. The reaction mixture was diluted with ethyl acetate and washed successively with sat. KHCO$_3$ solution and brine. The organic layer was dried over Na$_2$SO$_4$ and evaporated to give the desired compound as light yellow, viscous oil that was used without further purification (53 mg). MS (m/e)=358.1 (MH$^+$).

Step 2: {3-Chloro-4-[2-(2-chloro-pyridin-4-yl)-3,3,
3-trifluoro-2-hydroxy-1-methyl-propyl]-phenyl}-
acetonitrile Methanesulfonic acid 3-chloro-4-[2-(2-chloro-pyridin-4-yl)-3,3,3-trifluoro-2-hydroxy-1-methyl-propyl]-benzyl ester (66 mg) was dissolved in DMF at RT under argon. Sodium cyanide (18 mg) was added and the mixture was warmed to 85° C. and allowed to stir for 1.5 hours. The mixture was diluted with ethyl acetate and washed with water and brine.

The organic extracts were dried over $Na_2SO_4$ and evaporated. The residue was purified by flash chromatography (silica gel, gradient of ethyl acetate in heptane) to give the desired compound as a colorless solid (34 mg). MS (m/e)= 389.1 (MH$^+$).

Step 3: {3-Chloro-4-[2-(2-chloro-pyridin-4-yl)-3,3,
3-trifluoro-2-hydroxy-1-methyl-propyl]-phenyl}-
acetic acid {3-Chloro-4-[2-(2-chloro-pyridin-4-yl)-3,3,3-trifluoro-2-hydroxy-1-methyl-propyl]-phenyl}-acetonitrile was suspended in aq. conc. HCl (3 mL) and stirred for 1 hour at 80° C. The mixture was allowed to cool and poured into water. The pH of the solution was adjusted to 6-7 with diluted NaOH. The aqueous layer was extracted three times with ethyl acetate and the extracts were dried over $Na_2SO_4$ and evaporated. The residue was purified by flash chromatography (silica gel, gradient of ethyl acetate in heptane) to give the title compound as a colorless solid (16 mg). MS (m/e)=408.1 (MH$^+$).

Example 114

3-{3-Chloro-4-[2-(2-chloro-pyridin-4-yl)-3,3,3-trif-
luoro-2-hydroxy-1-methyl-propyl]-phenyl}-propi-
onic acid Step 1: 2-{3-Chloro-4-[2-(2-chloro-pyridin-4-yl)-3,
3,3-trifluoro-2-hydroxy-1-methyl-propyl]-benzyl}-
malonic acid diethyl ester Sodium hydride (60% in mineral oil, 165 mg) was suspended in THF (2 mL) under argon at RT. Diethylmalonic acid (165 mg, 0.12 mL) was added and the mixture was stirred at 50° C. for 60 minutes. Some bubbling was observed. A solution of methanesulfonic acid 3-chloro-4-[2-(2-chloro-pyridin-4-yl)-3,3,3-trifluoro-2-hydroxy-1-methyl-propyl]-benzyl ester (520 mg, obtained in Example 113, step 1) in THF (3 mL) was then added. The resulting yellow solution was refluxed for 40 minutes; full conversion was confirmed by TLC analysis after that time. The reaction mixture was poured into water and extracted with ethyl acetate. The organic extracts were washed with brine, dried over $Na_2SO_4$ and evaporated. The residue was purified by flash chromatography (silica gel, gradient of ethyl acetate in heptane) to give the title compound as a colorless solid (214 mg). MS (m/e)= 522.2 (MH$^+$).

Step 2: 3-{3-Chloro-4-[2-(2-chloro-pyridin-4-yl)-3,
3,3-trifluoro-2-hydroxy-1-methyl-propyl]-phenyl}-
propionic acid ethyl ester To a mixture of 2-{3-chloro-4-[2-(2-chloro-pyridin-4-yl)-3,3,3-trifluoro-2-hydroxy-1-methyl-propyl]-benzyl}-malonic acid diethyl ester (214 mg) and NaCl (29 mg) in DMSO (4 mL) was added a small amount of water (0.011 mL). The mixture was then heated to 140° C. for 7 days. The mixture was poured into water and extracted with ethyl acetate. The organic extracts were washed with brine, dried over $Na_2SO_4$ and evaporated. The residue was purified by flash chromatography (silica gel, gradient of ethyl acetate in heptane) to give the title compound as a colorless, viscous oil (127 mg). MS (m/e)=450.1 (MH$^+$).

Step 3: 3-{3-Chloro-4-[2-(2-chloro-pyridin-4-yl)-3,
3,3-trifluoro-2-hydroxy-1-methyl-propyl]-phenyl}-
propionic acid 3-{3-Chloro-4-[2-(2-chloro-pyridin-4-yl)-3,3,3-trifluoro-2-hydroxy-1-methyl-propyl]-phenyl}-propionic acid ethyl ester (118 mg) was dissolved in THF (1 mL). To the solution was added 1M aq. NaOH (1 mL) to give a cloudy, light yellow mixture. The reaction was allowed to stir at RT for 2.5 hours; a clear solution was obtained at that time. Water was added and the pH was adjusted to pH=3 with dilute aqueous HCl. A colorless precipitate was formed. The mixture was extracted with ethyl acetate and the organic extracts were washed with brine, dried over $Na_2SO_4$ and evaporated. The title compound was obtained as a colorless solid (78 mg). MS (neg. ion, m/e)=420.1 (M−H)$^-$.

Example 115

3-(2-Chloro-5-methoxy-phenyl)-2-(2-chloro-pyridin-
4-yl)-1,1,1-trifluoro-butan-2-ol Step 1: 2-Chloro-5-methoxy-benzeneacetic acid
methyl ester 2-Chloro-5-methoxy-benzeneacetic acid (10 g, CAS Reg. No. 91367-10$^{-1}$) was dissolved in MeOH (210 mL) and $H_2SO_4$ (0.7 mL) was added. The mixture was then refluxed over night. Methanol was removed in vacuo and the residue was dissolved in ethyl acetate. The organic layer was washed with sat. $NaHCO_3$ and brine, dried over $Na_2SO_4$ and evaporated. The title compound was obtained as a light brown oil (10.16 g) and was used without further purification. $^1$H-NMR, (CDCl$_3$): 7.27 (d, 1H), 6.83 (d, 1H), 6.77 (dd, 1H), 3.79 (s, 3H), 3.74 (s, 2H), 3.72 (s, 3H).

Step 2: 2-(2-Chloro-5-methoxy-phenyl)-propionic
acid methyl ester

2-Chloro-5-methoxy-benzeneacetic acid methyl ester (994 mg) was dissolved in THF and cooled to −78° C. Lithiumdiisopropylamide (2M in THF, 3.72 mL) was added drop wise and stirring was continued for 30 minutes. Iodomethane (879 mg, 0.39 mL) was added and stirring was continued for 30 minutes. The cooling bath was removed and the reaction was allowed to warm for 45 minutes. The mixture was poured into water and extracted with ethyl acetate. The organic extract was washed with brine, dried over $Na_2SO_4$ and evaporated. The residue was purified by flash chromatography (silica gel, ethyl acetate:heptane 1:3) to give the desired compound as a yellow oil (859 mg). $^1$H-NMR, (CDCl$_3$): 7.27 (d, 1H), 6.85 (d, 1H), 6.74 (dd, 1H), 4.17 (q, 1H), 3.78 (s, 3H), 3.69 (s, 3H), 1.48 (d, 3H).

Step 3:
2-(2-Chloro-5-methoxy-phenyl)-propionaldehyde 2-(2-Chloro-5-methoxy-phenyl)-propionic acid methyl ester (850 mg) was dissolved in toluene (40 mL) and cooled to −78° C. Diisobutylaluminium hydride (20% in toluene, 3.69 mL) was added over a period of 15 minutes. Stirring was continued for 45 minutes at −78° C. Methanol (2 mL) was added and then 1N potassium sodium tartrate solution (10 mL). The cooling bath was removed and the mixture was allowed to warm to RT. The mixture was diluted with water and extracted with ethyl acetate. The organic layer was washed with brine, dried over $Na_2SO_4$ and evaporated. The title compound was obtained as a light yellow oil (710 mg) and was used without further purification. $^1$H-NMR, ($CDCl_3$): 9.72 (s, 1H), 7.34 (d, 1H), 6.79 (dd, 1H), 6.66 (d, 1H), 4.10 (q, 1H), 3.79 (s, 3H), 1.43 (d, 3H).

Step 4: 2-(2-Chloro-5-methoxy-phenyl)-1-(2-chloro-pyridin-4-yl)-propan-1-ol

2-Chloro-4-iodopyridine (1.03 g, CAS Reg. No. 153034-86-7) was dissolved in THF (50 mL) and a solution of isopropylmagnesiumchloride-lithium chloride complex (14% in THF, 3.13 mL) was added at RT over 3 minutes. The mixture was cooled in an ice bath and 2-(2-chloro-5-methoxy-phenyl)-propionaldehyde (710 mg) dissolved in THF (20 mL) was added drop wise over a period of 10 minutes. Stirring was continued for 1.5 hours. The reaction mixture was poured into water, extracted with ethyl acetate and the organic layer was washed with brine, dried over $Na_2SO_4$ and evaporated. The residue was purified by flash chromatography (silica gel, gradient of ethyl acetate in heptane) to give the desired compound as a yellow oil (734 mg). MS (m/e)=312.0 (MH$^+$).

Step 5: 2-(2-Chloro-5-methoxy-phenyl)-1-(2-chloro-pyridin-4-yl)-propan-1-one 2-(2-Chloro-5-methoxy-phenyl)-1-(2-chloro-pyridin-4-yl)-propan-1-ol (140 mg) was dissolved in $CH_2Cl_2$ (20 mL). To this solution was added 3 Å molecular sieves (140 mg) and then tetrapropylammonium perruthenate (15.8 mg) and 4-methyl-morpholine-4-oxide (121 mg). The mixture was allowed to stir for 2 hours. The reaction mixture was applied directly to a silica gel column and the column was eluted with ethyl acetate:heptane 3:7. The appropriate fractions were combined and evaporated to give the title compound as a colorless gum (113 mg). MS (neg. ion, m/e)=308.4 ((M−H)$^-$).

Step 6: 3-(2-Chloro-5-methoxy-phenyl)-2-(2-chloro-pyridin-4-yl)-1,1,1-trifluoro-butan-2-ol This material was obtained in analogy to example 1, step 5 from 2-(2-chloro-5-methoxy-phenyl)-1-(2-chloro-pyridin-4-yl)-propan-1-one (110 mg) by treatment with trifluoromethyltrimethylsilane (2N in THF, 0.39 mL) and tetrabutylammonium fluoride trihydrate (78 mg). The title compound was obtained as a colorless gum (70 mg). MS (m/e)=380.1 (MH$^+$).

Example 116

4-Chloro-3-[2-(2-chloro-pyridin-4-yl)-3,3,3-trifluoro-2-hydroxy-1-methyl-propyl]-phenol 3-(2-Chloro-5-methoxy-phenyl)-2-(2-chloro-pyridin-4-yl)-1,1,1-trifluoro-butan-2-ol (Example 115, 293 mg) was dissolved in $CH_2Cl_2$ (30 mL) and cooled to 0° C. A solution of boron tribromide (1M in $CH_2Cl_2$, 3.08 mL) was added drop wise and stirring was continued at 0° C. for 1 hour. The reaction mixture was diluted with $CH_2Cl_2$, extracted with sat. $NaHCO_3$ solution and brine, dried over $Na_2SO_4$ and evaporated. The residue was purified by flash chromatography (silica gel, ethyl acetate in heptane 3:7) to give the title compound as a colorless solid (230 mg). MS (m/e)=366.0 (MH$^+$).

Example 117

3-(2,4-Dichloro-phenyl)-5,5,5-trifluoro-4-hydroxy-4-(6-methyl-pyrazin-2-yl)-pentanoic acid methyl ester The title compound was prepared in analogy to Example 1, steps 2 to 5, from 2,4-dichlorobenzeneacetic acid methyl ester [CAS Reg. No. 91361-41-0] and 6-methyl-2-pyrazinecarboxylic acid [CAS Reg. No. 5521-61-9], which was made from 2,6-dimethylpyrazine following a procedure from Vishweshwar et al.; *J. Org. Chem.* 2002, 2, 556. In step 4, bromo-acetic acid methyl ester was used as an alkylating agent and the following improved procedure was used: after addition of NaH at r.t. the reaction mixture was stirred at 45° C. for 3 h. After cooling down to 5° C., bromo-acetic acid methyl ester was added and the reaction mixture was stirred at 35° C. for 3 h, poured onto ice-water and extracted with ethyl acetate. MS (m/e)=423.1 [MH$^+$].

Example 118

3-(2,4-Dichloro-phenyl)-5,5,5-trifluoro-4-hydroxy-4-(6-methyl-pyrazin-2-yl)-pentanoic acid 3-(2,4-Dichloro-phenyl)-5,5,5-trifluoro-4-hydroxy-4-(6-methyl-pyrazin-2-yl)-pentanoic acid methyl ester (Example 117, 42 mg) was dissolved in MeOH (1 mL), treated with a 1N NaOH aqueous solution (0.2 ml) and stirred at 40° C. for 5 h. The MeOH was evaporated in vacuo and a 1N HCl aqueous solution (0.2 ml) was added. The resulting suspension was extracted twice with ethyl acetate. The combined organic layer were washed with water and brine, dried over magnesium sulfate and evaporated. The residue was purified by flash chromatography (silica gel, ethyl acetate in heptane 2:1) to give the title compound as a colorless semisolid (30 mg). MS (m/e)=409.3 (MH$^+$).

Example 119

4-[2-(2,4-Dichloro-phenyl)-1-hydroxy-1-trifluoromethyl-propyl]-1H-pyridin-2-one

The title compound was prepared in analogy to Example 1, steps 2 to 5, from 2,4-dichlorobenzeneacetic acid methyl ester [CAS Reg. No. 91361-41-0] and 2-benzyloxy-isonicotinic acid (which was made as described below from 2-chloro isonicotinic acid), leading to 2-(2-benzyloxy-pyridin-4-yl)-3-(2,4-dichloro-phenyl)-1,1,1-trifluoro-butan-2-ol, followed by cleavage of the benzyl protecting group by hydrogenation over Pd/C-10% (0.75 g) in ethyl actetate (150 ml). In step 4, methyl iodide was used as an alkylating agent and the improved procedure described in example 117 was used. MS (m/e)=364.0 [MH$^+$].

Preparation of 2-Benzyloxy-isonicotinic acid

2-Chloro isonicotinic acid (9.45 g) and benzyl alcohol (12.977 g) were dissolved in NMP (180 mL), and treated with tBuOK (20.2 g) between 10-25° C. The reaction mixture was then stirred at 125° C. (Bath-temperature) for 6 h, cooled down to r.t., poured into water (1500 ml) and extracted twice with water. The combined aqueous phases were treated with concentrated aqueous HCl until pH 3 (16 ml). After 10 min

Example 120

{4-[2-(2,4-Dichloro-phenyl)-1-hydroxy-1-trifluoromethyl-propyl]-pyridin-2-yloxy}-acetic acid methyl ester 4-[2-(2,4-Dichloro-phenyl)-1-hydroxy-1-trifluoromethyl-propyl]-1H-pyridin-2-one (Example 119, 158 mg) was dissolved in toluene (5 mL), and treated with bromo-acetic acid methyl ester (0.03 mL) and silver carbonate (53 mg). The reaction mixture was then stirred at 145° C. (Bath-temperature) for 3.5 h, cooled down to r.t., filtered-off and concentrated in vacuo. The residue was purified by flash chromatography (10 g silica gel, ethyl acetate/heptane 1:9) to give the title compound as colorless oil (30 mg). MS (m/e)=438.3 (MH$^+$).

Example 121

{4-[2-(2,4-Dichloro-phenyl)-1-hydroxy-1-trifluoromethyl-propyl]-2-oxo-2H-pyridin-1-yl}-acetic acid methyl ester 4-[2-(2,4-Dichloro-phenyl)-1-hydroxy-1-trifluoromethyl-propyl]-1H-pyridin-2-one (Example 119, 100 mg) was dissolved in THF (10 mL), and treated with t-BuOK (34 mg). After 5 minutes stirring, bromo-acetic acid methyl ester (0.03 mL) was added and the reaction mixture was stirred at 55° C. for 17 h. The reaction mixture was then cooled down to r.t., poured into water (50 mL) and extracted twice with ethyl acetate. The combined organic phases were washed with brine, dried over MgSO$_4$ and concentrated in vacuo. The residue was purified by flash chromatography (10 g silica gel, ethyl acetate/heptane 30:70) to give the title compound as colorless waxy solid (49 mg). MS (m/e)=438.1 (MH$^+$).

Example 122

{4-[2-(2,4-Dichloro-phenyl)-1-hydroxy-1-trifluoromethyl-propyl]-2-oxo-2H-pyridin-1-yl}-acetic acid {4-[2-(2,4-Dichloro-phenyl)-1-hydroxy-1-trifluoromethyl-propyl]-2-oxo-2H-pyridin-1-yl}-acetic acid methyl ester (Example 121, 40 mg) was dissolved in MeOH (1 mL), and treated with 1N NaOH (0.183 mL). The reaction mixture was stirred at 55° C. (Bath temperature) for 2 h. The reaction mixture was then cooled down to r.t., pH adjusted to pH2 by addition of 1N aqueous HCl, and the MeOH evaporated in vacuo. The resulting suspension was then extracted twice with ethyl acetate, the combined organic phases washed with brine, dried over MgSO$_4$ and concentrated in vacuo, leading to the title compound as off-white solid (33 mg). MS (m/e)=424.1 (MH$^+$).

Example 123

2-{4-[2-(2,4-Dichloro-phenyl)-1-hydroxy-1-trifluoromethyl-propyl]-pyridin-2-yloxy}-acetamide The title compound was prepared in analogy to Example 120 from 4-[2-(2,4-dichloro-phenyl)-1-hydroxy-1-trifluoromethyl-propyl]-1H-pyridin-2-one (Example 119, 100 mg) and 2-bromo-acetamide (45 mg). MS (m/e)=423.1 (MH$^+$).

Example 124

3-(2,4-Dichloro-phenyl)-1,1,1-trifluoro-2-[2-(2-methoxy-ethoxy)-pyridin-4-yl]-butan-2-ol The title compound was prepared in analogy to Example 120 from 4-[2-(2,4-Dichloro-phenyl)-1-hydroxy-1-trifluoromethyl-propyl]-1H-pyridin-2-one (Example 119, 100 mg) and 1-bromo-2-methoxy-ethane (0.031 mL). MS (m/e)=423.1 (MH$^+$).

Example 125

{4-[2-(2,4-Dichloro-phenyl)-1-hydroxy-1-trifluoromethyl-propyl]-pyridin-2-yloxy}-acetonitrile The title compound was prepared in analogy to Example 120 from 4-[2-(2,4-Dichloro-phenyl)-1-hydroxy-1-trifluoromethyl-propyl]-1H-pyridin-2-one (Example 119, 100 mg) and bromo-acetonitrile (0.022 mL). MS (m/e)=405.2 (MH$^+$).

Example 126

3-(2,4-Dichloro-phenyl)-1,1,1-trifluoro-2-[2-(2-hydroxy-ethoxy)-pyridin-4-yl]-butan-2-ol {4-[2-(2,4-Dichloro-phenyl)-1-hydroxy-1-trifluoromethyl-propyl]-pyridin-2-yloxy}-acetic acid methyl ester (Example 120, 70 mg) was dissolved in THF (5 mL) and treated with LiBH$_4$ (10 mg). After 2 h stirring at 45° C. another portion of LiBH4 (5 mg) was added and the reaction mixture further stirred at 45° C. for 2 h. After cooling down to r.t., 3 drops of 1N aqueous HCl were added, followed by water (5 mL). The reaction mixture was then extracted twice with ethyl acetate. The combined organic phases were washed with brine, dried over MgSO$_4$ and concentrated in vacuo. The residue was purified by flash chromatography (10 g silica gel, ethyl acetate/heptane 30:70) to give the title compound as colorless foam (52 mg). MS (m/e)=410.3 (MH$^+$).

Example 127

2-{4-[2-(2,4-Dichloro-phenyl)-1-hydroxy-1-trifluoromethyl-propyl]-pyridin-2-yloxy}-1-morpholin-4-yl-ethanone Step 1: Preparation of {4-[2-(2,4-Dichloro-phenyl)-1-hydroxy-1-trifluoromethyl-propyl]-pyridin-2-yloxy}-acetic acid {4-[2-(2,4-Dichloro-phenyl)-1-hydroxy-1-trifluoromethyl-propyl]-pyridin-2-yloxy}-acetic acid methyl ester (Example 120, 190 mg) was dissolved in MeOH (3 mL), and treated with 1N NaOH (0.87 mL). The reaction mixture was stirred at 55° C. (Bath temperature) for 2 h. The reaction mixture was then cooled down to r.t., pH adjusted to pH2 by addition of 1N aqueous HCl, and the MeOH evaporated in vacuo. The resulting suspension was then extracted twice with ethyl acetate, the combined organic phases washed with brine, dried over MgSO$_4$ and concentrated in vacuo, leading to the title compound as light yellow amorphous solid (180 mg). MS (m/e)=424.1 (MH$^+$).

Step 2: 2-{4-[2-(2,4-Dichloro-phenyl)-1-hydroxy-1-trifluoromethyl-propyl]-pyridin-2-yloxy}-1-morpholin-4-yl-ethanone {4-[2-(2,4-Dichloro-phenyl)-1-hydroxy-1-trifluoromethyl-propyl]-pyridin-2-yloxy}-acetic acid (180 mg) and morpholin (0.04 mL) in DMF (6 mL), were treated with 4-methyl-morpholine (0.140 mL) and HBTU (241 mg). The reaction mixture was stirred at r.t. for 17 h. The reaction mixture was diluted with water (50 mL) and extracted twice with ethyl acetate. The combined organic phases were washed with brine, dried over $MgSO_4$ and concentrated in vacuo. The residue was purified by flash chromatography (10 g silica gel, ethyl acetate/heptane 70:30) to give the title compound as white solid (134 mg). MS (m/e)=492.9 ($MH^+$).

Example 128

4-[2-(2,4-Dichloro-phenyl)-4,4,4-trifluoro-3-hydroxy-3-(6-methyl-pyrazin-2-yl)-butyl]-benzoic acid ethyl ester The title compound was prepared in analogy to Example 1, steps 2 to 5, from 2,4-dichlorobenzeneacetic acid methyl ester [CAS Reg. No. 91361-41-0] and 6-methyl-2-pyrazinecarboxylic acid [CAS Reg. No. 5521-61-9], which was made from 2,6-dimethylpyrazine following a procedure from Vishweshwar et al.; J. Org. Chem. 2002, 2, 556. In step 4, 4-bromomethyl-benzoic acid ethyl ester was used as an alkylating agent and the improved procedure described in Example 117 was used. MS (m/e)=513.3 [$MH^+$].

Example 129

4-[2-(2,4-Dichloro-phenyl)-4,4,4-trifluoro-3-hydroxy-3-(6-methyl-pyrazin-2-yl)-butyl]-benzoic acid The title compound was prepared in analogy to Example 118, from 4-[2-(2,4-dichloro-phenyl)-4,4,4-trifluoro-3-hydroxy-3-(6-methyl-pyrazin-2-yl)-butyl]-benzoic acid ethyl ester (Example 128, 274 mg) as an off-white solid (165 mg). MS (m/e)=483.3 ($MH^+$).

Example 130

4-Chloro-3-[3,3,3-trifluoro-2-hydroxy-1-methyl-2-(6-methyl-pyrazin-2-yl)-propyl]-benzoic acid methyl ester The title compound was prepared in analogy to Example 1, steps 2 to 5, from 4-Chloro-3-methoxycarbonylmethyl-benzoic acid methyl ester [CAS Reg. No. 600047-41-8] and 6-methyl-2-pyrazinecarboxylic acid [CAS Reg. No. 5521-61-9], which was made from 2,6-dimethylpyrazine following a procedure from Vishweshwar et al.; J. Org. Chem. 2002, 2, 556. In step 4, methyl iodide was used as an alkylating agent and the improved procedure described in Example 117 was used. MS (m/e)=389.4 [$MH^+$].

Example 131

4-Chloro-3-[3,3,3-trifluoro-2-hydroxy-1-methyl-2-(6-methyl-pyrazin-2-yl)-propyl]-benzoic acid The title compound was prepared in analogy to Example 118, from 4-chloro-3-[3,3,3-trifluoro-2-hydroxy-1-methyl-2-(6-methyl-pyrazin-2-yl)-propyl]-benzoic acid methyl ester (Example 130, 50 mg) as an white solid (47 mg). MS (m/e)=373.1 ($MH^+$).

Example 132

3-(2-Chloro-4-methoxy-phenyl)-2-(2-chloro-pyridin-4-yl)-1,1,1-trifluoro-butan-2-ol The title compound can be prepared in analogy to Example 1, steps 2 to 5, from (2-chloro-5-methoxy-phenyl)-acetic acid methyl ester [CAS Reg. No. 90919-41-8] and 2-chloro-isonicotinic acid methyl ester.

Alternatively, steps 2 and 3 can also be replaced by the following improved one-step procedure:
2-Chloro-N-methoxy-N-methyl-isonicotinamide [CAS Reg. No. 250263-39-9] (24.6 g) and 1-bromomethyl-2-chloro-4-methoxy-benzene [CAS Reg. No. 54788-17-9] (34.7 g) were dissolved in THF (720 ml), cooled down to −72° C. and treated over a period of 1.3 h with 1.6 M n-BuLi in n-hexane without exceeding −70° C. The reaction mixture was stirred at −72° C. for 15 min, warmed up to −20° C. (duration: 35 min) and treated with saturated aqueous $NH_4Cl$ (400 ml). After 5 min the reaction mixture was extracted twice with ethyl acetate. The combined organic phases were washed with sat aq $NH_4Cl$, dried over $MgSO_4$, filtered off and concentrated in vacuo to yield an orange oil (46.5 g). The residue was purified by flash chromatography (600 g silica gel, ethyl acetate in heptane 1:1) to give the title compound as orange viscous oil (17.1 g). MS (M−H, 294.2) In step 4, methyl iodide was used as an alkylating agent and the improved procedure described in Example 117 was used. MS (m/e)=378.4 [$MH^+$].

Example 133

3-Chloro-4-[2-(2-chloro-pyridin-4-yl)-3,3,3-trifluoro-2-hydroxy-1-methyl-propyl]-phenol 3-(2-Chloro-4-methoxy-phenyl)-2-(2-chloro-pyridin-4-yl)-1,1,1-trifluoro-butan-2-ol (Example 132, 48 mg) was dissolved in 48% aqueous HBr (0.9 m) and stirred at 105° C. (bath temperature) for 4 h. The reaction mixture was then poured on ice-water-brine and sat aq $NaHCO_3$ and extracted with ethyl acetate. The combined organic phases were washed with brine, dried over $MgSO_4$ and evaporated in vacuo. The resulting brown residue was purified by flash chromatography (8 g silica gel, ethyl acetate/heptane 1:4) to give the title compound as off-white semisolid (34 mg). MS (m/e)=364.0 (M−H).

Example 134

2-{3-Chloro-4-[2-(2-chloro-pyridin-4-yl)-3,3,3-trifluoro-2-hydroxy-1-methyl-propyl]-phenoxy}-2-methyl-propionamide 3-Chloro-4-[2-(2-chloro-pyridin-4-yl)-3,3,3-trifluoro-2-hydroxy-1-methyl-propyl]-phenol (Example 133, 200 mg) and 2-bromo-2-methyl-propionamide (272 mg) in dimethyl acetamide (1 mL) were treated with sodium hydroxide (66 mg) and stirred at r.t. for 17 h. A second portion of 2-bromo-2-methyl-propionamide (272 mg) followed by sodium hydroxide (66 mg) was added and the reaction mixture further stirred for 2 h at r.t. This process was repeated a last time and the reaction mixture was diluted with ice-water (10 mL), neutralized with 1N aqueous HCl, extracted with ethyl acetate (2×), dried over $MgSO_4$ and concentrated in vacuo.

Example 135

3-Chloro-4-[2-(2-chloro-pyridin-4-yl)-3,3,3-trifluoro-2-hydroxy-1-methyl-propyl]-benzoic acid methyl ester Step 1: Preparation of trifluoro-methanesulfonic acid 3-chloro-4-[2-(2-chloro-pyridin-4-yl)-3,3,3-trifluoro-2-hydroxy-1-methyl-propyl]-phenyl ester 3-Chloro-4-[2-(2-chloro-pyridin-4-yl)-3,3,3-trifluoro-2-hydroxy-1-methyl-propyl]-phenol (Example 133, 1.83 g) in dichloromethane (80 mL) was treated with triethyl amine (1.6 mL), cooled down to −20° C. and treated with trifluoromethane-sulfonic acid anhydride (0.99 mL) in 10 minutes. The reaction mixture was stirred at −20° C. for 15 min. and 1 h at r.t., followed by dilution with dichloromethane (80 mL). The organic phase was washed with water (2×) and brine, dried over $MgSO_4$ and concentrated in vacuo. The solid residue was stirred with a small amount of heptane/ethyl acetate, filtered and dried under high vacuum leading to the title compound as a light brown solid (1.97 g). MS (m/e)=498.0 ($MH^+$).

Step 2: Preparation of 3-Chloro-4-[2-(2-chloro-pyridin-4-yl)-3,3,3-trifluoro-2-hydroxy-1-methyl-propyl]-benzoic acid methyl ester Trifluoro-methanesulfonic acid 3-chloro-4-[2-(2-chloro-pyridin-4-yl)-3,3,3-trifluoro-2-hydroxy-1-methyl-propyl]-phenyl ester (1.9 g) in DMSO (19 mL) and MeOH (1.73 mL) was treated with palladium acetate (43 mg) and 1,3-bis(diphenyl-phosphino)propane (DPPP) (79 mg). Carbon monoxide was introduced in the reaction mixture for 10 minutes under agitation and the stirring was continued under CO atmosphere for another 3 h at 70° C. (bath-temperature). The dark reaction mixture was poured into ice-water (200 mL) and 1N aqueous HCl (24 mL), extracted twice with ethyl acetate. The combined organic phases were washed with brine (2×), dried over $MgSO_4$ and concentrated in vacuo. The residue was purified by flash chromatography (50 g silica gel, ethyl acetate: 25-30/heptane: 75-70) to give the title compound as white foam (924 mg). MS (m/e)=408.0 ($MH^+$).

Example 136

4-[2-(2-Chloro-4-methoxycarbonyl-phenyl)-1-hydroxy-1-trifluoromethyl-propyl]-pyridine-2-carboxylic acid methyl ester Formed as a By-Product During the Preparation of Example 135 (Step 2):

Starting from trifluoro-methanesulfonic acid 3-chloro-4-[2-(2-chloro-pyridin-4-yl)-3,3,3-trifluoro-2-hydroxy-1-methyl-propyl]-phenyl ester (1.9 g) the title compound was obtained as amorphous colorless solid (339 mg). MS (m/e)=432.1 ($MH^+$).

Example 137

3-Chloro-4-[2-(2-chloro-pyridin-4-yl)-3,3,3-trifluoro-2-hydroxy-1-methyl-propyl]-benzoic acid 3-Chloro-4-[2-(2-chloro-pyridin-4-yl)-3,3,3-trifluoro-2-hydroxy-1-methyl-propyl]-benzoic acid methyl ester (Example 135, 62 mg) in THF (1.5 mL) and MeOH (0.3 mL) was treated with 1M aqueous LiOH (0.228 mL) and stirred for 2 h at 65° C. (bath-temperature). The organic solvents were evaporated in vacuo and the residue was diluted with water (2 mL) and acidified with 1M aqueous HCl (0.3 mL). The precipitate was filtered and dried under high vacuum, leading to the title compound as white solid (54 mg). MS (m/e)=392.2 (M−H).

Example 138

4-[2-(4-Carboxy-2-chloro-phenyl)-1-hydroxy-1-trifluoromethyl-propyl]-pyridine-2-carboxylic acid The title compound was obtained in analogy to Example 137, from 4-[2-(2-chloro-4-methoxycarbonyl-phenyl)-1-hydroxy-1-trifluoromethyl-propyl]-pyridine-2-carboxylic acid methyl ester (Example 136, 100 mg). The compound was obtained as light yellow solid (58 mg). MS (m/e)=402.4 (M−H).

Example 139

3-(2-Chloro-4-methoxy-phenyl)-1,1,1-trifluoro-2-(2-iodo-pyridin-4-yl)-butan-2-ol 3-(2-Chloro-4-methoxy-phenyl)-2-(2-chloro-pyridin-4-yl)-1,1,1-trifluoro-butan-2-ol (Example 132, 0.38 g) in ethyl-methyl ketone (5 mL) was treated with sodium iodide (600 mg) and HI-57% (0.132 mL) and heated for 2.5 h under reflux. The reaction mixture was then concentrated in vacuo, diluted with water, and pH adjusted to 7 with a saturated aqueous $NaHCO_3$ solution. The mixture was extracted twice with ethyl acetate. The combined organic phases were washed with 0.5M sodium-thiosulfate and brine, dried over $MgSO_4$ and concentrated in vacuo. The residue was purified by flash chromatography (20 g silica gel, ethyl acetate/heptane 20:80) to give the title compound as white solid (375 mg). MS (m/e)=471.9 ($MH^+$).

Example 140

4-{4-[2-(2-Chloro-4-methoxy-phenyl)-1-hydroxy-1-trifluoromethyl-propyl]-pyridin-2-yl}-benzoic acid ethyl ester 3-(2-Chloro-4-methoxy-phenyl)-1,1,1-trifluoro-2-(2-iodo-pyridin-4-yl)-butan-2-ol (Example 139, 92 mg), 4-ethoxycarbonylphenylboronic acid (42 mg) and 1,1,bis(diphenylphosphino)ferrocenpalladium(II)dichloromethane in dioxane (0.7 mL) was treated with water (0.4 mL) and 2N—$Na_2CO_3$ (0.351 mL) and stirred at 80° C. under argon for 16 h. The reaction mixture was cooled down to r.t., diluted with ethyl acetate, washed with water and brine, dried over $MgSO_4$ and concentrated in vacuo. The residue was purified by flash chromatography (10 g silica gel, ethyl acetate/heptane 1:2) to give the title compound as light yellow amorphous material (78 mg). MS (m/e)=494.2 ($MH^+$).

Example 141

4-{4-[2-(2-Chloro-4-methoxy-phenyl)-1-hydroxy-1-trifluoromethyl-propyl]-pyridin-2-yl}-benzoic acid The title compound was obtained in analogy to Example 137, from 4-{4-[2-(2-chloro-4-methoxy-phenyl)-1-hydroxy-1-trifluoromethyl-propyl]-pyridin-2-yl}-benzoic acid ethyl ester (Example 140, 67 mg). The compound was obtained as white solid (44 mg). MS (m/e)=464.1 (M–H).

Example 142

3-{4-[2-(2-Chloro-4-methoxy-phenyl)-1-hydroxy-1-trifluoromethyl-propyl]-pyridin-2-yl}-benzoic acid methyl ester The title compound was obtained in analogy to Example 140, from 3-(2-chloro-4-methoxy-phenyl)-1,1,1-trifluoro-2-(2-iodo-pyridin-4-yl)-butan-2-ol (Example 139, 100 mg) and 3-methoxycarbonylphenylboronic acid (57 mg). The compound was obtained as colorless viscous oil (60 mg). MS (m/e)=480.1 (MH$^+$).

Example 143

3-{4-[2-(2-Chloro-4-methoxy-phenyl)-1-hydroxy-1-trifluoromethyl-propyl]-pyridin-2-yl}-benzoic acid The title compound was obtained in analogy to Example 137, from 3-{4-[2-(2-chloro-4-methoxy-phenyl)-1-hydroxy-1-trifluoromethyl-propyl]-pyridin-2-yl}-benzoic acid methyl ester (Example 142, 46 mg). The compound was obtained as white solid (39 mg). MS (m/e)=464.1 (M–H).

Example 144

3-(2-Chloro-4-fluoro-phenyl)-1,1,1-trifluoro-2-(2-iodo-pyridin-4-yl)-butan-2-ol

The title compound was obtained in analogy to Example 139, from 3-(2-chloro-4-fluoro-phenyl)-2-(2-chloro-pyridin-4-yl)-1,1,1-trifluoro-butan-2-ol (Example 34, 800 mg). The compound was obtained as light yellow solid (786 mg). MS (m/e)=460.1 (MH$^+$).

Example 145

3-{4-[2-(2-Chloro-4-fluoro-phenyl)-1-hydroxy-1-trifluoromethyl-propyl]-pyridin-2-yl}-benzoic acid methyl ester The title compound was obtained in analogy to Example 140, from 3-(2-chloro-4-fluoro-phenyl)-1,1,1-trifluoro-2-(2-iodo-pyridin-4-yl)-butan-2-ol (Example 144, 97 mg) and 3-methoxycarbonylphenylboronic acid (57 mg). The compound was obtained as colorless viscous oil (82 mg). MS (m/e)=468.1 (MH$^+$).

Example 146

5-{4-[2-(2-Chloro-4-fluoro-phenyl)-1-hydroxy-1-trifluoromethyl-propyl]-pyridin-2-yl}-2-fluoro-benzonitrile The title compound was obtained in analogy to Example 140, from 3-(2-chloro-4-fluoro-phenyl)-1,1,1-trifluoro-2-(2-iodo-pyridin-4-yl)-butan-2-ol (Example 144, 120 mg) and 3-cyano-4-fluorophenylboronic acid (65 mg). The compound was obtained as colorless viscous oil (104 mg). MS (m/e)=453.1 (MH$^+$).

Example 147

3-{4-[2-(2-Chloro-4-fluoro-phenyl)-1-hydroxy-1-trifluoromethyl-propyl]-pyridin-2-yl}-benzoic acid The title compound was obtained in analogy to Example 137, from 3-{4-[2-(2-chloro-4-fluoro-phenyl)-1-hydroxy-1-trifluoromethyl-propyl]-pyridin-2-yl}-benzoic acid methyl ester (Example 145, 73 mg). The compound was obtained as white solid (32 mg). MS (m/e)=452.0 (M–H).

Example 148

4'-[2-(2-Chloro-4-trifluoromethanesulfonyloxy-phenyl)-1-hydroxy-1-trifluoromethyl-propyl]-3,4,5,6-tetrahydro-2H-[1,2']bipyridinyl-4-carboxylic acid ethyl ester Trifluoro-methanesulfonic acid 3-chloro-4-[2-(2-chloro-pyridin-4-yl)-3,3,3-trifluoro-2-hydroxy-1-methyl-propyl]-phenyl ester (Example 135-Step 1, 1.0 g) and piperidine-4-carboxylic acid ethyl ester (0.773 mL) in 1-methyl-2-pyrrolidon (10 mL) were heated at 220° C. in a microwave oven for 30 minutes. The reaction mixture was then diluted with water (100 mL), extracted twice with ethyl acetate. The combined organic phases were washed with brine, dried over MgSO$_4$ and concentrated in vacuo. The residue was purified by flash chromatography (70 g silica gel, heptane/acetic acid isopropylester 80/20 to 70/30) to give the title compound as light yellow viscous oil (119 mg). MS (m/e)=619.2 (MH$^+$).

Example 149

4'-[2-(2-Chloro-4-hydroxy-phenyl)-1-hydroxy-1-trifluoromethyl-propyl]-3,4,5,6-tetrahydro-2H-[1,2'] bipyridinyl-4-carboxylic acid The title compound was obtained in analogy to Example 137, from 4'-[2-(2-chloro-4-trifluoromethanesulfonyloxy-phenyl)-1-hydroxy-1-trifluoromethyl-propyl]-3,4,5,6-tetrahydro-2H-[1,2']bipyridinyl-4-carboxylic acid ethyl ester (Example 148, 89 mg). The compound was obtained as light yellow amorphous material (46 mg). MS (m/e)=457.2 (M–H).

Example 150

2-Chloro-5-{4-[2-(2-chloro-4-fluoro-phenyl)-1-hydroxy-1-trifluoromethyl-propyl]-pyridin-2-yl}-benzoic acid ethyl ester The title compound was obtained in analogy to Example 140, from 3-(2-chloro-4-fluoro-phenyl)-1,1,1-trifluoro-2-(2-iodo-pyridin-4-yl)-butan-2-ol (Example 144, 100 mg) and 4-chloro-3-(ethoxycarbonyl)phenylboronic acid (75 mg). The compound was obtained as colorless viscous oil (90 mg). MS (m/e)=516.3 (MH$^+$).

Example 151

5-{4-[2-(2-Chloro-4-fluoro-phenyl)-1-hydroxy-1-trifluoromethyl-propyl]-pyridin-2-yl}-2-fluoro-benzoic acid ethyl ester The title compound was obtained in analogy to Example 140, from 3-(2-chloro-4-fluoro-phenyl)-1,1,1-trifluoro-2-(2- iodo-pyridin-4-yl)-butan-2-ol (Example 144, 100 mg) and 3-ethoxycarbonyl-4-fluorophenylboronic acid (69 mg). The compound was obtained as colorless viscous oil (66 mg). MS (m/e)=500.1 (MH$^+$).

Example 152

5-{4-[2-(2-Chloro-4-fluoro-phenyl)-1-hydroxy-1-trifluoromethyl-propyl]-pyridin-2-yl}-2-fluoro-benzoic acid The title compound was obtained in analogy to Example 137, from 5-{4-[2-(2-chloro-4-fluoro-phenyl)-1-hydroxy-1-trifluoromethyl-propyl]-pyridin-2-yl}-2-fluoro-benzoic acid ethyl ester (Example 151, 56 mg). The compound was obtained as colorless viscous oil (40 mg). MS (m/e)=472.1 (M–H).

Example 153

2-Chloro-5-{4-[2-(2-chloro-4-fluoro-phenyl)-1-hydroxy-1-trifluoromethyl-propyl]-pyridin-2-yl}-benzoic acid The title compound was obtained in analogy to Example 137, from 2-chloro-5-{4-[2-(2-chloro-4-fluoro-phenyl)-1-hydroxy-1-trifluoromethyl-propyl]-pyridin-2-yl}-benzoic acid ethyl ester (Example 150, 79 mg). The compound was obtained as white solid (49 mg). MS (m/e)=488.2 (MH$^+$).

Example 154

4'-[2-(2-Chloro-4-methoxy-phenyl)-1-hydroxy-1-trifluoromethyl-propyl]-3,4,5,6-tetrahydro-2H-[1,2']bipyridinyl-4-carboxylic acid ethyl ester The title compound was obtained in analogy to Example 148, from 3-(2-chloro-4-methoxy-phenyl)-1,1,1-trifluoro-2-(2-iodo-pyridin-4-yl)-butan-2-ol (Example 139, 200 mg). The compound was obtained as light yellow amorphous solid (138 mg). MS (m/e)=501.1 (MH$^+$).

Example 155

4'-[2-(2-Chloro-4-methoxy-phenyl)-1-hydroxy-1-trifluoromethyl-propyl]-3,4,5,6-tetrahydro-2H-[1,2']bipyridinyl-4-carboxylic acid The title compound was obtained in analogy to Example 137, from 4'-[2-(2-chloro-4-methoxy-phenyl)-1-hydroxy-1-trifluoromethyl-propyl]-3,4,5,6-tetrahydro-2H-[1,2]bipyridinyl-4-carboxylic acid ethyl ester (Example 154, 58 mg). The compound was obtained as amorphous colorless solid (49 mg). MS (m/e)=471.1 (MH$^+$).

Example 156

4'-[2-(2-Chloro-4-ethoxy-phenyl)-1-hydroxy-1-trifluoromethyl-propyl]-3,4,5,6-tetrahydro-2H-[1,2']bipyridinyl-4-carboxylic acid Step 1: Preparation of 4'-[2-(2-chloro-4-hydroxyphenyl)-1-hydroxy-1-trifluoromethyl-propyl]-3,4,5,6-tetrahydro-2H-[1,2']bipyridinyl-4-carboxylic acid ethyl ester 4'-[2-(2-Chloro-4-methoxy-phenyl)-1-hydroxy-1-trifluoromethyl-propyl]-3,4,5,6-tetrahydro-2H-[1,2']bipyridinyl-4-carboxylic acid ethyl ester (Example 154, 57 mg) in dichloromethane (0.5 mL) under argon, was treated with 1M-BBr$_3$ in dichloromethane (0.341 mL). The solution was poured into ice-water/NaHCO$_3$, extracted twice with dichloromethane. The combined organic phases were washed with brine, dried over MgSO$_4$ and evaporated in vacuo. The residue was purified by flash chromatography (4 g silica gel, heptane/ethyl acetate 2/1) to give the title compound as amorphous colorless solid (41 mg). MS (m/e)=487.2 (MH$^+$).

Step 2: Preparation of 4'-[2-(2-chloro-4-ethoxy-phenyl)-1-hydroxy-1-trifluoromethyl-propyl]-3,4,5,6-tetrahydro-2H-[1,2']bipyridinyl-4-carboxylic acid ethyl ester 4'-[2-(2-Chloro-4-hydroxy-phenyl)-1-hydroxy-1-trifluoromethyl-propyl]-3,4,5,6-tetrahydro-2H-[1,2']bipyridinyl-4-carboxylic acid ethyl ester (Step 1, 31 mg) and silver carbonate (18 mg) in DMF (1 mL), were reacted with iodoethane (0.006 mL) and stirred at 80° C. for 17 h. The reaction mixture was poured into water (10 mL), and extracted twice with ethyl acetate. The combined organic phases were washed with brine, dried over MgSO$_4$ and evaporated in vacuo. The residue was purified by flash chromatography (4 g silica gel, heptane/ethyl acetate 2/1) to give the title compound as amorphous colorless solid (21 mg). MS (m/e)=515.3 (MH$^+$).

Step 3: Preparation of 4'-[2-(2-chloro-4-ethoxy-phenyl)-1-hydroxy-1-trifluoromethyl-propyl]-3,4,5,6-tetrahydro-2H-[1,2']bipyridinyl-4-carboxylic acid The title compound was obtained in analogy to Example 137, from 4'-[2-(2-chloro-4-ethoxy-phenyl)-1-hydroxy-1-trifluoromethyl-propyl]-3,4,5,6-tetrahydro-2H-[1,2]bipyridinyl-4-carboxylic acid ethyl ester (Step 2, 20 mg). The compound was obtained as amorphous light yellow solid (17 mg). MS (m/e)=485.5 (M–H).

Example 157

1,1,1-Trifluoro-3-(6-methoxy-4-methyl-pyridin-3-yl)-2-pyridin-4-yl-butan-2-ol

Step 1: 2-(6-Methoxy-4-methyl-pyridin-3-yl)-1-pyridin-4-yl-propan-1-one

5-Bromo-2-methoxy-4-methylpyridine ([CAS Reg. No. 164513-39-7], 202 mg) was added to caesium carbonate (488 mg), 4-propionylpyridine ([CAS Reg. No. 1701-69-5], 165 mg) and chloro(di-2-norbornylphosphino)(2-dimethylaminomethylferrocen-1-yl)palladium (II), ([CAS Reg. No. 614753-51-4], 11 mg) in dioxane (2 ml). The mixture was heated in a sealed tube to 120° C. over night. Purification by preparative HPLC (Phenomenex Gemini Axia-C18 column, solvent gradient 20-95% CH$_3$CN in 0.1% HCOOH[aq]) gave the title compound (30 mg). MS (m/e)=257.1 [M+H$^+$].

Step 2: 1,1,1-Trifluoro-3-(6-methoxy-4-methyl-pyridin-3-yl)-2-pyridin-4-yl-butan-2-ol This material was obtained in analogy to Example 1, step 5 from 2-(6-methoxy-4-methyl-pyridin-3-yl)-1-pyridin-4-yl-propan-1-one (30 mg) by treatment with a solution of tetrabutylammonium fluoride trihydrate (0.1M in THF, 0.23 ml) and trifluoromethyltrimethylsilane (2 M in THF, 0.13 ml). Purification by preparative HPLC (Phenomenex Gemini Axia- C18 column, solvent gradient 20-95% CH$_3$CN in 0.1% HCOOH[aq]) gave the title compound (9.6 mg). MS (m/e)=327.1 [M+H$^+$].

Example 158

1,1,1-Trifluoro-2-pyridin-4-yl-3-quinolin-3-yl-butan-2-ol

The title compound (14.5 mg) was prepared in analogy to Example 157, steps 1 to 2, from 3-bromoquinoline (CAS Reg. No. 5332-24-1), and 4-propionylpyridine (CAS Reg. No. 1701-69-5). MS (m/e)=333.1 [M+H$^+$].

Example 159

3-(3,4-Dichloro-phenyl)-1,1,1-trifluoro-2-pyridin-4-yl-butan-2-ol

The title compound (7.8 mg) was prepared in analogy to Example 157, steps 1 to 2, from 1-bromo-3,4-dichlorobenzene (CAS Reg. No. 18282-59-2), and 4-propionylpyridine (CAS Reg. No. 1701-69-5). MS (m/e)=350.1 [M+H$^+$].

Example 160

1,1,1-Trifluoro-3-(4-methoxy-phenyl)-2-pyridin-4-yl-butan-2-ol

The title compound (43.4 mg) was prepared in analogy to Example 157, steps 1 to 2, from 4-bromoanisole (CAS Reg. No. 104-92-7), and 4-propionylpyridine (CAS Reg. No. 1701-69-5). MS (m/e)=312.1 [M+H$^+$].

Example 161

1,1,1-Trifluoro-3-(4-methoxy-2-methyl-phenyl)-2-pyridin-4-yl-butan-2-ol

The title compound (21.8 mg) was prepared in analogy to Example 157, steps 1 to 2, from 2-bromo-5-methoxytoluene (CAS Reg. No. 27060-75-9), and 4-propionylpyridine (CAS Reg. No. 1701-69-5). MS (m/e)=326.1 [M+H$^+$].

Example 162

3-(2,4-Difluoro-phenyl)-1,1,1-trifluoro-2-pyridin-4-yl-butan-2-ol

The title compound (5.7 mg) was prepared in analogy to Example 157, steps 1 to 2, from 1-bromo-2,4-difluorobenzene (CAS Reg. No. 348-57-2), and 4-propionylpyridine (CAS Reg. No. 1701-69-5). MS (m/e)=318.1 [M+H$^+$].

Example 163

1,1,1-Trifluoro-3-(2-methoxy-naphthalen-1-yl)-2-pyridin-4-yl-butan-2-ol

The title compound (6.0 mg) was prepared in analogy to Example 157, steps 1 to 2, from 1-bromo-2-methoxynaphthalene (CAS Reg. No. 3401-47-6), and 4-propionylpyridine (CAS Reg. No. 1701-69-5). MS (m/e)=362.2 [M+H$^+$].

Example 164

1,1,1-Trifluoro-3-naphthalen-2-yl-2-pyridin-4-yl-butan-2-ol

The title compound (5.3 mg) was prepared in analogy to Example 157, steps 1 to 2, from 2-bromonaphthalene (CAS Reg. No. 580-13-2), and 4-propionylpyridine (CAS Reg. No. 1701-69-5). MS (m/e)=332.2 [M+H$^+$].

Example 165

3-(2-Chloro-4-diallylamino-phenyl)-2-(2-chloro-pyridin-4-yl)-1,1,1-trifluoro-butan-2-ol Step 1: 1-(4-Amino-2-chloro-phenyl)-ethanone Iron (2.7 g), ammonium chloride (2.6 g) and water (8.1 ml) were added to a solution of 1-(2-chloro-4-nitro-phenyl)-ethanone ([CAS Reg. No. 67818-41-1], 960 mg) in ethanol (68 ml), which was made from 2-chloro-4-nitro-benzoyl chloride and malonic acid dimethyl ester according to a procedure from Dai et al.; *J. Med. Chem.* 2005, 48, 6066. The mixture was heated 1 h under reflux. DCM (35 ml) was added, stirred for 2 min and filtered over Celite. The residue was washed with DCM (50 ml). Water (100 ml) was added to the combined organic layers, and then extracted with DCM. The combined organic layers were dried over Na$_2$SO$_4$ and concentrated in vacuo to give the title compound (837 mg) as light yellow oil, which was used in the next step without further purification. MS (m/e)=170.1 [M+H$^+$].

Step 2: 1-(2-Chloro-4-diallylamino-phenyl)-ethanone

A mixture of allyl bromide (1.5 ml), potassium carbonate (1.5 g) and 1-(4-amino-2-chloro-phenyl)-ethanone in DMF (4 ml) was heated at 90° C. for 15 h. Water (50 ml) was added, and then extracted with ethyl acetate. The combined organic layers were dried over Na$_2$SO$_4$ and concentrated in vacuo. The residue was purified by flash chromatography (silica gel, ethyl acetate/heptane 0:100-30:70) to give the title compound as a light yellow oil (400 mg). MS (m/e)=250.2 [M+H$^+$].

Step 3: 2-(2-Chloro-4-diallylamino-phenyl)-propionaldehyde

Potassium tert-butylate (1.33 g) was added to a solution of 1-(2-chloro-4-diallylamino-phenyl)-ethanone (2.36 g) and (methoxymethyl)triphenylphosphonium chloride ([CAS Reg. No. 4009-98-7], 3.75 g) in THF (55 ml). The mixture was stirred for 1 h at room temperature. Additional (methoxymethyl)triphenylphosphonium chloride (324 mg) and potassium tert-butylate (133 mg) were added and stirring was continued for 1 h. More (methoxymethyl)triphenylphosphonium chloride (324 mg) and potassium tert-butylate (133 mg) was added and stirring was continued for 30 min. HCl (25% aq, 15 ml) was added. The mixture was stirred for 1 h at room temperature and then for 45 min at 50° C. Water (100 ml) was added, neutralized carefully by addition of sodium bicarbonate, and then extracted with DCM. The combined organic layers were dried over Na$_2$SO$_4$ and concentrated in vacuo. The residue was purified by flash chromatography (silica gel, ethyl acetate/heptane 0:100-20:80) to give the title compound as a light yellow oil (2.1 g). MS (m/e)=264.1 [M+H⁺].

Step 4: 3-(2-Chloro-4-diallylamino-phenyl)-2-(2-chloro-pyridin-4-yl)-1,1,1-trifluoro-butan-2-ol The title compound (100 mg) was prepared in analogy to Example 115, steps 4 to 6, from 2-(2-chloro-4-diallylamino-phenyl)-propionaldehyde, and 2-chloro-4-iodopyridine (CAS Reg. No. 153034-86-7). Light yellow oil. MS (m/e)=445.2 [M+H⁺].

Example 166

N-{3-Chloro-4-[2-(2-chloro-pyridin-4-yl)-3,3,3-trifluoro-2-hydroxy-1-methyl-propyl]-phenyl}-methanesulfonamide Step 1: 3-(4-Amino-2-chloro-phenyl)-2-(2-chloro-pyridin-4-yl)-1,1,1-trifluoro-butan-2-ol A solution of 1,3-dimethylbarbituric acid ([CAS Reg. No. 769-42-6], 828 mg), tetrakis(triphenylphosphine) palladium (0) (230 mg) and 3-(2-Chloro-4-diallylamino-phenyl)-2-(2-chloro-pyridin-4-yl)-1,1,1-trifluoro-butan-2-ol (590 mg) in DCM (120 ml) was heated under reflux for 3 h. NaOH (1N aq) was added and extracted with DCM. The combined organic layers were dried over $Na_2SO_4$ and concentrated in vacuo. The residue was purified by flash chromatography (silica gel, ethyl acetate/heptane 0:100-50:50) to give the title compound as a light yellow gum (370 mg). MS (m/e)=365.0 [M+H⁺].

Step 2: N-{3-Chloro-4-[2-(2-chloro-pyridin-4-yl)-3,3,3-trifluoro-2-hydroxy-1-methyl-propyl]-phenyl}-methanesulfonamide Methanesulfonyl chloride (60 mg) was added to a solution of 3-(4-amino-2-chloro-phenyl)-2-(2-chloro-pyridin-4-yl)-1,1,1-trifluoro-butan-2-ol (38 mg) in pyridine (1 ml). The mixture was stirred for 30 min at room temperature. Purification by preparative HPLC (Phenomenex Gemini Axia-C18 column, solvent gradient 20-95% $CH_3CN$ in 0.1% HCOOH [aq]) gave the title compound (41 mg) as a white foam. MS (m/e)=443.1 [M+H+].

Example 167

N-{3-Chloro-4-[2-(2-chloro-pyridin-4-yl)-3,3,3-trifluoro-2-hydroxy-1-methyl-propyl]-phenyl}-benzamide N,N-diisopropylethylamine (0.117 ml) and benzoyl chloride (0.024 ml) were added to a solution of 3-(4-amino-2-chloro-phenyl)-2-(2-chloro-pyridin-4-yl)-1,1,1-trifluoro-butan-2-ol (25 mg) in DCM (3 ml). The mixture was stirred at room temperature for 2 h and then concentrated in vacuo. Purification by preparative HPLC (Phenomenex Gemini Axia-C18 column, solvent gradient 30-95% $CH_3CN$ in 0.1% HCOOH[aq]) gave the title compound (35 mg) as a white foam. MS (m/e)=469.2 [M+H⁺].

Example 168

3-(2-Chloro-4-fluoro-phenyl)-2-(6-chloro-pyridin-3-yl)-1,1,1-trifluoro-butan-2-ol The title compound (5 mg) was prepared in analogy to Example 165, steps 3 to 4, from 2-chloro-4-fluoroacetophenone (CAS Reg. No. 700-35-6), and 2-chloro-5-iodopyridine (CAS Reg. No. 69045-79-0). White solid. MS (m/e)=368.0 [M+H⁺].

Example 169

5-[2-(2-Chloro-4-fluoro-phenyl)-1-hydroxy-1-trifluoromethyl-propyl]-pyridine-2-carboxylic acid A solution of 3-(2-chloro-4-fluoro-phenyl)-2-(6-chloro-pyridin-3-yl)-1,1,1-trifluoro-butan-2-ol (100 mg), triethyl amine (0.4 ml), palladium (II) acetate (22 mg) and 1,3-bis(diphenylphosphino)propane (41 mg) in MeOH (10 ml) was heated under reflux under a carbon monoxide atmosphere for 20 h. The mixture was adsorbed on Isolute HM-N and purified by flash column chromatography (silica gel, ethyl acetate/heptane 20:80-50:50). Fractions containing the intermediate ester (not pure according to LCMS) were combined and concentrated. The residue was dissolved in aqueous lithium hydroxide solution (1N, 5 ml), THF (5 ml), MeOH (2.5 ml) and stirred for 5 min. LCMS indicated complete hydrolysis. Volatile organic solvents were evaporated and the aqueous residue was diluted with water (10 ml) and washed with ethyl acetate. The aqueous layer was acidified with HCl (aq, 1N) to pH 4 and extracted with ethyl acetate. The combined organic layers were dried over $Na_2SO_4$ and concentrated in vacuo to give the title compound in low yield (3 mg) as a colorless solid. MS (m/e, ISP neg. ion)=376.4 [M–H⁺].

Example 170

4-[2-(2-Chloro-4-fluoro-phenyl)-1-hydroxy-1-trifluoromethyl-propyl]-pyridine-2-carboxylic acid Step 1: 4-[2-(2-Chloro-4-fluoro-phenyl)-1-hydroxy-1-trifluoromethyl-propyl]-pyridine-2-carboxylic acid methyl ester A solution of 3-(2-chloro-4-fluoro-phenyl)-2-(2-chloro-pyridin-4-yl)-1,1,1-trifluoro-butan-2-ol (128 mg), 1,3-bis(diphenylphosphino)propane (41 mg), palladium (II) acetate (22 mg), and triethyl amine (0.145 ml) in methanol (10 ml) was stirred under reflux under a carbon monoxide atmosphere for 20 h. The mixture was adsorbed on Isolute HM-N and purified by flash column chromatography (silica gel, ethyl acetate/heptane 0:100-100:0). The title compound (24 mg) was obtained as a colorless oil. MS (m/e)=392.0 [M+H⁺].

Step 2: 4-[2-(2-Chloro-4-fluoro-phenyl)-1-hydroxy-1-trifluoromethyl-propyl]-pyridine-2-carboxylic acid 4-[2-(2-Chloro-4-fluoro-phenyl)-1-hydroxy-1-trifluoromethyl-propyl]-pyridine-2-carboxylic acid methyl ester (24 mg) was dissolved in an aqueous lithium hydroxide solution (1N, 5 ml), THF (5 ml), and methanol (2.5 ml). The mixture was stirred for 10 min. LCMS indicated complete hydrolysis. Volatile solvents were evaporated. The residue was diluted with water (10 ml) and washed with diethyl ether. The aqueous layer was acidified to about pH 4 with HCl (aq., 1N) and extracted with ethyl acetate. The combined organic layers were dried over $Na_2SO_4$ and concentrated in vacuo to give the title compound (22 mg) as a white solid. MS (m/e)=378.2 [M+H⁺].

Example 171

3-(4-Bromo-2-chloro-phenyl)-1,1,1-trifluoro-2-(2-methyl-pyridin-4-yl)-butan-2-ol The title compound (120 mg) was prepared in analogy to Example 165, steps 3 to 4, from 1-(4-bromo-2-chloro-phenyl)-ethanone (CAS Reg. No. 252561-81-2), and 4-bromo-2-methylpyridine (CAS Reg. No. 22282-99-1), which was lithiated with n-butyl lithium (1.6 M in hexanes) at −78° C. instead of the halogen magnesium exchange described in Example 115 step 4. White solid. MS (m/e)=410.0 [M+H$^+$].

Example 172

1-[1-(4-Chloro-phenyl)-cyclopropyl]-2,2,2-trifluoro-1-quinolin-3-yl-ethanol

Step 1: [1-(4-Chloro-phenyl)-cyclopropyl]-quinolin-3-yl-methanone

A solution of n-butyl lithium (1.6 M in hexanes, 1.5 ml) was added to 3-bromoquinoline (CAS Reg. No. 5332-24-1) (500 mg) in diethyl ether (16 ml) at −78° C. The mixture was stirred at −78° C. for 1 h. A solution of 1-(4-chlorophenyl)-1-cyclopropanecarbonitrile (CAS Reg. No. 64399-27-5) (427 mg) in 3 ml diethyl ether was added at −78° C. to the red mixture and then stirred for 15 min at −78° C. The mixture was allowed to warm to room temperature, then poured into water (40 ml) and extracted with diethyl ether. The combined organic layers were dried over Na$_2$SO$_4$ and concentrated in vacuo. The residue was purified by flash chromatography (silica gel, ethyl acetate/heptane 0:100-20:80, then ethyl acetate/DCM 0:100-10:90) to give the title compound as a light yellow oil (100 mg). MS (m/e)=308.3 [M+H$^+$].

Step 2: 1-[1-(4-Chloro-phenyl)-cyclopropyl]-2,2,2-trifluoro-1-quinolin-3-yl-ethanol The title compound (84 mg) was obtained in analogy to Example 1, step 5 from [1-(4-chloro-phenyl)-cyclopropyl]-quinolin-3-yl-methanone. Light yellow solid. MS (m/e)=378.1 [M+H$^+$].

Example 173

1-[1-(2,4-Dichloro-phenyl)-cyclopropyl]-2,2,2-trifluoro-1-quinolin-3-yl-ethanol

Step 1: 1-(2,4-Dichloro-phenyl)-cyclopropanecarbaldehyde

The title compound (900 mg) was obtained in analogy to Example 115, step 3 by reduction of 1-(2,4-dichlorophenyl)-1-cyclopropyl cyanide (CAS Reg. No. 71463-55-3) with diisobutylaluminium hydride. Colorless oil. MS (m/e)=214.0 [M$^+$].

Step 2: 1-[1-(2,4-Dichloro-phenyl)-cyclopropyl]-2,2,2-trifluoro-1-quinolin-3-yl-ethanol The title compound (73 mg) was obtained in analogy to Example 115, steps 4 to 6 from 1-(2,4-dichloro-phenyl)-cyclopropanecarbaldehyde and 3-bromoquinoline (CAS Reg. No. 5332-24-1), which was lithiated with n-butyl lithium (1.6 M in hexanes) at −78° C. instead of the halogen magnesium exchange described in Example 115, step 4. White solid. MS (m/e)=412.1 [M+H$^+$].

Example 174

1-(2-Chloro-pyridin-4-yl)-1-[1-(2,4-dichloro-phenyl)-cyclopropyl]-2,2,2-trifluoro-ethanol The title compound (224 mg) was obtained in analogy to Example 115, steps 4 to 6 from 1-(2,4-dichloro-phenyl)-cyclopropanecarbaldehyde and 2-chloro-4-iodopyridine (CAS Reg. No. 153034-86-7). White solid. MS (m/e)=396.0 [M+H$^+$].

Example 175

2-(2-Chloro-pyridin-4-yl)-3-(2,4-dichloro-phenyl)-1,1,1-trifluoro-3-methyl-butan-2-ol Step 1: 2-(2,4-Dichloro-phenyl)-2-methyl-propionitrile A solution of lithium diisopropylamide (2M in THF/heptane/ethylbenzene, 32.2 ml) was added to THF (60 ml) and cooled to −20° C. A solution of 2,4-dichlorobenzyl cyanide (10 g) in THF (10 ml) was added within 20 min. The mixture was stirred at −20° C. for 20 min, and then a solution of methyl iodide (4 ml) in THF (4 ml) was added. The mixture was stirred for 5 min. A solution of lithium diisopropylamide (2M in THF/heptane/ethylbenzene, 32.2 ml) was added within 20 min. The mixture was stirred for 30 min at −20° C., and then a solution of methyl iodide (4 ml) in THF (4 ml) was added within 5 min. The mixture was stirred for 1 h at room temperature. The mixture was poured to water (100 ml) and extracted with ethyl acetate. The combined organic layers were dried over Na$_2$SO$_4$ and concentrated in vacuo. The residue was purified by flash chromatography (silica gel, DCM/heptane 0:100-30:70) to give the title compound as a white solid (9.2 g). MS (m/e)=213 [M$^+$].

Step 2: 2-(2-Chloro-pyridin-4-yl)-3-(2,4-dichloro-phenyl)-1,1,1-trifluoro-3-methyl-butan-2-ol The title compound (80 mg) was obtained in analogy to Example 115, steps 3 to 6 from 2-(2,4-dichloro-phenyl)-2-methyl-propionitrile and 2-chloro-4-iodopyridine (CAS Reg. No. 153034-86-7). Colorless oil. MS (m/e)=400.0 [M+H$^+$].

Example 176

3-(4-Chloro-phenyl)-1,1,1-trifluoro-3-methyl-2-(2-methyl-pyridin-4-yl)-butan-2-ol The title compound (220 mg) was obtained in analogy to Example 175 from 4-chlorobenzyl cyanide (CAS Reg. No. 140-53-4) and 4-bromo-2-methylpyridine (CAS Reg. No. 22282-99-1) which was lithiated with n-butyl lithium (1.6 M in hexanes) at −78° C. instead of the halogen magnesium exchange used in Example 175. White foam. MS (m/e, ISP neg. ion)=342.2 [M−H$^+$].

Example 177

3-(2,6-Dichloro-pyridin-3-yl)-1,1,1-trifluoro-2-(5-methyl-pyrazin-2-yl)-butan-2-ol Step 1: (2,6-Dichloro-pyridin-3-yl)-acetic acid methyl ester HCl gas was bubbled through a solution of known 2,6-dichloropyridine-3-acetonitrile (CAS Reg. No. 58596-63-7)

(2.46 g) in MeOH (25 ml) until saturation was reached. The mixture was stirred at room temperature for 17 h. The solution was concentrated in vacuo. The residue was suspended in water, alkalized with aqueous sodium bicarbonate, and then extracted with DCM. The combined organic layers were dried over Na$_2$SO$_4$ and concentrated to the title compound (2.67 g). White solid. MS (m/e)=220.0 [M+H$^+$].

Step 2: 3-(2,6-Dichloro-pyridin-3-yl)-1,1,1-trifluoro-2-(5-methyl-pyrazin-2-yl)-butan-2-ol The title compound (20 mg) was obtained in analogy to Example 1, steps 2 to 5 from (2,6-dichloro-pyridin-3-yl)-acetic acid methyl ester and 5-methylpyrazine-2-carboxylic acid (CAS Reg. No. 5521-55-1). Light yellow oil. MS (m/e)=366.1 [M+H$^+$].

Example 178

3-(2-Chloro-4-methoxy-phenyl)-1,1,1-trifluoro-2-quinolin-3-yl-butan-2-ol

The title compound was prepared in analogy to Example 1, steps 2 to 5, from (2-chloro-4-methoxy-phenyl)-acetic acid methyl ester and quinoline-3-carboxylic acid. Light yellow solid. MS (m/e)=396.0 [M+H$^+$].

Example 179

3-Chloro-4-(3,3,3-trifluoro-2-hydroxy-1-methyl-2-quinolin-3-yl-propyl)-phenol 3-(2-Chloro-4-methoxy-phenyl)-1,1,1-trifluoro-2-quinolin-3-yl-butan-2-ol (Example 178, 2.60 g) was suspended in aqueous HBr (48%, 52 ml). The mixture was stirred for 16 h at 80° C., for 20 h at 105° C., for 7 h at 110° C. and for 6 h at 120° C. The reaction mixture was poured into ice water/EtOAc, neutralized with aqueous sat. Na$_2$CO$_3$ solution and extracted with EtOAc. The organic phase was washed with water and dried (MgSO$_4$). The product was purified by chromatography (SiO$_2$, cyclohexane=>cyclohexane/EtOAc 1:1=>EtOAc/MeOH 9:1=>1:1) and subsequently precipitated from hot EtOAc to give the title compound (1.83 g) as an off-white solid. MS (m/e)=382.1 [M+H$^+$].

Example 180

3-[2-Chloro-4-(4-methanesulfonyl-benzyloxy)-phenyl]-1,1,1-trifluoro-2-quinolin-3-yl-butan-2-ol To a suspension of 3-chloro-4-(3,3,3-trifluoro-2-hydroxy-1-methyl-2-quinolin-3-yl-propyl)-phenol (Example 179, 75 mg) in N,N-dimethylacetamide (1 ml) was added NaH (60% dispersion in mineral oil, 9 mg) at 0° C. The mixture was stirred at 0° C. for 1 h and at room temperature for 1 h. 4-Methylsulfonylbenzyl bromide (54 mg) was added and the mixture was stirred at room temperature for 3 h. Cesium carbonate (32 mg) was added and the mixture was stirred for 2 days at room temperature and for 5 h at 50° C. The reaction mixture was poured into water and extracted with EtOAc. The organic phase was washed with brine and dried (MgSO$_4$). The product was purified by chromatography (SiO$_2$, cyclohexane=>cyclohexane/EtOAc 1:1) to give the title compound (69 mg) as a light yellow solid. MS (m/e)=550.3 [M+H$^+$].

Example 181

Benzenesulfonic acid 3-chloro-4-(3,3,3-trifluoro-2-hydroxy-1-methyl-2-quinolin-3-yl-propyl)-phenyl ester To a suspension of 3-chloro-4-(3,3,3-trifluoro-2-hydroxy-1-methyl-2-quinolin-3-yl-propyl)-phenol (Example 179, 55 mg) and cesium carbonate (52 mg) in N,N-dimethylacetamide (1 ml) was added benzenesulfonyl chloride (25 mg). After being stirred at room temperature for 2 days, more benzenesulfonyl chloride (14 mg) was added and the mixture was stirred at room temperature for 2 h. Water was added and the mixture was extracted with EtOAc. The organic phase was washed with brine and with water and dried (MgSO$_4$). The product was purified by chromatography (SiO$_2$, cyclohexane=>cyclohexane/EtOAc 1:1) to give the title compound (29 mg) as an off-white solid. MS (m/e)=522.2 [M+H$^+$].

Example 182

3-(2-Chloro-4-methoxy-phenyl)-1,1,1-trifluoro-2-isoquinolin-5-yl-butan-2-ol

The title compound was prepared in analogy to Example 1, steps 2 to 5, from (2-chloro-4-methoxy-phenyl)-acetic acid methyl ester and isoquinoline-5-carboxylic acid. Brown oil. MS (m/e, ISP neg. ion)=396.1 [M+H$^+$].

Example 183

3-Chloro-4-(3,3,3-trifluoro-2-hydroxy-2-isoquinolin-5-yl-1-methyl-propyl)-phenol A solution of 3-(2-chloro-4-methoxy-phenyl)-1,1,1-trifluoro-2-isoquinolin-5-yl-butan-2-ol (Example 182, 50 mg) in dichloromethane (1.3 ml) was cooled to −70° C. A 1M solution of boron tribromide in dichloromethane (0.505 ml) was added and the mixture was stirred at −70° C. for 30 min and at 0° C. for 1 h. A mixture of ice water and saturated aqueous NaHCO$_3$ solution was added and the mixture was extracted with dichloromethane. The organic phase was washed with water, dried (MgSO$_4$), filtered and concentrated. The product was purified by chromatography (SiO$_2$, cyclohexane/EtOAc 1:0=>0:1) to give the title compound (45 mg) as a colorless solid. MS (m/e)=382.1 [M+H$^+$].

Example 184

3-[2-(2-Chloro-4-methoxy-phenyl)-1-hydroxy-1-trifluoromethyl-propyl]-quinoline-6-carbonitrile Step 1: 6-Cyano-quinoline-3-carboxylic acid ethyl ester To a suspension of 4-chloro-6-cyanoquinoline-3-carboxylic acid ethyl ester [CAS Reg. No 403841-76-9] (5 g) in ethanol (30 ml) were added triethylamine (3.90 g) and Pd (5% on charcoal, 200 mg). The mixture was stirred under a hydrogen atmosphere for 3.5 h using a balloon. The catalyst was filtered off and the filtrate was concentrated. Since the reaction was not finished, the hydrogenation was repeated using the same conditions. The product was purified by chromatography (SiO$_2$, cyclohexane/EtOAc 1:0=>0:1) to give the title compound (2.1 g) as a colorless solid. MS (m/e)=227.2 [M+H$^+$].

Step 2: 6-Cyano-quinoline-3-carboxylic acid

To a solution of 6-cyano-quinoline-3-carboxylic acid ethyl ester (1.28 g) in tetrahydrofuran (6 ml) and ethanol (6 ml) was added a 1M aqueous LiOH solution (6.79 ml) at 0° C. The mixture was stirred at 0° C. for 1.5 h, then the mixture was acidified with 1M aqueous HCl. The precipitate was filtered off, washed with water and a small amount of ether and dried to give the crude title compound (1.2 g) as an off-white solid that was used in the next step without further purification. MS (m/e, ISP neg. ion)=197.2 [M−H$^+$].

Steps 3 to 6: 3-[2-(2-Chloro-4-methoxy-phenyl)-1-hydroxy-1-trifluoromethyl-propyl]-quinoline-6-carbonitrile The title compound was prepared in analogy to Example 1, steps 2 to 5, from (2-chloro-4-methoxy-phenyl)-acetic acid methyl ester and 6-cyano-quinoline-3-carboxylic acid. Off-white solid. MS (m/e)=421.0 [M+H$^+$].

Example 185

3-(2,4-Dichloro-phenyl)-1,1,1-trifluoro-2-(5-fluoro-1H-indol-3-yl)-butan-2-ol

Step 1: 2-(2,4-Dichloro-phenyl)-1-(5-fluoro-1H-indol-3-yl)-propan-1-one

To a solution of 2-(2,4-dichloro-phenyl)-propionic acid (CAS Reg. No [25173-21-1], 300 mg) in tetrahydrofuran (5 ml) were added one drop of N,N-dimethylformamide and oxalylchloride (278 mg). The mixture was stirred at room temperature for 1.5 h. The solvent was evaporated and the crude acid chloride was dried. AlCl$_3$ (237 mg) was suspended in 1,2-dichloroethane (2 ml) and cooled in an ice bath. A solution of the acid chloride in 1,2-dichloroethane (3 ml) was added at 0° C. and stirred for 10 min. 5-Fluoroindol (185 mg) was added. The mixture was stirred for 30 min at 0° C. and for 1 h at room temperature. Ice and dichloromethane were added. The pH was adjusted to 8 with saturated aqueous NaHCO$_3$ solution. The organic phase was washed with water, dried (MgSO$_4$), filtered and concentrated to dryness. The product was purified by chromatography (SiO$_2$, cyclohexane/EtOAc 4:1=>1:1) to give the title compound (127 mg) as a colorless solid. MS (m/e, ISP neg. ion)=334.5 [M−H$^+$].

Step 2: 3-[2-(2,4-Dichloro-phenyl)-propionyl]-5-fluoro-indole-1-carboxylic acid tert-butyl ester To a suspension of 2-(2,4-dichloro-phenyl)-1-(5-fluoro-1H-indol-3-yl)-propan-1-one (61 mg) in dioxane (0.3 ml) and dichloromethane (0.3 ml) were added NaH (55 dispersion in mineral oil, 9 mg) and di-tert-butyl dicarbonate (48 mg) at 0° C. After being stirred at 0° C. for 20 min and at room temperature for 1 h, the reaction mixture was washed with water and brine, dried (MgSO$_4$), filtered and concentrated. Evaporation of the solvent under reduced pressure afforded 81 mg of the crude title compound as a light yellow solid. MS (m/e, ISP neg. ion)=494.2 [M+OAc$^-$].

Step 3: 3-(2,4-Dichloro-phenyl)-1,1,1-trifluoro-2-(5-fluoro-1H-indol-3-yl)-butan-2-ol To a solution of crude 3-[2-(2,4-dichloro-phenyl)-propionyl]-5-fluoro-indole-1-carboxylic acid tert-butyl ester (81 mg) in tetrahydrofuran (0.8 ml) (trifluoromethyl)-trimethyl-silane (2M in tetrahydrofuran, 0.23 ml) and tetrabutylammonium difluorotriphenylsilicate (20 mg) were added at 0° C. After being stirred at rt for 3 h, trifluoroacetic acid (127 mg) was added at 0° C. and stirred overnight. No deprotection was observed, so the mixture was neutralized with aq. 2M Na$_2$CO$_3$ solution and extracted with EtOAc. The combined organic layers were washed with water and dried over MgSO$_4$. After evaporation of the solvent, the residue was dissolved in CH$_2$Cl$_2$ (0.8 mL) and trifluoroacetic acid was added at 0° C. After being stirred for 1 h at 0° C. and at room temperature for 8 h, the reaction mixture was poured into ice water, neutralized with aq. 2M Na$_2$CO$_3$ solution and extracted with CH$_2$Cl$_2$. The organic phase was washed with water and aq. sat. NaCl solution, and dried over MgSO$_4$. MS: silylated product still present, the crude product was dissolved in 0.5 mL tetrahydrofuran and a solution of tetrabutylammonium fluoride (1M in tetrahydrofuran) was added at 0° C. After being stirred at room temperature for 1.5 h, the reaction mixture was poured into water, and extracted with EtOAc. The combined organic layers were washed with water and aq. sat. NaCl, and dried over MgSO$_4$. The product was purified by preparative TLC (cyclohexane/EtOAc 2:1) to give 17.9 mg of the title product as colorless oil. MS (m/e, ISP neg. ion)=404.4 [M−H$^+$].

Example 186

3-(2,4-Dichloro-phenyl)-1,1,1-trifluoro-2-(1-phenyl-1H-indazol-5-yl)-butan-2-ol

Step 1: 2-(2,4-Dichloro-phenyl)-1-(1-phenyl-1H-indazol-5-yl)-propan-1-ol

To a solution of 5-bromo-1-phenyl-1H-indazole (CAS Reg. No [861905-18-2], 592 mg) in tetrahydrofuran (20 ml) was added n-butyllithium (1.6 M in hexanes, 1.35 ml) at −78° C. The mixture was stirred at −78° C. for 15 min, then a solution of 2-(2,4-dichloro-phenyl)-propionalde (CAS Reg. No [858208-19-2], 400 mg) in tetrahydrofuran (10 ml) was added. The mixture was stirred at −78° C. for 30 min and at 0° C. for 1 h. A mixture of ice water and saturated aqueous NH$_4$Cl solution was added and the mixture was extracted with EtOAc. The organic phase was washed with brine, dried (MgSO$_4$), filtered and concentrated to dryness. The product was purified by chromatography (SiO$_2$, cyclohexane/EtOAc 1:0=>0:1) to give the title compound (441 mg, not completely pure) as an off-white solid that was used in the next step without further purification. MS (m/e)=397.1 [M+H$^+$].

Step 2: 2-(2,4-Dichloro-phenyl)-1-(1-phenyl-1H-indazol-5-yl)-propan-1-one

To a solution of 2-(2,4-dichloro-phenyl)-1-(1-phenyl-1H-indazol-5-yl)-propan-1-ol (180 mg) in dichloromethane (5 ml) was added powdered molecular sieve 3A (1 g). Tetrapropylammonium perruthenate (16 mg) and 4-methylmorpholine-4-oxide (106 mg) were added. The mixture was stirred at room temperature for 1.5 h. The mixture was filtered and the filtrate was concentrated to dryness. The product was purified by chromatography (SiO$_2$, cyclohexane/EtOAc 1:0=>1:3) to give the title compound (149 mg) as an off-white solid. MS (m/e)=394.9 [M+H$^+$].

Step 3: 3-(2,4-Dichloro-phenyl)-1,1,1-trifluoro-2-(1-phenyl-1H-indazol-5-yl)-butan-2-ol In analogy to Example 1, step 5,2-(2,4-dichloro-phenyl)-1-(1-phenyl-1H-indazol-5-yl)-propan-1-one was converted to the title compound. Off-white solid. MS (m/e, ISP neg. ion)=463.0 [M+H$^+$].

Example 187

3-(2,4-Dichloro-phenyl)-1,1,1-trifluoro-2-[1-(3-methoxy-phenyl)-1H-indazol-5-yl]-butan-2-ol Step 1: 5-Bromo-1-(3-methoxy-phenyl)-1H-indazole 3-Methoxyphenylhydrazine hydrochloride (1 g) was suspended in 1M aqueous NaOH solution and extracted with ether. The organic phase was dried (MgSO$_4$), filtered and concentrated to dryness to give 3-methoxyphenylhydrazine. 2,5-Dibromobenzaldehyde (1 g) and N-methylpyrrolidone (3.7 ml) were added and the mixture was heated under microwave conditions to 160° C. for 10 min. K$_2$CO$_3$ (1.015 g), CuI (36 mg) and trans-N,N'-dimethyl-cyclohexane-1,2-diamine (53 mg) were added and the mixture was heated under microwave conditions to 160° C. for 40 min. CuI (18 mg) and trans-N,N'-dimethyl-cyclohexane-1,2-diamine (26 mg) were added and the mixture was heated under microwave conditions to 160° C. for 20 min. The mixture was filtered and the filtrate was concentrated. The product was purified by chromatography (SiO$_2$, CH$_2$Cl$_2$/MeOH 100:0=>95:5) to give the title compound (659 mg) as a yellow oil. MS (m/e)=303.0 [M+H$^+$].

Steps 2-4: 3-(2,4-Dichloro-phenyl)-1,1,1-trifluoro-2-[1-(3-methoxy-phenyl)-1H-indazol-5-yl]-butan-2-ol In analogy to Example 186, 5-bromo-1-(3-methoxy-phenyl)-1H-indazole was reacted with 2-(2,4-dichloro-phenyl)-propionaldehyde to give 2-(2,4-dichloro-phenyl)-1-[1-(3-methoxy-phenyl)-1H-indazol-5-yl]-propan-1-ol which was oxidized to 2-(2,4-dichloro-phenyl)-1-[1-(3-methoxy-phenyl)-1H-indazol-5-yl]-propan-1-one and converted further to the title compound. Colorless solid. MS (m/e)=495.2 [M+H$^+$].

Example 188

3-{5-[2-(2,4-Dichloro-phenyl)-1-hydroxy-1-trifluoromethyl-propyl]-indazol-1-yl}-phenol In analogy to Example 183, 3-(2,4-dichloro-phenyl)-1,1,1-trifluoro-2-[1-(3-methoxy-phenyl)-1H-indazol-5-yl]-butan-2-ol (Example 187) was reacted with BBr$_3$ to give the title compound as a colorless foam. MS (m/e, ISP neg. ion)=479.0 [M−H$^+$].

Example 189

3-(2,4-Dichloro-phenyl)-1,1,1-trifluoro-2-[1-(2-methoxy-phenyl)-1H-indazol-5-yl]-butan-2-ol Step 1: 5-Bromo-1-(2-methoxy-phenyl)-1H-indazole In analogy to Example 187, step 1,2-methoxyphenylhydrazine was reacted with 2,5-dibromobenzaldehyde to give the title compound as a brown oil. MS (m/e)=303.2 [M+H$^+$].

Steps 2-4: 3-(2,4-Dichloro-phenyl)-1,1,1-trifluoro-2-[1-(2-methoxy-phenyl)-1H-indazol-5-yl]-butan-2-ol In analogy to Example 186, 5-bromo-1-(2-methoxy-phenyl)-1H-indazole was reacted with 2-(2,4-dichloro-phenyl)-propionaldehyde to give 2-(2,4-dichloro-phenyl)-1-[1-(2-methoxy-phenyl)-1H-indazol-5-yl]-propan-1-ol which was oxidized to 2-(2,4-dichloro-phenyl)-1-[1-(2-methoxy-phenyl)-1H-indazol-5-yl]-propan-1-one and converted further to the title compound. Colorless solid. MS (m/e)=495.1 [M+H$^+$].

Example 190

2-{5-[2-(2,4-Dichloro-phenyl)-1-hydroxy-1-trifluoromethyl-propyl]-indazol-1-yl}-phenol In analogy to Example 183, 3-(2,4-dichloro-phenyl)-1,1,1-trifluoro-2-[1-(2-methoxy-phenyl)-1H-indazol-5-yl]-butan-2-ol (Example 189) was reacted with BBr$_3$ to give the title compound as a colorless foam. MS (m/e, ISP neg. ion)=479.0 [M+H$^+$].

Example 191

3-(2,4-Dichloro-phenyl)-1,1,1-trifluoro-2-[1-(4-methoxy-phenyl)-1H-indazol-5-yl]-butan-2-ol Step 1: 5-Bromo-1-(4-methoxy-phenyl)-1H-indazole In analogy to Example 187, step 1,4-methoxyphenylhydrazine was reacted with 2,5-dibromobenzaldehyde to give the title compound as a light brown solid. MS (m/e)=303.0 [M+H$^+$].

Steps 2-4: 3-(2,4-Dichloro-phenyl)-1,1,1-trifluoro-2-[1-(4-methoxy-phenyl)-1H-indazol-5-yl]-butan-2-ol In analogy to Example 186, 5-bromo-1-(4-methoxy-phenyl)-1H-indazole was reacted with 2-(2,4-dichloro-phenyl)-propionaldehyde to give 2-(2,4-dichloro-phenyl)-1-[1-(4-methoxy-phenyl)-1H-indazol-5-yl]-propan-1-ol which was oxidized to 2-(2,4-dichloro-phenyl)-1-[1-(4-methoxy-phenyl)-1H-indazol-5-yl]-propan-1-one and converted further to the title compound. Off-white foam. MS (m/e)=495.1 [M+H$^+$].

Example 192

4-{5-[2-(2,4-Dichloro-phenyl)-1-hydroxy-1-trifluoromethyl-propyl]-indazol-1-yl}-phenol In analogy to Example 183, 3-(2,4-dichloro-phenyl)-1,1,1-trifluoro-2-[1-(4-methoxy-phenyl)-1H-indazol-5-yl]-butan-2-ol (Example 191) was reacted with BBr$_3$ to give the title compound as a colorless foam. MS (m/e)=481.0 [M+H$^+$].

Example 193

3-(2-Chloro-4-methoxy-phenyl)-1,1,1-trifluoro-2-(6-methoxy-pyridin-3-yl)-butan-2-ol The title compound was prepared in analogy to Example 1, steps 2 to 5, from (2-chloro-4-methoxy-phenyl)-acetic acid methyl ester and 6-methoxynicotinic acid. Light yellow solid. MS (m/e)=376.1 [M+H$^+$].

Example 194

5-[2-(2-Chloro-4-methoxy-phenyl)-1-hydroxy-1-trifluoromethyl-propyl]-1H-pyridin-2-one To a solution of 3-(2-chloro-4-methoxy-phenyl)-1,1,1-trifluoro-2-(6-methoxy-pyridin-3-yl)-butan-2-ol (Example 193, 212 mg) in dioxane (8.5 ml) was added concentrated aqueous HCl (0.934 ml). The mixture was stirred at 100° C. for 1 h. After cooling to room temperature, EtOAc and water were added and the mixture was extracted with EtOAc. The organic phase was dried (MgSO$_4$), filtered and concentrated to dryness to give the title compound (207 mg) as a colorless solid. MS (m/e, ISP neg. ion)=360.0 [M−H$^+$].

Example 195

5-[2-(2-Chloro-4-methoxy-phenyl)-1-hydroxy-1-trifluoromethyl-propyl]-1-methyl-1H-pyridin-2-one To a solution of 5-[2-(2-chloro-4-methoxy-phenyl)-1-hydroxy-1-trifluoromethyl-propyl]-1H-pyridin-2-one (Example 194, 100 mg) in N,N-dimethylacetamide (1.5 ml) were added powdered K$_2$CO$_3$ (42 mg) and iodomethane (41 mg). The mixture was stirred at room temperature for 3 days. EtOAc and water were added and the mixture was extracted with EtOAc. The organic phase was dried (MgSO$_4$), filtered and concentrated to dryness. The product was purified by chromatography (SiO$_2$, cyclohexane/EtOAc 1:1=>0:1) to give the title compound (113 mg, contains 10.7 mass-% of N,N-dimethylacetamide) as a light yellow oil. MS (m/e)=376.1 [M+H$^+$].

Example 196

5-[2-(2-Chloro-4-hydroxy-phenyl)-1-hydroxy-1-trifluoromethyl-propyl]-1-methyl-1H-pyridin-2-one In analogy to Example 183, 5-[2-(2-chloro-4-methoxy-phenyl)-1-hydroxy-1-trifluoromethyl-propyl]-1-methyl-1H-pyridin-2-one (Example 195) was reacted with BBr$_3$ to give the title compound as a colorless solid. MS (m/e, ISP neg. ion)=360.0 [M+H$^+$].

Example 197

4-{3-Chloro-4-[3,3,3-trifluoro-2-hydroxy-1-methyl-2-(1-methyl-6-oxo-1,6-dihydro-pyridin-3-yl)-propyl]-phenoxy}-3-fluoro-benzonitrile To a solution of 5-[2-(2-chloro-4-hydroxy-phenyl)-1-hydroxy-1-trifluoromethyl-propyl]-1-methyl-1H-pyridin-2-one (Example 196, 100 mg) in N,N-dimethylacetamide (2 ml) were added 3,4-difluorobenzonitrile (46 mg) and cesium carbonate (272 mg). The mixture was stirred for 18 h at room temperature. EtOAc and ice water were added and the mixture was extracted with EtOAc. The organic phase was washed with water, dried (MgSO$_4$), filtered and concentrated to dryness. The product was purified by chromatography (SiO$_2$, cyclohexane/EtOAc 95:5=>0:1) to give the title compound (133 mg) as a colorless solid. MS (m/e)=481.1 [M+H$^+$].

Example 198

3-Chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzonitrile In analogy to Example 197, 5-[2-(2-chloro-4-hydroxy-phenyl)-1-hydroxy-1-trifluoromethyl-propyl]-1-methyl-1H-pyridin-2-one (Example 196) was reacted with 3-chloro-4-fluorobenzonitrile and cesium carbonate to give the title compound as a colorless solid. MS (m/e)=497.3 [M+H$^+$].

Example 199

5-{2-[2-Chloro-4-(4-fluoro-3-methoxy-phenoxy)-phenyl]-1-hydroxy-1-trifluoromethyl-propyl}-1-methyl-1H-pyridin-2-one To a solution of 5-[2-(2-chloro-4-hydroxy-phenyl)-1-hydroxy-1-trifluoromethyl-propyl]-1-methyl-1H-pyridin-2-one (Example 196, 200 mg) in CH$_2$Cl$_2$ (4 ml) were added 4-fluoro-3-methoxyphenylboronic acid (282 mg), copper-(II)-acetate (307 mg), molecular sieve and pyridine (219 mg). The mixture was stirred at room temperature under an air atmosphere with exclusion of moisture for 7 days. The mixture was filtered, diluted with CH$_2$Cl$_2$ and washed with 1M aqueous HCl. The organic phase was dried (MgSO$_4$), filtered and concentrated to dryness. The product was purified by chromatography (SiO$_2$, cyclohexane/EtOAc 1:0=>0:1) to give the title compound (139 mg) as an off-white solid. MS (m/e)=486.3 [M+H$^+$].

Example 200

5-{2-[2-Chloro-4-(4-fluoro-3-hydroxy-phenoxy)-phenyl]-1-hydroxy-1-trifluoromethyl-propyl}-1-methyl-1H-pyridin-2-one In analogy to Example 183, 5-{2-[2-chloro-4-(4-fluoro-3-methoxy-phenoxy)-phenyl]-1-hydroxy-1-trifluoromethyl-propyl}-1-methyl-1H-pyridin-2-one (Example 199) was reacted with BBr$_3$ to give the title compound as an off-white solid. MS (m/e)=472.2 [M+H$^+$].

Example 201

5-[2-(2,4-Dichloro-phenyl)-1-hydroxy-1-trifluoromethyl-propyl]-1-methyl-1H-pyridin-2-one Step 1: 2-(2,4-Dichloro-phenyl)-3-(6-methoxy-pyridin-3-yl)-3-oxo-propionitrile To a suspension of potassium-tert-butylate (2.052 g) in tert-butanol (25 ml) was added methyl-6-methoxynicotinate (2.5 g). 2,4-Dichlorobenzyl cyanide (2.782 g) was added portion wise. The mixture was heated to 100° C. for 1.5 h. After cooling to room temperature, water (100 ml) was added and the mixture was washed with diethyl ether. The aqueous phase was neutralized with concentrated aqueous HCl and extracted with EtOAc. The organic phase was washed with water and with brine, dried (MgSO$_4$), filtered and concentrated to dryness to give the title compound (1.407 g) as a yellow foam that was used in the next step without further purification. MS (m/e)=321.0 [M+H$^+$].

Step 2: 5-[2-(2,4-Dichloro-phenyl)-acetyl]-1H-pyridin-2-one

To a solution of 2-(2,4-dichloro-phenyl)-3-(6-methoxy-pyridin-3-yl)-3-oxo-propionitrile (1.358 g) in 1,4-dioxane (6 ml) was added concentrated aqueous HCl (11.5 ml). The mixture was stirred for 21 h at 80° C. The solvent was evaporated and the residue was suspended in water (30 ml). The pH was adjusted to 7 using concentrated aqueous NaHCO$_3$ solution. The solid was filtered off, washed with water and dried to give the title compound as a colorless solid (0.84 g). MS (m/e, ISP neg. ion)=281.1 [M–H$^+$].

Step 3: 5-[2-(2,4-Dichloro-phenyl)-acryloyl]-1H-pyridin-2-one

To a solution of 5-[2-(2,4-dichloro-phenyl)-acetyl]-1H-pyridin-2-one (800 mg) in CH$_2$Cl$_2$ (2.8 ml) was added N,N,N'N'-tetramethyldiaminomethane (896 mg). The mixture was cooled to 0° C. and acetic acid anhydride (0.64 ml) was added. The mixture was stirred at 0° C. for 10 min and at room temperature for 4 h. The solvent was evaporated under reduced pressure. The residue was dissolved in EtOAc and washed with water. The organic phase was concentrated to dryness to give the title compound (857 mg) as a light brown solid that was used for the next step without further purification. MS (m/e, ISP neg. ion)=291.9 [M–H$^+$].

Step 4: 5-[2-(2,4-Dichloro-phenyl)-propionyl]-1H-pyridin-2-one

5-[2-(2,4-Dichloro-phenyl)-acryloyl]-1H-pyridin-2-one (840 mg) was hydrogenated in EtOAc using 5% Pd/Alox as a catalyst to give the title compound (233 mg) as a light brown solid. MS (m/e, ISP neg. ion)=293.8 [M–H$^+$].

Step 5: 5-[2-(2,4-Dichloro-phenyl)-propionyl]-1-methyl-1H-pyridin-2-one

In analogy to Example 195, 5-[2-(2,4-dichloro-phenyl)-propionyl]-1H-pyridin-2-one was alkylated with iodomethane to give the title compound as a colorless oil. MS (m/e)=310.1 [M+H$^+$].

Step 6: 5-[2-(2,4-Dichloro-phenyl)-1-hydroxy-1-trifluoromethyl-propyl]-1-methyl-1H-pyridin-2-one In analogy to Example 1, step 5, 5-[2-(2,4-dichloro-phenyl)-propionyl]-1-methyl-1H-pyridin-2-one was converted to the title compound. Colorless oil. MS (m/e)=380.2 [M+H$^+$].

Example 202

5-[2-(2,4-Dichloro-phenyl)-1-hydroxy-1-trifluoromethyl-propyl]-1-ethyl-1H-pyridin-2-one Step 1: 5-[2-(2,4-Dichloro-phenyl)-propionyl]-1-ethyl-1H-pyridin-2-one In analogy to Example 195, 5-[2-(2,4-dichloro-phenyl)-propionyl]-1H-pyridin-2-one (Example 201, step 4) was alkylated with iodoethane to give the title compound as a colorless oil. MS (m/e)=324.2 [M+H$^+$].

Step 2: 5-[2-(2,4-Dichloro-phenyl)-1-hydroxy-1-trifluoromethyl-propyl]-1-ethyl-1H-pyridin-2-one In analogy to Example 1, step 5, 5-[2-(2,4-Dichloro-phenyl)-propionyl]-1-ethyl-1H-pyridin-2-one was converted to the title compound. Off-white solid. MS (m/e)=394.0 [M+H$^+$].

Example 203

5-[2-(4-Bromo-2-chloro-phenyl)-1-hydroxy-1-trifluoromethyl-propyl]-1-methyl-1H-pyridin-2-one Step 1: 5-[2-(4-Bromo-2-chloro-phenyl)-acetyl]-1-methyl-1H-pyridin-2-one To a suspension of 1-methyl-6-oxo-1,6-dihydro-pyridine-3-carboxylic acid (606 mg) in CH$_2$Cl$_2$ (5 ml) were added one drop of N,N-dimethylformamide and oxalylchloride (803 mg). The mixture was stirred at room temperature for 1.5 h and was then concentrated to dryness. 1,2-Dimethoxyethane was added and the solvent was evaporated again to give the crude acid chloride. To a suspension of zinc powder (517 mg) in 1,2-dimethoxyethane (5 ml) was added tetrakis(triphenylphosphine)palladium(0) (55 mg). A suspension of the acid chloride in 1,2-dimethoxyethane (5 ml) was added. The mixture was cooled in an ice bath and a solution of 4-bromo-1-bromomethyl-2-chloro-benzene (1.125 g) in 1,2-dimethoxyethane (5 ml) was slowly added over 30 min. The mixture was stirred for 30 min at 0° C. and for 1.5 h at room temperature. The mixture was filtered and the filtrate was concentrated. The product was purified by chromatography (SiO$_2$, cyclohexane/EtOAc 7:3=>0:1) to give the title compound (603 mg, not completely pure) as a colorless solid. MS (m/e, ISP neg. ion)=338.0 [M–H$^+$].

Steps 2 to 3: 5-[2-(4-Bromo-2-chloro-phenyl)-1-hydroxy-1-trifluoromethyl-propyl]-1-methyl-1H-pyridin-2-one In analogy to Example 1, steps 4 and 5, 5-[2-(4-bromo-2-chloro-phenyl)-acetyl]-1-methyl-1H-pyridin-2-one was alkylated with iodomethane to give 5-[2-(4-bromo-2-chloro-phenyl)-propionyl]-1-methyl-1H-pyridin-2-one which was further converted to the title compound. Colorless foam. MS (m/e, ISP neg. ion)=421.8 [M–H$^+$].

Example 204

3-(4-Bromo-2-chloro-phenyl)-1,1,1-trifluoro-2-(6-methoxy-pyridin-3-yl)-butan-2-ol Step 1: 2-(4-Bromo-2-chloro-phenyl)-1-(6-methoxy-pyridin-3-yl)-ethanone In analogy to Example 203, step 1, 6-methoxynicotinic acid was converted to the acid chloride and subsequently reacted with 4-bromo-1-bromomethyl-2-chloro-benzene to give the title compound (not completely pure) as a light yellow solid.

Steps 2 to 3: 3-(4-Bromo-2-chloro-phenyl)-1,1,1-trifluoro-2-(6-methoxy-pyridin-3-yl)-butan-2-ol In analogy to Example 1, steps 4 and 5,2-(4-bromo-2-chloro-phenyl)-1-(6-methoxy-pyridin-3-yl)-ethanone was alkylated with iodomethane to give 2-(4-bromo-2-chloro-phenyl)-1-(6-methoxy-pyridin-3-yl)-propan-1-one which was further converted to the title compound. Colorless Oil. MS (m/e)=424.0 [M+H$^+$].

Example 205

5-[2-(4-Bromo-2-chloro-phenyl)-1-hydroxy-1-trifluoromethyl-propyl]-1H-pyridin-2-one In analogy to Example 194, 2-(4-bromo-2-chloro-phenyl)-1-(6-methoxy-pyridin-3-yl)-propan-1-one was converted to

Example 206

5-[2-(4-Bromo-2-chloro-phenyl)-1-hydroxy-1-trifluoromethyl-propyl]-1-ethyl-1H-pyridin-2-one In analogy to Example 195, 5-[2-(4-bromo-2-chloro-phenyl)-1-hydroxy-1-trifluoromethyl-propyl]-1H-pyridin-2-one (Example 205) was alkylated with iodoethane to give the title compound as a light yellow oil. MS (m/e)=438.2 [M+H$^+$].

Example 207

5-[2-(2-Chloro-5-methoxy-phenyl)-1-hydroxy-1-trifluoromethyl-propyl]-1-methyl-1H-pyridin-2-one The title compound was prepared in analogy to Example 1, steps 2 to 5, from (2-chloro-5-methoxy-phenyl)-acetic acid methyl ester and 1-methyl-6-oxo-1,6-dihydro-pyridine-3-carboxylic acid. Light grey foam. MS (m/e)=376.2 [M+H+].

Example 208

5-[2-(2,3-Dichloro-4-methoxy-phenyl)-1-hydroxy-1-trifluoromethyl-propyl]-1-methyl-1H-pyridin-2-one The title compound was prepared in analogy to Example 1, steps 2 to 5, from (2,3-dichloro-4-methoxyphenyl)acetic acid methyl ester and 1-methyl-6-oxo-1,6-dihydro-pyridine-3-carboxylic acid. Colorless solid. MS (m/e, ISP neg. ion.)=408.2 [M−H].

Example 209

5-[2-(2,3-Dichloro-4-hydroxy-phenyl)-1-hydroxy-1-trifluoromethyl-propyl]-1-methyl-1H-pyridin-2-one In analogy to Example 183, 5-[2-(2,3-dichloro-4-methoxy-phenyl)-1-hydroxy-1-trifluoromethyl-propyl]-1-methyl-1H-pyridin-2-one (Example 208) was reacted with BBr$_3$ to give the title compound as a light yellow foam. MS (m/e, ISP neg. ion)=393.8 [M−H$^+$].

Example 210

5-[2-(2-Chloro-5-fluoro-4-methoxy-phenyl)-1-hydroxy-1-trifluoromethyl-propyl]-1-methyl-1H-pyridin-2-one Step 1: 5-[2-(2-Chloro-5-fluoro-4-methoxy-phenyl)-propionyl]-1-methyl-1H-pyridin-2-one In analogy to Example 203, step 1, 1-methyl-6-oxo-1,6-dihydro-pyridine-3-carboxylic acid was converted to the acid chloride and subsequently reacted with 1-bromomethyl-2-chloro-5-fluoro-4-methoxy-benzene (CAS Reg. No. [853569-69-4]) to give the title compound.

Steps 2 to 3: 5-[2-(2-Chloro-5-fluoro-4-methoxy-phenyl)-1-hydroxy-1-trifluoromethyl-propyl]-1-methyl-1H-pyridin-2-one In analogy to Example 1, steps 4 and 5, 5-[2-(2-chloro-5-fluoro-4-methoxy-phenyl)-propionyl]-1-methyl-1H-pyridin-2-one was alkylated with iodomethane to give 5-[2-(2-chloro-5-fluoro-4-methoxy-phenyl)-propionyl]-1-methyl-1H-pyridin-2-one which was further converted to the title compound. Colorless solid. MS (m/e)=394.1 [M+H$^+$].

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:
1. A compound of formula I:

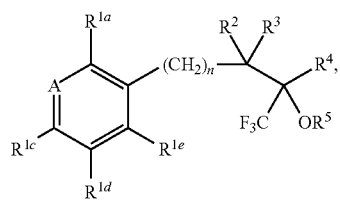

I wherein:
A is C—$R^{1b}$;
$R^{1a}$, $R^{1b}$, $R^{1c}$, $R^{1d}$ and $R^{1e}$ independently from each other are selected from the group consisting of hydrogen, $C_{1-7}$-alkyl, $C_{3-7}$-cycloalkyl-$C_{1-7}$-alkyl,
halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano,
carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy,
di-$C_{1-7}$-alkylamino, di-$C_{2-7}$-alkenylamino, $C_{1-7}$-alkylsulfonylamino,
phenylcarbonylamino, phenylsulfonyloxy,
heteroaryl-$C_{1-7}$-alkoxy, wherein the heteroaryl ring is selected from the group consisting of oxadiazolyl, isoxazolyl, thiadiazolyl and tetrazolyl and is unsubstituted or substituted by $C_{1-7}$-alkyl,
phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy; and not more than three of $R^{1a}$, $R^{1b}$, $R^{1c}$, $R^{1d}$ and $R^{1e}$ are hydrogen;
$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;
$R^3$ is hydrogen or $C_{1-7}$-alkyl;
or $R^2$ and $R^3$ together with the carbon atom to which they are attached form a $C_3$-$C_5$-cycloalkyl ring;
$R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrazolyl, imidazolyl, thiazolyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl,
said heteroaryl ring being unsubstituted or substituted by one, two or three substituents selected from the group consisting of
halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy,
$R^6R^7N$-carbonyl-$C_{1-7}$-alkoxy, wherein $R^6$ and $R^7$ are independently selected from hydrogen or $C_{1-7}$-alkyl or $R^6$ and $R^7$ together with the nitrogen atom to which they are attached form a heterocyclic ring selected from pyrrolidine, piperidine, morpholine or thiomorpholine,
phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy;
pyridyl,
heterocyclyl selected from the group consisting of pyrrolidine and piperidine, said heterocyclyl ring being unsubstituted or substituted by carboxyl or $C_{1-7}$-alkoxycarbonyl, phenyl-$C_{1-7}$-alkyl, phenyloxy and phenyl-$C_{1-7}$-alkoxy;
$R^5$ is hydrogen or methyl; and
n is 0 or 1;
or a pharmaceutically acceptable salts thereof.
2. The compound according to claim 1, wherein n is 0.
3. The compound according to claim 1, wherein $R^{1a}$, $R^{1b}$, $R^{1c}$, $R^{1d}$ and $R^{1e}$ are selected from the group consisting of hydrogen, halogen, halogen-$C_{1-7}$-alkyl, hydroxy, $C_{1-7}$-alkoxy, cyano, carboxyl, $C_{1-7}$-alkoxycarbonyl, di-$C_{2-7}$-alkenylamino,
heteroaryl-$C_{1-7}$-alkoxy, wherein the heteroaryl ring is selected from the group consisting of oxadiazolyl, isoxazolyl, thiadiazolyl and tetrazolyl and is unsubstituted or substituted by $C_{1-7}$-alkyl,
phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy.

4. The compound according to claim 1, wherein $R^{1a}$ is halogen.

5. The compound according to claim 1, wherein $R^{1a}$ is halogen and $R^{1c}$ is selected from the group consisting of halogen, $C_{1-7}$-alkoxy and phenyl-$C_{1-7}$-alkoxy.

6. The compound according to claim 1, wherein $R^2$ is $C_{1-7}$-alkyl.

7. The compound according to claim 1, wherein $R^3$ is hydrogen.

8. The compound according to claim 1, wherein $R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrazolyl, imidazolyl, thiazolyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, cyano, $C_{1-7}$-alkyl, $C_{1-7}$-alkoxy, cyano-$C_{1-7}$-alkoxy, carboxyl-$C_{1-7}$-alkoxy, $C_{1-7}$-alkoxycarbonyl, phenyl, pyridyl, pyrrolidinyl and phenyl-$C_{1-7}$-alkoxy.

9. The compound according to claim 1, wherein $R^4$ is a heteroaryl ring selected from the group consisting of pyridyl, pyrazinyl, pyrimidinyl, pyridazinyl and 2-oxo-1,2-dihydropyridinyl, said heteroaryl ring being unsubstituted or substituted by one, two or three substituents selected from the group consisting of
halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy,
$R^6R^7N$-carbonyl-$C_{1-7}$-alkoxy, wherein $R^6$ and $R^7$ are independently selected from hydrogen or $C_{1-7}$-alkyl or $R^6$ and $R^7$ together with the nitrogen atom they are attached to form a heterocyclic ring selected from pyrrolidine, piperidine, morpholine or thiomorpholine,
phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy,
pyridyl,
heterocyclyl selected from the group consisting of pyrrolidine and piperidine, said heterocyclyl ring being unsubstituted or substituted by carboxyl or $C_{1-7}$-alkoxycarbonyl, phenyl-$C_{1-7}$-alkyl, phenyloxy and phenyl-$C_{1-7}$-alkoxy.

10. The compound according to claim 1, wherein $R^5$ is hydrogen.

11. The compound according to claim 1 having the formula I-A:

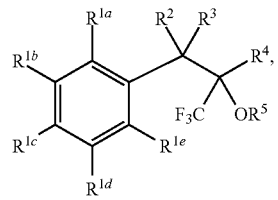

wherein
$R^{1a}$, $R^{1b}$, $R^{1c}$, $R^{1d}$ and $R^{1e}$ independently from each other are selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, hydroxy, $C_{1-7}$-alkoxy, carboxyl, carboxyl-$C_{1-7}$-alkyl, carboxyl-$C_{1-7}$-alkoxy,
phenyloxy and phenyl-$C_{1-7}$-alkoxy, said phenyl ring being unsubstituted or substituted by one, two or three substituents selected from the group consisting of halogen, halogen-$C_{1-7}$-alkyl, $C_{1-7}$-alkyl, $C_{1-7}$-alkoxy and halogen-$C_{1-7}$-alkoxy;
$R^2$ is selected from the group consisting of $C_{1-7}$-alkyl, $C_{3-7}$-cycloalkyl-$C_{1-7}$-alkyl and triazolyl-$C_{1-7}$-alkyl;
$R^3$ is hydrogen or $C_{1-7}$-alkyl;
$R^4$ is a heteroaryl ring selected from the group consisting of pyridyl, pyrazinyl, pyrimidinyl, pyridazinyl, quinolinyl, pyrazolyl, imidazolyl, thiazolyl,
pyrazolo[1,5-a]pyridyl, imidazo[1,2-a]pyridyl, quinoxalinyl, benzothiazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl,
$C_{1-7}$-alkyl, $C_{3-7}$-cycloalkyl-$C_{1-7}$-alkyl, $C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, phenyl, pyridyl, pyrrolidinyl, phenyloxy and phenyl-$C_{1-7}$-alkoxy;
$R^5$ is hydrogen or methyl;
or a pharmaceutically acceptable salts thereof.

12. The compound according to claim 1, selected from the group consisting of
3-(2-chloro-4-methoxy-phenyl)-1,1,1-trifluoro-2-(5-methyl-pyrazin-2-yl)-butan-2-ol,
3-(2-chloro-4-methoxy-phenyl)-1,1,1-trifluoro-2-(2-methyl-pyridin-4-yl)-butan-2-ol,
3-(2-chloro-4-ethoxy-phenyl)-1,1,1-trifluoro-2-(2-methyl-pyridin-4-yl)-pentan-2-ol,
3-(2-chloro-4-propoxy-phenyl)-1,1,1-trifluoro-2-(2-methyl-pyridin-4-yl)-hexan-2-ol,
3-(2,3-dichloro-4-methoxy-phenyl)-1,1,1-trifluoro-2-(2-methyl-pyridin-4-yl)-butan-2-ol,
3-(2-chloro-5-methoxy-phenyl)-1,1,1-trifluoro-2-(2-methyl-pyridin-4-yl)-butan-2-ol,
3-(2,5-dichloro-phenyl)-1,1,1-trifluoro-2-(2-methyl-pyridin-4-yl)-butan-2-ol,
3-(2,4-dichloro-phenyl)-1,1,1-trifluoro-2-pyridin-3-yl-butan-2-ol,
3-(2,4-dichloro-phenyl)-1,1,1-trifluoro-2-pyridin-4-yl-butan-2-ol,
3-(2,4-dichloro-phenyl)-1,1,1-trifluoro-2-pyridin-2-yl-butan-2-ol,
3-(2,4-dichloro-phenyl)-1,1,1-trifluoro-2-pyridin-3-yl-heptan-2-ol, 3-(2,4-dichloro-phenyl)-1,1,1-trifluoro-2-pyridin-3-yl-hexan-2-ol,
3-(2,4-dichloro-phenyl)-1,1,1-trifluoro-2-pyridin-3-yl-pentan-2-ol,
4-cyclopropyl-3-(2,4-dichloro-phenyl)-1,1,1-trifluoro-2-pyridin-3-yl-butan-2-ol,
3-(4-chloro-2-fluoro-phenyl)-1,1,1-trifluoro-2-pyridin-3-yl-butan-2-ol,
3-(3,4-dichloro-phenyl)-1,1,1-trifluoro-2-pyridin-3-yl-butan-2-ol,
3-(2,3-dichloro-phenyl)-1,1,1-trifluoro-2-pyridin-3-yl-butan-2-ol,
3-(2,4-dichloro-phenyl)-1,1,1-trifluoro-2-(6-trifluoromethyl-pyridin-3-yl)-butan-2-ol,
3-(2,4-dichloro-phenyl)-1,1,1-trifluoro-2-pyridin-3-yl-4-[1,2,4]triazol-1-yl-butan-2-ol,
3-(2,4-dichloro-phenyl)-1,1,1-trifluoro-2-pyridin-4-yl-hexan-2-ol,
3-(2-chloro-4-fluoro-phenyl)-1,1,1-trifluoro-2-pyridin-4-yl-hexan-2-ol,
3-(2,4-dichloro-phenyl)-1,1,1-trifluoro-2-(2-methyl-pyridin-4-yl)-butan-2-ol,
3-(2,4-dichloro-phenyl)-1,1,1-trifluoro-2-(2-methyl-pyridin-4-yl)-hexan-2-ol,
3-(2,4-dichloro-phenyl)-1,1,1-trifluoro-2-pyrazin-2-yl-butan-2-ol,
3-(2-chloro-5-trifluoromethyl-phenyl)-1,1,1-trifluoro-2-pyridin-4-yl-butan-2-ol,
3-(2-chloro-6-fluoro-phenyl)-1,1,1-trifluoro-2-pyridin-4-yl-butan-2-ol,
3-(2-chloro-4-fluoro-phenyl)-2-(2-chloro-pyridin-4-yl)-1,1,1-trifluoro-butan-2-ol,
3-(2,4-dichloro-phenyl)-1,1,1-trifluoro-2-pyridazin-4-yl-butan-2-ol,
3-(2,4-dichloro-phenyl)-1,1,1-trifluoro-2-(2-methoxy-pyridin-4-yl)-butan-2-ol,
3-(2,4-dichloro-phenyl)-1,1,1-trifluoro-2-(5-methyl-pyrazin-2-yl)-butan-2-ol,
3-(2,4-dichloro-phenyl)-1,1,1-trifluoro-2-(6-methyl-pyrazin-2-yl)-butan-2-ol,
(2S,3S)-3-(2,4-dichloro-phenyl)-1,1,1-trifluoro-2-(6-methyl-pyrazin-2-yl)-butan-2-ol,
(2R,3R)-3-(2,4-dichloro-phenyl)-1,1,1-trifluoro-2-(6-methyl-pyrazin-2-yl)-butan-2-ol,
3-(2-chloro-4-fluoro-phenyl)-2-(2-chloro-6-methoxy-pyridin-4-yl)-1,1,1-trifluoro-butan-2-ol,
3-(2,4-dichloro-phenyl)-1,1,1-trifluoro-2-(1-methyl-1H-pyrazol-4-yl)-butan-2-ol,
2-(2-chloro-6-methyl-pyridin-4-yl)-3-(2,4-dichloro-phenyl)-1,1,1-trifluoro-butan-2-ol,
3-(2,4-dichloro-phenyl)-1,1,1-trifluoro-2-quinolin-3-yl-butan-2-ol,
3-(2,4-dichloro-phenyl)-1,1,1-trifluoro-2-pyrimidin-4-yl-butan-2-ol,
3-(2,4-dichloro-phenyl)-1,1,1-trifluoro-2-(1-methyl-1H-imidazol-4-yl)-butan-2-ol,
4-[2-(2,4-dichloro-phenyl)-1-methoxy-1-trifluoromethyl-propyl]-pyridine,
3-(2,4-dichloro-phenyl)-1,1,1-trifluoro-2-pyrazolo[1,5-a]pyridin-2-yl-butan-2-ol,
3-(2,4-dichloro-phenyl)-1,1,1-trifluoro-2-(1-methyl-1H-pyrazol-3-yl)-butan-2-ol,
3-(2,4-dichloro-phenyl)-1,1,1-trifluoro-2-imidazo[1,2-a]pyridin-2-yl-butan-2-ol,
3-(2,4-dichloro-phenyl)-1,1,1-trifluoro-2-quinolin-6-yl-butan-2-ol,
3-(2,4-dichloro-phenyl)-1,1,1-trifluoro-2-quinoxalin-6-yl-butan-2-ol,
2-(2-benzyloxy-pyridin-4-yl)-3-(2,4-dichloro-phenyl)-1,1,1-trifluoro-butan-2-ol,
3-(2,4-dichloro-phenyl)-1,1,1-trifluoro-2-(6-methoxy-pyridin-3-yl)-butan-2-ol,
3-(2,4-dichloro-phenyl)-1,1,1-trifluoro-2-(5-methyl-1-phenyl-1H-pyrazol-4-yl)-butan-2-ol,
2-benzothiazol-6-yl-3-(2,4-dichloro-phenyl)-1,1,1-trifluoro-butan-2-ol,
3-(2,4-dichloro-phenyl)-1,1,1-trifluoro-2-quinoxalin-2-yl-butan-2-ol,
3-(2,4-dichloro-phenyl)-1,1,1-trifluoro-2-(2-pyridin-4-yl-thiazol-4-yl)-butan-2-ol,
3-(2,4-dichloro-phenyl)-1,1,1-trifluoro-2-thiazol-2-yl-butan-2-ol,
7-[2-(2,4-dichloro-phenyl)-1-hydroxy-1-trifluoromethyl-propyl]-3,4-dihydro-1H-isoquinoline-2-carboxylic acid tert-butyl ester,
3-(2,4-dichloro-phenyl)-1,1,1-trifluoro-2-pyrimidin-5-yl-butan-2-ol,
2-(1-benzyl-1H-pyrazol-4-yl)-3-(2,4-dichloro-phenyl)-1,1,1-trifluoro-butan-2-ol,
3-(2,4-dichloro-phenyl)-1,1,1-trifluoro-2-(4-methyl-3,4-dihydro-2H-pyrido[3,2-b][1,4]oxazin-7-yl)-butan-2-ol,
3-(2-chloro-4-fluoro-phenyl)-1,1,1-trifluoro-2-quinolin-3-yl-butan-2-ol,
3-(2-chloro-4-methoxy-phenyl)-1,1,1-trifluoro-2-quinoxalin-2-yl-butan-2-ol,
3-(2-chloro-4-fluoro-phenyl)-1,1,1-trifluoro-2-quinolin-6-yl-butan-2-ol,
3-(2,4-dichloro-phenyl)-1,1,1-trifluoro-2-(6-pyrrolidin-1-yl-pyridin-2-yl)-butan-2-ol,
3-(2-chloro-4-fluoro-phenyl)-1,1,1-trifluoro-2-(6-methyl-pyrazin-2-yl)-butan-2-ol,
(2S,3S)-3-(2,4-dichloro-phenyl)-1,1,1-trifluoro-2-quinolin-6-yl-butan-2-ol,
(2R,3R)-3-(2,4-dichloro-phenyl)-1,1,1-trifluoro-2-quinolin-6-yl-butan-2-ol,
3-chloro-4-[3,3,3-trifluoro-2-hydroxy-1-methyl-2-(5-methyl-pyrazin-2-yl)-propyl]-phenol,
3-chloro-4-[3,3,3-trifluoro-2-hydroxy-1-methyl-2-(2-methyl-pyridin-4-yl)-propyl]-phenol,
3-(4-benzyloxy-2-chloro-phenyl)-1,1,1-trifluoro-2-(2-methyl-pyridin-4-yl)-butan-2-ol,
{4-[2-(2,4-dichloro-phenyl)-1-hydroxy-1-trifluoromethyl-propyl]-pyridin-2-yloxy}-acetic acid,
4-chloro-3-[3,3,3-trifluoro-2-hydroxy-1-methyl-2-(6-methyl-pyrazin-2-yl)-propyl]-benzoic acid,
3-[2-chloro-4-(2-methoxy-ethoxy)-phenyl]-1,1,1-trifluoro-2-(2-methyl-pyridin-4-yl)-butan-2-ol,
{3-chloro-4-[3,3,3-trifluoro-2-hydroxy-1-methyl-2-(2-methyl-pyridin-4-yl)-propyl]-phenoxy}-acetic acid tert-butyl ester,
{3-chloro-4-[3,3,3-trifluoro-2-hydroxy-1-methyl-2-(2-methyl-pyridin-4-yl)-propyl]-phenoxy}-acetic acid,
2-{3-chloro-4-[3,3,3-trifluoro-2-hydroxy-1-methyl-2-(5-methyl-pyrazin-2-yl)-propyl]-phenoxy}-acetamide,
3-{2-chloro-4-[2-(2-methoxy-ethoxy)-ethoxy]-phenyl}-1,1,1-trifluoro-2-(5-methyl-pyrazin-2-yl)-butan-2-ol,
{3-chloro-4-[3,3,3-trifluoro-2-hydroxy-1-methyl-2-(5-methyl-pyrazin-2-yl)-propyl]-phenoxy}-acetic acid tert-butyl ester,
acetic acid 2-{3-chloro-4-[3,3,3-trifluoro-2-hydroxy-1-methyl-2-(5-methyl-pyrazin-2-yl)-propyl]-phenoxy}-ethyl ester, (2-{3-chloro-4-[3,3,3-trifluoro-2-hydroxy-1-methyl-2-(5-methyl-pyrazin-2-yl)-propyl]-phenoxy}-ethyl)-carbamic acid tert-butyl ester,
3-[2-chloro-4-(2,2-difluoro-ethoxy)-phenyl]-1,1,1-trifluoro-2-(5-methyl-pyrazin-2-yl)-butan-2-ol,
3-[2-chloro-4-(2-methoxy-ethoxy)-phenyl]-1,1,1-trifluoro-2-(5-methyl-pyrazin-2-yl)-butan-2-ol,
3-[2-chloro-4-([1,2,4]oxadiazol-3-ylmethoxy)-phenyl]-1,1,1-trifluoro-2-(5-methyl-pyrazin-2-yl)-butan-2-ol,
3-[2-chloro-4-(5-methyl-isoxazol-3-ylmethoxy)-phenyl]-1,1,1-trifluoro-2-(5-methyl-pyrazin-2-yl)-butan-2-ol,
3-[2-chloro-4-(2-hydroxy-ethoxy)-phenyl]-1,1,1-trifluoro-2-(5-methyl-pyrazin-2-yl)-butan-2-ol,
3-[4-(2-amino-ethoxy)-2-chloro-phenyl]-1,1,1-trifluoro-2-(5-methyl-pyrazin-2-yl)-butan-2-ol,
3-[2-chloro-4-(1-methyl-1H-tetrazol-5-ylmethoxy)-phenyl]-1,1,1-trifluoro-2-(5-methyl-pyrazin-2-yl)-butan-2-ol,
3-[2-chloro-4-(3-methyl-[1,2,4]thiadiazol-5-ylmethoxy)-phenyl]-1,1,1-trifluoro-2-(5-methyl-pyrazin-2-yl)-butan-2-ol,
3-(2-chloro-4-fluoro-phenyl)-1,1,1-trifluoro-2-(2-methoxy-pyridin-4-yl)-butan-2-ol,
2-(6-chloro-pyrazin-2-yl)-3-(2,4-dichloro-phenyl)-1,1,1-trifluoro-butan-2-ol,
3-(2,4-dichloro-phenyl)-1,1,1-trifluoro-2-isoquinolin-5-yl-butan-2-ol,
2-cinnolin-4-yl-3-(2,4-dichloro-phenyl)-1,1,1-trifluoro-butan-2-ol,
3-(2,4-dichloro-phenyl)-1,1,1-trifluoro-2-pyrazolo[1,5-a]pyridin-3-yl-butan-2-ol,
3-(2,4-dichloro-phenyl)-1,1,1-trifluoro-2-(1-phenethyl-1H-pyrazol-4-yl)-butan-2-ol,
5-[2-(2,4-dichloro-phenyl)-1-hydroxy-1-trifluoromethyl-propyl]-pyridine-2-carbonitrile,
3-(2-chloro-4-phenethyloxy-phenyl)-1,1,1-trifluoro-2-(2-methyl-pyridin-4-yl)-butan-2-ol,
3-(2,4-dichloro-phenyl)-1,1,1-trifluoro-2-(2-methoxy-pyrimidin-5-yl)-butan-2-ol,
3-(2-chloro-4-methoxy-phenyl)-1,1,1-trifluoro-2-pyridin-4-yl-butan-2-ol,
3-chloro-4-(3,3,3-trifluoro-2-hydroxy-1-methyl-2-pyridin-4-yl-propyl)-phenol,
3-(2-chloro-4-methoxy-phenyl)-1,1,1-trifluoro-2-(3-isopropyl-3H-benzotriazol-5-yl)-butan-2-ol,
3-(2-chloro-4-methoxy-phenyl)-2-cinnolin-4-yl-1,1,1-trifluoro-butan-2-ol,
3-chloro-4-(2-cinnolin-4-yl-3,3,3-trifluoro-2-hydroxy-1-methyl-propyl)-phenol,
3-(2-chloro-4-methoxy-phenyl)-1,1,1-trifluoro-2-pyrazolo[1,5-a]pyridin-3-yl-butan-2-ol,
3-chloro-4-(3,3,3-trifluoro-2-hydroxy-1-methyl-2-pyrazolo[1,5-a]pyridin-3-yl-propyl)-phenol,
2-(2-chloro-pyridin-4-yl)-3-{2-chloro-4-[3-((1H)-tetrazol-5-yl)-propoxy]-phenyl}-1,1,1-trifluoro-butan-2-ol,
3-(2-chloro-4-hydroxymethyl-phenyl)-2-(2-chloro-pyridin-4-yl)-1,1,1-trifluoro-butan-2-ol,
{3-chloro-4-[2-(2-chloro-pyridin-4-yl)-3,3,3-trifluoro-2-hydroxy-1-methyl-propyl]-phenyl}-acetic acid,
3-{3-chloro-4-[2-(2-chloro-pyridin-4-yl)-3,3,3-trifluoro-2-hydroxy-1-methyl-propyl]-phenyl}-propionic acid,
3-(2-chloro-5-methoxy-phenyl)-2-(2-chloro-pyridin-4-yl)-1,1,1-trifluoro-butan-2-ol,
4-chloro-3-[2-(2-chloro-pyridin-4-yl)-3,3,3-trifluoro-2-hydroxy-1-methyl-propyl]-phenol,
3-(2,4-dichloro-phenyl)-5,5,5-trifluoro-4-hydroxy-4-(6-methyl-pyrazin-2-yl)-pentanoic acid methyl ester,
3-(2,4-dichloro-phenyl)-5,5,5-trifluoro-4-hydroxy-4-(6-methyl-pyrazin-2-yl)-pentanoic acid,
4-[2-(2,4-dichloro-phenyl)-1-hydroxy-1-trifluoromethyl-propyl]-1H-pyridin-2-one,
{4-[2-(2,4-dichloro-phenyl)-1-hydroxy-1-trifluoromethyl-propyl]-pyridin-2-yloxy}-acetic acid methyl ester,
{4-[2-(2,4-dichloro-phenyl)-1-hydroxy-1-trifluoromethyl-propyl]-2-oxo-2H-pyridin-1-yl}-acetic acid methyl ester,
{4-[2-(2,4-dichloro-phenyl)-1-hydroxy-1-trifluoromethyl-propyl]-2-oxo-2H-pyridin-1-yl}-acetic acid,
2-{4-[2-(2,4-dichloro-phenyl)-1-hydroxy-1-trifluoromethyl-propyl]-pyridin-2-yloxy}-acetamide,
3-(2,4-dichloro-phenyl)-1,1,1-trifluoro-2-[2-(2-methoxy-ethoxy)-pyridin-4-yl]-butan-2-ol,
{4-[2-(2,4-dichloro-phenyl)-1-hydroxy-1-trifluoromethyl-propyl]-pyridin-2-yloxy}-acetonitrile,
3-(2,4-dichloro-phenyl)-1,1,1-trifluoro-2-[2-(2-hydroxy-ethoxy)-pyridin-4-yl]-butan-2-ol,
2-{4-[2-(2,4-dichloro-phenyl)-1-hydroxy-1-trifluoromethyl-propyl]-pyridin-2-yloxy}-1-morpholin-4-yl-ethanone,
4-[2-(2,4-dichloro-phenyl)-4,4,4-trifluoro-3-hydroxy-3-(6-methyl-pyrazin-2-yl)-butyl]-benzoic acid ethyl ester,
4-[2-(2,4-dichloro-phenyl)-4,4,4-trifluoro-3-hydroxy-3-(6-methyl-pyrazin-2-yl)-butyl]-benzoic acid,
4-chloro-3-[3,3,3-trifluoro-2-hydroxy-1-methyl-2-(6-methyl-pyrazin-2-yl)-propyl]-benzoic acid methyl ester,
3-(2-chloro-4-methoxy-phenyl)-2-(2-chloro-pyridin-4-yl)-1,1,1-trifluoro-butan-2-ol,
3-chloro-4-[2-(2-chloro-pyridin-4-yl)-3,3,3-trifluoro-2-hydroxy-1-methyl-propyl]-phenol,
2-{3-chloro-4-[2-(2-chloro-pyridin-4-yl)-3,3,3-trifluoro-2-hydroxy-1-methyl-propyl]-phenoxy}-2-methyl-propionamide,
3-chloro-4-[2-(2-chloro-pyridin-4-yl)-3,3,3-trifluoro-2-hydroxy-1-methyl-propyl]-benzoic acid methyl ester,
4-[2-(2-chloro-4-methoxycarbonyl-phenyl)-1-hydroxy-1-trifluoromethyl-propyl]-pyridine-2-carboxylic acid methyl ester,
3-chloro-4-[2-(2-chloro-pyridin-4-yl)-3,3,3-trifluoro-2-hydroxy-1-methyl-propyl]-benzoic acid,
4-[2-(4-carboxy-2-chloro-phenyl)-1-hydroxy-1-trifluoromethyl-propyl]-pyridine-2-carboxylic acid,
3-(2-chloro-4-methoxy-phenyl)-1,1,1-trifluoro-2-(2-iodo-pyridin-4-yl)-butan-2-ol,
4-{4-[2-(2-chloro-4-methoxy-phenyl)-1-hydroxy-1-trifluoromethyl-propyl]-pyridin-2-yl}-benzoic acid ethyl ester,
4-{4-[2-(2-chloro-4-methoxy-phenyl)-1-hydroxy-1-trifluoromethyl-propyl]-pyridin-2-yl}-benzoic acid,
3-{4-[2-(2-chloro-4-methoxy-phenyl)-1-hydroxy-1-trifluoromethyl-propyl]-pyridin-2-yl}-benzoic acid methyl ester,
3-{4-[2-(2-chloro-4-methoxy-phenyl)-1-hydroxy-1-trifluoromethyl-propyl]-pyridin-2-yl}-benzoic acid,
3-(2-chloro-4-fluoro-phenyl)-1,1,1-trifluoro-2-(2-iodo-pyridin-4-yl)-butan-2-ol,
3-{4-[2-(2-chloro-4-fluoro-phenyl)-1-hydroxy-1-trifluoromethyl-propyl]-pyridin-2-yl}-benzoic acid methyl ester,
5-{4-[2-(2-chloro-4-fluoro-phenyl)-1-hydroxy-1-trifluoromethyl-propyl]-pyridin-2-yl}-2-fluoro-benzonitrile,
3-{4-[2-(2-chloro-4-fluoro-phenyl)-1-hydroxy-1-trifluoromethyl-propyl]-pyridin-2-yl}-benzoic acid, 4'-[2-(2-chloro-4-trifluoromethanesulfonyloxy-phenyl)-1-hydroxy-1-trifluoromethyl-propyl]-3,4,5,6-tetrahydro-2H-[1,2']bipyridinyl-4-carboxylic acid ethyl ester, 4'-[2-(2-chloro-4-hydroxy-phenyl)-1-hydroxy-1-trifluoromethyl-propyl]-3,4,5,6-tetrahydro-2H-[1,2']bipyridinyl-4-carboxylic acid, 2-chloro-5-{4-[2-(2-chloro-4-fluoro-phenyl)-1-hydroxy-1-trifluoromethyl-propyl]-pyridin-2-yl}-benzoic acid ethyl ester, 5-{4-[2-(2-chloro-4-fluoro-phenyl)-1-hydroxy-1-trifluoromethyl-propyl]pyridin-2-yl}-2-fluoro-benzoic acid ethyl ester, 5-{4-[2-(2-chloro-4-fluoro-phenyl)-1-hydroxy-1-trifluoromethyl-propyl]pyridin-2-yl}-2-fluoro-benzoic acid, 2-chloro-5-{4-[2-(2-chloro-4-fluoro-phenyl)-1-hydroxy-1-trifluoromethyl-propyl]-pyridin-2-yl}-benzoic acid, 4'-[2-(2-chloro-4-methoxy-phenyl)-1-hydroxy-1-trifluoromethyl-propyl]-3,4,5,6-tetrahydro-2H-[1,2']bipyridinyl-4-carboxylic acid ethyl ester, 4'-[2-(2-chloro-4-methoxy-phenyl)-1-hydroxy-1-trifluoromethyl-propyl]-3,4,5,6-tetrahydro-2H-[1,2']bipyridinyl-4-carboxylic acid, 4'-[2-(2-chloro-4-ethoxy-phenyl)-1-hydroxy-1-trifluoromethyl-propyl]-3,4,5,6-tetrahydro-2H-[1,2']bipyridinyl-4-carboxylic acid, 3-(3,4-dichloro-phenyl)-1,1,1-trifluoro-2-pyridin-4-yl-butan-2-ol, 1,1,1-trifluoro-3-(4-methoxy-2-methyl-phenyl)-2-pyridin-4-yl-butan-2-ol, 3-(2,4-difluoro-phenyl)-1,1,1-trifluoro-2-pyridin-4-yl-butan-2-ol, 3-(2-chloro-4-diallylamino-phenyl)-2-(2-chloro-pyridin-4-yl)-1,1,1-trifluoro-butan-2-ol, N-{3-chloro-4-[2-(2-chloro-pyridin-4-yl)-3,3,3-trifluoro-2-hydroxy-1-methyl-propyl]-phenyl}-methanesulfonamide, N-{3-chloro-4-[2-(2-chloro-pyridin-4-yl)-3,3,3-trifluoro-2-hydroxy-1-methyl-propyl]-phenyl}-benzamide, 3-(2-chloro-4-fluoro-phenyl)-2-(6-chloro-pyridin-3-yl)-1,1,1-trifluoro-butan-2-ol, 5-[2-(2-chloro-4-fluoro-phenyl)-1-hydroxy-1-trifluoromethyl-propyl]-pyridine-2-carboxylic acid, 4-[2-(2-chloro-4-fluoro-phenyl)-1-hydroxy-1-trifluoromethyl-propyl]-pyridine-2-carboxylic acid, 3-(4-bromo-2-chloro-phenyl)-1,1,1-trifluoro-2-(2-methyl-pyridin-4-yl)-butan-2-ol, 1-[1-(2,4-dichloro-phenyl)-cyclopropyl]-2,2,2-trifluoro-1-quinolin-3-yl-ethanol, 1-(2-chloro-pyridin-4-yl)-1-[1-(2,4-dichloro-phenyl)-cyclopropyl]-2,2,2-trifluoro-ethanol, 2-(2-chloro-pyridin-4-yl)-3-(2,4-dichloro-phenyl)-1,1,1-trifluoro-3-methyl-butan-2-ol, 3-(2-chloro-4-methoxy-phenyl)-1,1,1-trifluoro-2-quinolin-3-yl-butan-2-ol, 3-chloro-4-(3,3,3-trifluoro-2-hydroxy-1-methyl-2-quinolin-3-yl-propyl)-phenol, 3-[2-chloro-4-(4-methanesulfonyl-benzyloxy)-phenyl]-1,1,1-trifluoro-2-quinolin-3-yl-butan-2-ol, benzenesulfonic acid 3-chloro-4-(3,3,3-trifluoro-2-hydroxy-1-methyl-2-quinolin-3-yl-propyl)-phenyl ester, 3-(2-chloro-4-methoxy-phenyl)-1,1,1-trifluoro-2-isoquinolin-5-yl-butan-2-ol, 3-chloro-4-(3,3,3-trifluoro-2-hydroxy-2-isoquinolin-5-yl-1-methyl-propyl)-phenol, 3-[2-(2-chloro-4-methoxy-phenyl)-1-hydroxy-1-trifluoromethyl-propyl]-quinoline-6-carbonitrile, 3-(2-chloro-4-methoxy-phenyl)-1,1,1-trifluoro-2-(6-methoxy-pyridin-3-yl)-butan-2-ol, 5-[2-(2-chloro-4-methoxy-phenyl)-1-hydroxy-1-trifluoromethyl-propyl]-1H-pyridin-2-one, 5-[2-(2-chloro-4-methoxy-phenyl)-1-hydroxy-1-trifluoromethyl-propyl]-1-methyl-1H-pyridin-2-one, 5-[2-(2-chloro-4-hydroxy-phenyl)-1-hydroxy-1-trifluoromethyl-propyl]-1-methyl-1H-pyridin-2-one, 4-{3-chloro-4-[3,3,3-trifluoro-2-hydroxy-1-methyl-2-(1-methyl-6-oxo-1,6-dihydro-pyridin-3-yl)-propyl]-phenoxy}-3-fluoro-benzonitrile, 3-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzonitrile, 5-{2-[2-chloro-4-(4-fluoro-3-methoxy-phenoxy)-phenyl]-1-hydroxy-1-trifluoromethyl-propyl}-1-methyl-1H-pyridin-2-one, 5-{2-[2-chloro-4-(4-fluoro-3-hydroxy-phenoxy)-phenyl]-1-hydroxy-1-trifluoromethyl-propyl}-1-methyl-1H-pyridin-2-one, 5-[2-(2,4-dichloro-phenyl)-1-hydroxy-1-trifluoromethyl-propyl]-1-methyl-1H-pyridin-2-one, 5-[2-(2,4-dichloro-phenyl)-1-hydroxy-1-trifluoromethyl-propyl]-1-ethyl-1H-pyridin-2-one, 5-[2-(4-bromo-2-chloro-phenyl)-1-hydroxy-1-trifluoromethyl-propyl]-1-methyl-1H-pyridin-2-one, 3-(4-bromo-2-chloro-phenyl)-1,1,1-trifluoro-2-(6-methoxy-pyridin-3-yl)-butan-2-ol, 5-[2-(4-bromo-2-chloro-phenyl)-1-hydroxy-1-trifluoromethyl-propyl]-1H-pyridin-2-one, 5-[2-(4-bromo-2-chloro-phenyl)-1-hydroxy-1-trifluoromethyl-propyl]-1-ethyl-1H-pyridin-2-one, 5-[2-(2-chloro-5-methoxy-phenyl)-1-hydroxy-1-trifluoromethyl-propyl]-1-methyl-1H-pyridin-2-one, 5-[2-(2,3-dichloro-4-methoxy-phenyl)-1-hydroxy-1-trifluoromethyl-propyl]-1-methyl-1H-pyridin-2-one, 5-[2-(2,3-dichloro-4-hydroxy-phenyl)-1-hydroxy-1-trifluoromethyl-propyl]-1-methyl-1H-pyridin-2-one, 5-[2-(2-chloro-5-fluoro-4-methoxy-phenyl)-1-hydroxy-1-trifluoromethyl-propyl]-1-methyl-1H-pyridin-2-one, or a pharmaceutically acceptable salts thereof.

13. A pharmaceutical composition, comprising a therapeutically effective amount of a compound according to claim 1 and a pharmaceutically acceptable carrier and/or adjuvant.

* * * * *